(12) United States Patent
Kodama

(10) Patent No.: US 8,003,294 B2
(45) Date of Patent: Aug. 23, 2011

(54) PHOTOSENSITIVE COMPOSITION, COMPOUND USED FOR PHOTOSENSITIVE COMPOSITION AND PATTERN-FORMING METHOD USING PHOTOSENSITIVE COMPOSITION

(75) Inventor: Kunihiko Kodama, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 351 days.

(21) Appl. No.: 12/045,421

(22) Filed: Mar. 10, 2008

(65) Prior Publication Data

US 2008/0220371 A1 Sep. 11, 2008

(30) Foreign Application Priority Data

Mar. 9, 2007 (JP) ................................. 2007-060061
Feb. 6, 2008 (JP) ................................. 2008-026524

(51) Int. Cl.
*G03F 7/039* (2006.01)
*G03F 7/20* (2006.01)
*G03F 7/30* (2006.01)

(52) U.S. Cl. ..................... 430/270.1; 430/326; 430/910; 430/919; 430/921; 430/925; 430/945

(58) Field of Classification Search .......................... None
See application file for complete search history.

(56) References Cited

U.S. PATENT DOCUMENTS

| 6,777,160 B2 * | 8/2004 | Sato et al. ................... 430/270.1 |
| 7,718,344 B2 * | 5/2010 | Kamimura et al. ......... 430/270.1 |
| 2003/0207201 A1 * | 11/2003 | Hatakeyama et al. ..... 430/270.1 |
| 2006/0264528 A1 * | 11/2006 | Wada ............................ 522/130 |
| 2008/0081282 A1 * | 4/2008 | Kamimura et al. ......... 430/270.1 |

FOREIGN PATENT DOCUMENTS

| JP | 2002-268223 A | 9/2002 |
| JP | 2003-231673 A | 8/2003 |
| JP | 2003-261529 A | 9/2003 |
| JP | 2004-12554 A | 1/2004 |
| JP | 2004-62154 A | 2/2004 |
| WO | 2005/040922 A1 | 5/2005 |

* cited by examiner

*Primary Examiner* — Sin J. Lee
(74) *Attorney, Agent, or Firm* — Sughrue Mion, PLLC

(57) ABSTRACT

A photosensitive composition comprises: (A) a compound capable of generating an acid represented by formula (I) upon irradiation with actinic ray or radiation; and (B) a resin that decomposes by the action of an acid to its increase solubility in an alkali developer

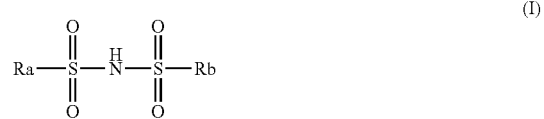

(I)

wherein Ra represents an alkyl group substituted with a fluorine atom, or an aryl group substituted with a fluorine atom or a group having a fluorine atom; Rb represents an alkyl group not substituted with a fluorine atom on α-position of the alkyl group, or an aryl group not substituted with a fluorine atom or a group having a fluorine atom.

8 Claims, No Drawings

PHOTOSENSITIVE COMPOSITION, COMPOUND USED FOR PHOTOSENSITIVE COMPOSITION AND PATTERN-FORMING METHOD USING PHOTOSENSITIVE COMPOSITION

BACKGROUND OF THE INVENTION

1. Field of the Invention

The present invention relates to a photosensitive composition used in a manufacturing process of semiconductors, such as IC, manufactures of liquid crystals, circuit substrates of thermal heads and the like, and other photo-fabrication processes, and also relates to a composition used for the photosensitive composition and a pattern forming method using the photosensitive composition. More specifically, the invention relates to a photosensitive composition suitable in cases of using far ultraviolet rays of 250 nm or less, preferably 220 nm or less, as an exposure light source and electron beams as an irradiation source, and a pattern forming method using the same.

2. Description of the Related Art

Chemical amplification photosensitive compositions are pattern-forming materials capable of generating an acid at a part irradiated with radiation such as far ultraviolet ray, changing the solubility in a developing solution of the irradiated part and non-irradiated part with actinic radiation by the reaction with the acid as a catalyst, and forming a pattern on a substrate.

When a KrF excimer laser is used as an exposure light source, resins having poly(hydroxystyrene) as a fundamental skeleton that is small in absorption in the region of 248 nm are mainly used, so that high sensitivity and high resolution are secured and a good pattern is formed as compared with conventional naphthoquinonediazide/novolak resins.

On the other hand, when a light source of further shorter wavelength, e.g., an ArF excimer laser (193 nm), is used as an exposure light source, since compounds having an aromatic group substantially show large absorption in the region of 193 nm, even the above chemical amplification photosensitive compositions are not sufficient.

Therefore, resists for an ArF excimer laser containing a resin having an alicyclic hydrocarbon structure have been developed. As photo-acid generators capable of generating an acid at a part irradiated with radiation such as far ultraviolet ray, various compounds have been developed. For example, compositions containing a compound capable of generating a bis(sulfonyl)imidic acid upon irradiation with far ultraviolet rays are disclosed. (Refer to JP-A-2003-261529, JP-A-2003-231673, JP-A-2002-268223, JP-A-2004-12554, JP-A-2004-62154, and WO 2005/040,922).

However, these compounds are still insufficient in various points and further improvements are required. For example, it has come to be known that unevenness of in-plane temperature in a wafer in heating by a hot plate and the like after exposure (PEB: Post Exposure Bake) influences a pattern to be obtained, and when a wafer having a large aperture is used, line widths of a pattern obtained in the wafer are various. It is required to improve such PEB temperature dependency.

Further, it is difficult to reconcile the improvement of PEB temperature dependency with the widening of exposure latitude, so that it is desired to improve PEB temperature dependency and exposure latitude at the same time.

SUMMARY OF THE INVENTION

Accordingly, an object of the invention is to provide a photosensitive composition improved in PEB temperature dependency and exposure latitude, and a pattern-forming method using the same.

(1) A photosensitive composition containing (A) a compound capable of generating an acid represented by the following formula (I) upon irradiation with actinic ray or radiation, and (B) a resin that decomposes by the action of an acid to increase its solubility in an alkali developer

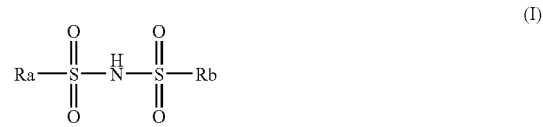

wherein Ra represents an alkyl group substituted with a fluorine atom, or an aryl group substituted with a fluorine atom or a group having a fluorine atom; Rb represents an alkyl group not substituted with a fluorine atom on the a-position, or an aryl group not substituted with a fluorine atom or a group having a fluorine atom.

(2) The photosensitive composition as described in the above item (1), wherein component (A) is a sulfonium salt compound or an iodonium salt compound having an anion of an acid represented by formula (I).

(3) A compound capable of generating an acid represented by the following formula (I) upon irradiation with actinic ray or radiation:

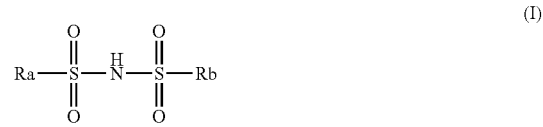

wherein Ra represents an alkyl group substituted with a fluorine atom, or an aryl group substituted with a fluorine atom or a group having a fluorine atom; and Rb represents an alkyl group not substituted with a fluorine atom on the α-position, or an aryl group not substituted with a fluorine atom or a group having a fluorine atom.

(4) A compound represented by the following formula (Ia):

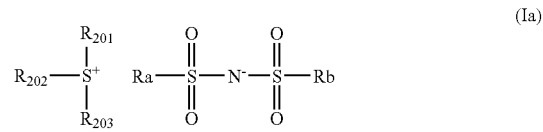

wherein $R^{201}$, $R^{202}$ and $R^{203}$ each represents an organic group; Ra represents an alkyl group substituted with a fluorine atom, or an aryl group substituted with a fluorine atom or a group having a fluorine atom; and Rb represents an alkyl group not substituted with a fluorine atom on the α-position, or an aryl group not substituted with a fluorine atom or a group having a fluorine atom.

(5) A pattern-forming method comprising the processes of forming a photosensitive film with the photosensitive composition as described in the above item (1) or (2), exposing and developing the photosensitive film.

Preferred embodiments of the invention are further described below.

(6) The photosensitive composition as described in the above item (1) or (2), wherein the resin of component (B) is a resin having a hydroxystyrene repeating unit.

(7) The photosensitive composition as described in the above item (1) or (2), wherein the resin of component (B) is a resin having a monocyclic or polycyclic alicyclic hydrocarbon structure.

(8) The photosensitive composition as described in the above item (1) or (2), wherein the resin of component (B) is a resin having a lactone structure.

(9) The photosensitive composition as described in any of the above items (1), (2), (6) to (8), wherein Ra in formula (I) is selected from a trifluoromethyl group, a pentafluoro-ethyl group, a heptafluoropropyl group, a nonafluorobutyl group, a pentafluorophenyl group, and a 3,5-bis(trifluoro-methyl)phenyl group.

(10) The photosensitive composition as described in any of the above items (1), (2), (6) to (9), which further contains (A2) a compound capable of generating an acid represented by any of the following formulae (AC1) to (AC3) upon irradiation with actinic ray or radiation:

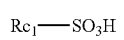
AC1

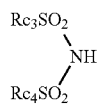
AC2

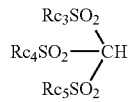
AC3 wherein Rc1 represents an organic group; and $Rc_3$, $Rc_4$ and $Rc_5$ each represents a perfluoroalkyl group, and $Rc_3$ and $Rc_4$ may be bonded to each other to form a ring.

(11) The photosensitive composition as described in any of the above items (1), (2), (6) to (10), wherein the resin of component (B) has an acid-decomposable group having an acetal structure.

DETAILED DESCRIPTION OF THE INVENTION

The embodiments of the invention will be described below.

In the description of a group (an atomic group) in the specification of the invention, the description not referring to substitution or unsubstitution includes both a group not having a substituent and a group having a substituent. For example, "an alkyl group" includes not only an alkyl group having no substituent (an unsubstituted alkyl group) but also an alkyl group having a substituent (a substituted alkyl group).

(A) A compound capable of generating an acid represented by formula (I) upon irradiation with actinic ray or radiation:

The photosensitive composition according to the invention contains a compound capable of generating an acid represented by the following formula (I) upon irradiation with actinic ray or radiation.

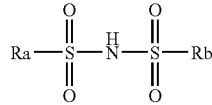
(I)

In formula (I), Ra represents an alkyl group substituted with a fluorine atom, or an aryl group substituted with a fluorine atom or a group having a fluorine atom.

Rb represents an alkyl group not substituted with a fluorine atom on the α-position, or an aryl group not substituted with a fluorine atom or a group having a fluorine atom.

As the alkyl group represented by Ra in formula (I), a straight chain, branched, or cyclic alkyl group having from 1 to 30 carbon atoms, and an alkyl group obtained by combining these alkyl groups are exemplified.

The alkyl group represented by Ra is an alkyl group substituted with a fluorine atom, preferably a perfluoroalkyl group, and more preferably a trifluoromethyl group, a pentafluoroethyl group, a heptafluoropropyl group, or a nonafluorobutyl group.

The alkyl group represented by Ra may further have a substituent, and as preferred substituents, halogen atoms other than a fluorine atom, an alkoxyl group, an alkoxycarbonyl group, a cyano group, and an oxo group are exemplified.

As the aryl group represented by Ra, an aryl group having from 6 to 14 carbon atoms is exemplified, and preferably a phenyl group is exemplified.

The aryl group as Ra is an aryl group substituted with a fluorine atom or a group having a fluorine atom, and preferably a pentafluorophenyl group, and a 3,5-bis-(trifluoromethyl)phenyl group are exemplified.

The aryl group represented by Ra may further have a substituent, and as preferred substituents, an alkyl group, halogen atoms other than a fluorine atom, an alkoxyl group, an alkoxycarbonyl group, and a cyano group are exemplified.

As the alkyl group represented by Rb that is not substituted with a fluorine atom on the α-position, a straight chain, branched, or cyclic alkyl group having from 1 to 30 carbon atoms, and an alkyl group obtained by combining these alkyl groups are exemplified.

The alkyl group represented by Rb may have a substituent, and as preferred substituents, an alkoxyl group, an alkoxycarbonyl group, a cyano group, and an oxo group are exemplified.

As the aryl group represented by Rb that is not substituted with a fluorine atom or a group having a fluorine atom, an aryl group having from 6 to 14 carbon atoms is exemplified, and preferably a phenyl group is exemplified.

The aryl group represented by Rb may have a substituent, and as preferred substituents, an alkyl group, an alkoxyl group, an alkoxycarbonyl group, and a cyano group are exemplified.

The specific examples of the acids represented by formula (I) are shown below, but the invention is not restricted to these compounds.

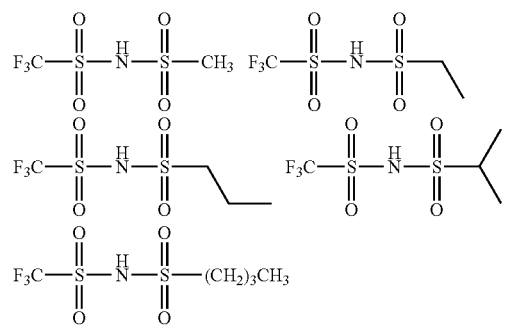

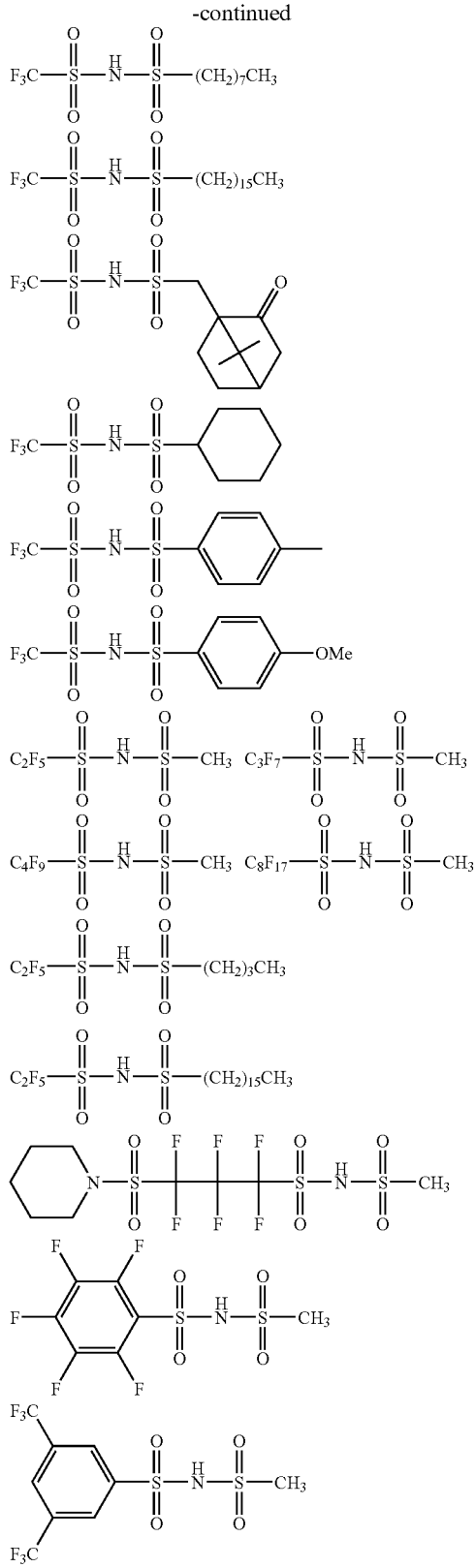

Of the compounds capable of generating an acid represented by formula (I) upon irradiation with actinic ray or radiation, a compound represented by the following formula (ZIa) or (ZIIa) can be exemplified as a preferred compound.

$$R_{202}—\overset{R_{201}}{\underset{R_{203}}{S^+}}\quad Xd^- \qquad \text{(ZIa)}$$

$$R_{204}—I^+—R_{205} \qquad \text{(ZIIa)}$$
$$Xd^-$$

In formula (ZIa), $R_{201}$, $R_{202}$ and $R_{203}$ each represents an organic group.

$Xd^-$ represents an anion of an acid represented by formula (I).

In formula (ZIa), any two of $R_{201}$, $R_{202}$ and $R_{203}$ may be bonded to each other to form a cyclic structure, and an oxygen atom, a sulfur atom, an ester bond, an amido bond or a carbonyl group may be contained in the ring. As the group formed by any two of $R_{201}$, $R_{202}$ and $R_{203}$ by bonding, an alkylene group (e.g., a butylene group and a pentylene group) can be exemplified.

As the specific examples of the organic groups represented by $R_{201}$, $R_{202}$ and $R_{203}$, the corresponding groups in compounds (ZI-1a), (ZI-2a) and (ZI-3a) described later can be exemplified.

A compound represented by formula (ZIa) may be a compound having a plurality of structures represented by formula (ZIa). For instance, a compound represented by formula (ZIa) may be a compound having a structure that at least one of $R_{201}$, $R_{202}$ and $R_{203}$ is bonded to at least one of $R_{201}$, $R_{202}$ and $R_{203}$ of another compound represented by formula (ZIa).

As further preferred components (ZIa), the compounds (ZI-1a), (ZI-2a) and (ZI-3a) described below can be exemplified.

Compound (ZI-1a) is an arylsulfonium compound that at least one of $R_{201}$, $R_{202}$ and $R_{203}$ in formula (ZIa) represents an aryl group, that is, a compound having arylsulfonium as a cation.

All of $R_{201}$, $R_{202}$ and $R_{203}$ of the arylsulfonium compound may be aryl groups, or a part of $R_{201}$, $R_{202}$ and $R_{203}$ may be an aryl group and the remainder may be an alkyl group or a cycloalkyl group.

As the arylsulfonium compound, e.g., a triarylsulfonium compound, a diarylalkylsulfonium compound, an aryldialkyl-sulfonium compound, a diarylcycloalkylsulfonium compound, and an aryldicycloalkylsulfonium compound can be exemplified.

As the aryl group of the arylsulfonium compound, an aryl group, e.g., a phenyl group and a naphthyl group, and an aryl group having a hetero atom, e.g., an indole residue and a pyrrole residue are preferred, and a phenyl group and an indole residue are more preferred. When the arylsulfonium compound has two or more aryl groups, these two or more aryl groups may be the same or different.

The alkyl group incorporated into the arylsulfonium compound according to necessity is preferably a straight chain or branched alkyl group having from 1 to 15 carbon atoms, e.g., a methyl group, an ethyl group, a propyl group, an n-butyl group, a sec-butyl group, a t-butyl group, etc., can be exemplified.

The cycloalkyl group incorporated into the arylsulfonium compound according to necessity is preferably a cycloalkyl group having from 3 to 15 carbon atoms, e.g., a cyclopropyl group, a cyclobutyl group, a cyclohexyl group, etc., can be exemplified.

The aryl group, alkyl group and cycloalkyl group represented by $R_{201}$, $R_{202}$ and $R_{203}$ may have a substituent, e.g., an alkyl group (e.g., having from 1 to 15 carbon atoms), a cycloalkyl group (e.g., having from 3 to 15 carbon atoms), an aryl group (e.g., having from 6 to 14 carbon atoms), an alkoxyl group (e.g., having from 1 to 15 carbon atoms), a halogen atom, a hydroxyl group, and a phenylthio group are exemplified as the substituents. The preferred substituents are a straight chain or branched alkyl group having from 1 to 12 carbon atoms, a cycloalkyl group having from 3 to 12 carbon atoms, and a straight chain, branched, or cyclic alkoxyl group having from 1 to 12 carbon atoms, and the most preferred substituents are an alkyl group having from 1 to 4 carbon atoms, and an alkoxyl group having from 1 to 4 carbon atoms. The substituent may be substituted on any one of three of $R_{201}$, $R_{202}$ and $R_{203}$, or may be substituted on all of the three. When $R_{201}$, $R_{202}$ and $R_{203}$ each represents an aryl group, it is preferred that the substituent be substituted on the p-position of the aryl group.

The arylsulfonium cation is preferably triphenyl-sulfonium cation, naphthyltetrahydrothiophenium cation, or phenyltetrahydrothiophenium cation, each of which may be substituted.

Compound (ZI-2a) is described below.

Compound (ZI-2a) is a compound in the case where $R_{201}$, $R_{202}$ and $R_{203}$ in formula (ZIa) each represents an organic group not having an aromatic ring. The aromatic ring here also includes an aromatic ring containing a hetero atom.

The organic group not having an aromatic ring represented by $R_{201}$, $R_{202}$ and $R_{203}$ generally has from 1 to 30 carbon atoms, and preferably from 1 to 20 carbon atoms.

$R_{201}$, $R_{202}$ and $R_{203}$ each preferably represents an alkyl group, a cycloalkyl group, an allyl group, or a vinyl group, more preferably represents a straight chain, branched or cyclic 2-oxoalkyl group, or an alkoxycarbonylmethyl group, and most preferably represents a straight chain or branched 2-oxoalkyl group.

The alkyl group represented by $R_{201}$, $R_{202}$ and $R_{203}$ may be either straight chain or branched, and preferably a straight chain or branched alkyl group having from 1 to 10 carbon atoms, e.g., a methyl group, an ethyl group, a propyl group, a butyl group, and a pentyl group can be exemplified. The alkyl group represented by $R_{201}$, $R_{202}$ and $R_{203}$ is more preferably a straight chain or branched 2-oxoalkyl group, or an alkoxycarbonylmethyl group.

The cycloalkyl group represented by $R_{201}$, $R_{202}$ and $R_{203}$ is preferably a cycloalkyl group having from 3 to 10 carbon atoms, e.g., a cyclopentyl group, a cyclohexyl group and a norbonyl group can be exemplified. The cycloalkyl group represented by $R_{201}$, $R_{202}$ and $R_{203}$ is more preferably a cyclic 2-oxoalkyl group.

The 2-oxoalkyl group represented by $R_{201}$, $R_{202}$ and $R_{203}$ may be any of straight chain, branched and cyclic, and preferably a group having >C=O on the 2-position of the above alkyl group or cycloalkyl group can be exemplified.

As the alkoxyl group in the alkoxycarbonylmethyl group represented by $R_{201}$, $R_{202}$ and $R_{203}$, preferably an alkoxyl group having from 1 to 5 carbon atoms, e.g., a methoxy group, an ethoxy group, a propoxy group, a butoxy group, and a pentoxy group can be exemplified.

$R_{201}$, $R_{202}$ and $R_{203}$ may further be substituted with a halogen atom, an alkoxyl group (e.g., having from 1 to 5 carbon atoms), a hydroxyl group, a cyano group, or a nitro group.

Compound (ZI-3a) is a compound represented by the following formula (ZI-3a) having a phenacylsulfonium salt structure.

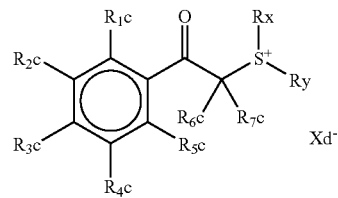

(ZI-3a)

In formula (ZI-3a), $R_{1c}$, $R_{2c}$, $R_{3c}$, $R_{4c}$ and $R_{5c}$ each represents a hydrogen atom, an alkyl group, a cycloalkyl group, an alkoxy group, or a halogen atom.

$R_{6c}$ and $R_{7c}$ each represents a hydrogen atom, an alkyl group or a cycloalkyl group.

$R_x$ and $R_y$ each represents an alkyl group, a cycloalkyl group, an allyl group, or a vinyl group.

Any two or more of $R_{1c}$ to $R_{7c}$, and $R_x$ and $R_y$ may be bonded to each other to form cyclic structures, respectively, and the cyclic structures may contain an oxygen atom, a sulfur atom, an ester bond, or an amido bond. As the groups formed by any two or more of $R_{1c}$ to $R_{7c}$, and $R_x$ and $R_y$, by bonding, a butylene group, a pentylene group, etc., can be exemplified.

$Xd^-$ represents an anion of an acid represented by formula (I).

The alkyl group represented by $R_{1c}$ to $R_{7c}$ may be either straight chain or branched, e.g., an alkyl group having from 1 to 20 carbon atoms, and preferably a straight chain or branched alkyl group having from 1 to 12 carbon atoms, e.g., a methyl group, an ethyl group, a straight chain or branched propyl group, a straight chain or branched butyl group, and a straight chain or branched pentyl group can be exemplified.

As the cycloalkyl group represented by $R_{1c}$ to $R_{7c}$, a cycloalkyl group having from 3 to 8 carbon atoms, e.g., a cyclopentyl group and a cyclohexyl group can be exemplified.

The alkoxyl group represented by $R_{1c}$ to $R_{5c}$ may be any of straight chain, branched, and cyclic, e.g., an alkoxyl group having from 1 to 10 carbon atoms, and preferably a straight chain or branched alkoxyl group having from 1 to 5 carbon atoms (e.g., a methoxy group, an ethoxy group, a straight chain or branched propoxy group, a straight chain or branched butoxy group, and a straight chain or branched pentoxy group), a cyclic alkoxyl group having from 3 to 8 carbon atoms (e.g., a cyclopentyloxy group, and a cyclohexyloxy group) can be exemplified.

Preferably any of $R_{1c}$ to $R_{5c}$ represents a straight chain or branched alkyl group, a cycloalkyl group, or a straight chain, branched, or cyclic alkoxyl group, and more preferably the sum total of the carbon atoms of $R_{1c}$ to $R_{5c}$ is from 2 to 15. By selecting such substituents, the solubility in a solvent is bettered and the generation of particles during preservation can be restrained.

As the alkyl groups represented by $R_x$ and $R_y$, the same alkyl groups as represented by $R_{1c}$ to $R_{7c}$ can be exemplified. The alkyl group represented by $R_x$ and $R_y$ is more preferably a straight chain or branched 2-oxoalkyl group or an alkoxycarbonyl group.

As the cycloalkyl group represented by $R_x$ and $R_y$, the same cycloalkyl group as represented by $R_{1c}$ to $R_{7c}$ can be exemplified. The cycloalkyl group represented by $R_x$ and $R_y$ is preferably a cyclic 2-oxoalkyl group.

As the straight chain, branched, or cyclic 2-oxoalkyl group, a group having >C=O on the 2-position of the alkyl group or the cycloalkyl group represented by $R_{1c}$ to $R_{7c}$ can be exemplified.

As the alkoxyl group in the alkoxycarbonylmethyl group, the same alkoxyl group as represented by $R_{1c}$ to $R_{5c}$ can be exemplified.

$R_x$ and $R_y$ each preferably represents an alkyl group having 4 or more carbon atoms, more preferably 6 or more carbon atoms, and still more preferably an alkyl group having 8 or more carbon atoms.

In formula (ZIIa), $R_{204}$ and $R_{205}$ each represents an aryl group, an alkyl group, or a cycloalkyl group.

The aryl group represented by $R_{204}$ and $R_{205}$ is preferably a phenyl group or a naphthyl group, and more preferably a phenyl group.

The alkyl group represented by $R_{204}$ and $R_{205}$ may be either straight chain or branched, and preferably a straight chain or branched alkyl group having from 1 to 10 carbon atoms, e.g., a methyl group, an ethyl group, a propyl group, a butyl group, and a pentyl group can be exemplified.

The cycloalkyl group represented by $R_{204}$ and $R_{205}$ is preferably a cycloalkyl group having from 3 to 10 carbon atoms, e.g., a cyclopentyl group, a cyclohexyl group, and a norbonyl group can be exemplified.

As the substituents that $R_{204}$ and $R_{205}$ may have, e.g., an alkyl group (e.g., having from 1 to 15 carbon atoms), a cycloalkyl group (e.g., having from 3 to 15 carbon atoms), an aryl group (e.g., having from 6 to 15 carbon atoms), an alkoxyl group (e.g., having from 1 to 15 carbon atoms), a halogen atom, a hydroxyl group, a phenylthio group, etc., can be exemplified.

The preferred examples of the cationic structures in formulae (ZIa) and (ZIIa) are shown below, but the invention is not restricted thereto.

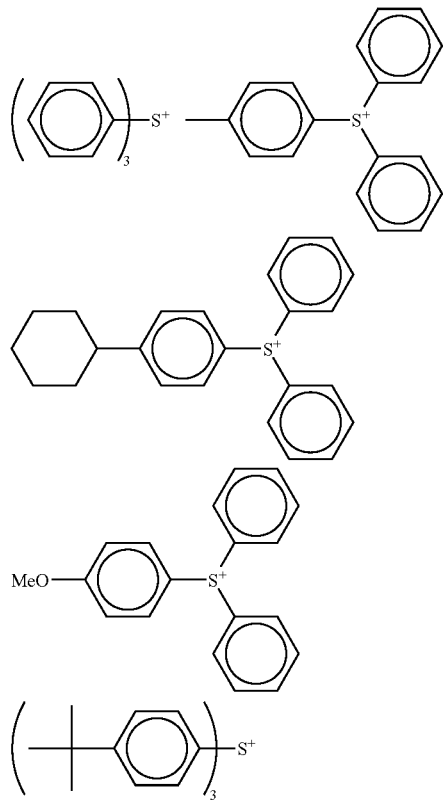

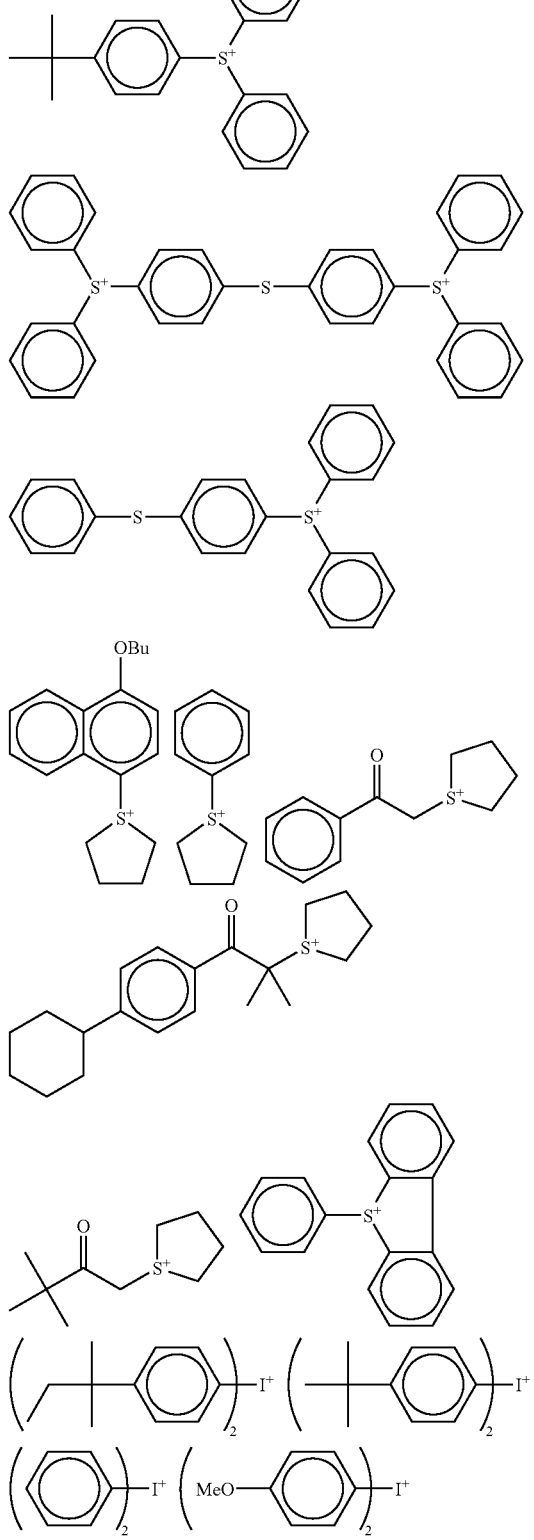

As the preferred specific examples of component (A), arbitrary combinations of the anions of acids shown in the specific examples of the acid represented by formula (I) with the cations shown above can be exemplified.

Component (A) is preferably a compound represented by the following formula (Ia).

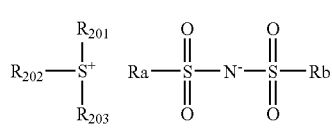

In formula (Ia), $R^{201}$, $R^{202}$ and $R^{203}$ each represents an organic group; Ra represents an alkyl group substituted with a fluorine atom, or an aryl group substituted with a fluorine atom or a group having a fluorine atom; and Rb represents an alkyl group not substituted with a fluorine atom on the α-position, or an aryl group not substituted with a fluorine atom or a group having a fluorine atom.

A representative compound represented by formula (Ia) can be synthesized according to the method, e.g., in the reaction scheme shown below.

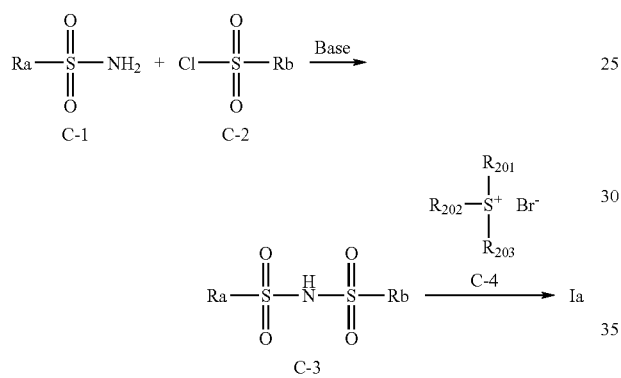

That is, sulfonamide represented by formula (C-1) is reacted with sulfonic acid chloride represented by formula (C-2) in a solvent in the presence of a base to obtain sulfonimide represented by formula (C-3). The solvent used here is not especially restricted but it is preferred to use water. As the base, inorganic and organic bases can be arbitrarily adopted, but inorganic base is preferred. Specifically, alkali metal salts such as sodium hydroxide and potassium hydroxide can be exemplified as especially preferred examples. The reaction temperature is from −20° C. to the boiling point of the solvent, and it is preferred that the reaction is carried out in the range of from ice cooling to 40° C. Subsequently, sulfonimide represented by formula (C-3) is subjected to salt exchange with sulfonium bromide represented by formula (C-4) to thereby obtain the objective compound represented by formula (Ia) of the invention.

The content of component (A) in the composition is preferably from 0.1 to 20 mass % based on all the solids content of the photosensitive composition, more preferably from 0.5 to 10 mass %, still more preferably from 1 to 7 mass %, and especially preferably from 3 to 7 mass %.

The photosensitive composition in the invention may contain a compound capable of generating an acid upon irradiation with actinic ray or radiation other than the compound capable of generating an acid represented by formula (I) upon irradiation with actinic ray or radiation.

As such acid generators, photo-initiators of photo-cationic polymerization, photo-initiators of photo-radical polymerization, photo-decoloring agents and photo-discoloring agents of dyestuffs, well-known compounds capable of generating an acid upon irradiation with actinic ray or radiation that are used in micro-resists and the like, and the mixtures of these compounds can be optionally selected and used.

For example, diazonium salt, phosphonium salt, sulfonium salt, iodonium salt, imidosulfonate, oximesulfonate, diazodisulfone, disulfone, and o-nitrobenzylsulfonate are exemplified as acid generators.

Further, compounds obtained by introducing a group or a compound capable of generating an acid upon irradiation with actinic ray or radiation to the main chain or the side chain of polymers, for example, the compounds disclosed in U.S. Pat. No. 3,849,137, German Patent 3,914,407, JP-A-63-26653, JP-A-55-164824, JP-A-62-69263, JP-A-63-146038, JP-A-63-163452, JP-A-62-153853 and JP-A-63-146029 can be used.

The compounds generating an acid by the action of lights as disclosed in U.S. Pat. No. 3,779,778, EP-126,712, etc., can also be used.

Of the compounds capable of generating an acid upon irradiation with actinic ray or radiation usable in combination (hereinafter also referred to as "acid generators usable in combination"), the compounds represented by any of the following formulae (ZI), (ZII) and (ZIII) can be exemplified as preferred compounds.

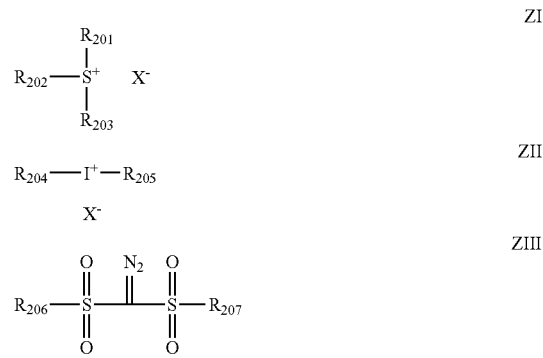

In formula (ZI), $R_{201}$, $R_{202}$ and $R_{203}$ each represents an organic group.

$X^-$ represents a non-nucleophilic anion, preferably a sulfonate anion, a carboxylate anion, a bis(alkylsulfonyl)-amide anion, a tris(alkylsulfonyl)methide anion, $BF_4^-$, $PF_6^-$, $SbF_6^-$, etc., are exemplified, and a preferred anion is an organic anion having a carbon atom.

As preferred organic anions, organic anions represented by any of the following formulae (AN1) to (AN4) are exemplified.

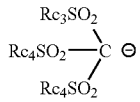

In formulae (AN1) and (AN2), $Rc_1$ represents an organic group.

As the organic group represented by $Rc_1$ in formulae (AN1) and (AN2), an organic group having from 1 to 30 carbon atoms is exemplified, and preferably an alkyl group, a cycloalkyl group, an aryl group, each of which groups may be substituted, and a group obtained by linking a plurality of these groups with a linking group such as a single bond, —O—, —CO$_2$—, —S—, —SO$_3$— or —SO$_2$N(Rd$_1$)— can be exemplified.

$Rd_1$ represents a hydrogen atom or an alkyl group, and $Rd_1$ may form a cyclic structure together with the bonding alkyl group, cycloalkyl group, or aryl group.

The more preferred organic groups represented by $Rc_1$ are an alkyl group substituted with a fluorine atom or a fluoroalkyl group on the 1-position, and a phenyl group substituted with a fluorine atom or a fluoroalkyl group. By the presence of a fluorine atom or a fluoroalkyl group, the acidity of the acid generated with light irradiation increases to enhance sensitivity. When $Rc_1$ has 5 or more carbon atoms, at least one carbon atom is preferably such that a part of hydrogen atoms remains not all the hydrogen atoms are substituted with fluorine atoms, and it is more preferred that the number of hydrogen atoms is larger than the number of fluorine atoms. Not containing a perfluoroalkyl group having 5 or more carbon atoms contributes to the reduction of toxicity to ecosystem.

As an especially preferred embodiment of $Rc_1$, a group represented by the following formula can be exemplified.

In the above formula, $Rc_6$ represents a perfluoroalkylene group having preferably 4 or less carbon atoms, more preferably from 2 to 4, and still more preferably from 2 or 3 carbon atoms, or a phenylene group substituted with from 3 to 5 fluorine atoms and/or from 1 to 3 fluoroalkyl groups.

Ax represents a single bond, or a divalent linking group (preferably —O—, —CO$_2$—, —S—, —SO$_3$— or —SO$_2$N(Rd$_1$)-). $Rd_1$ represents a hydrogen atom or an alkyl group, and may be bonded to $Rc_7$ to form a cyclic structure.

$Rc_7$ represents a hydrogen atom, a fluorine atom, a straight chain or branched alkyl group, a monocyclic or polycyclic cycloalkyl group, or an aryl group. It is preferred that the alkyl group, cycloalkyl group and aryl group do not have a fluorine atom as a substituent.

In formulae (AN3) and (AN4), $Rc_3$, $Rc_4$ and $Rc_5$ each represents a perfluoroalkyl group.

$Rc_3$ and $Rc_4$ may be bonded to each other to form a ring.

In formulae (AN3) and (AN4), as the group formed by $Rc_3$ and $Rc_4$ by bonding, an alkylene group and an arylene group are exemplified, and preferably a perfluoroalkylene group having from 2 to 4 carbon atoms is exemplified. By bonding $Rc_3$ and $Rc_4$ to form a ring, the acidity of the acid generated upon light irradiation increases to improve sensitivity.

In formula (ZI), the number of carbon atoms of the organic groups represented by $R_{201}$, $R_{202}$ and $R_{203}$ is generally from 1 to 30, and preferably from 1 to 20.

Any two of $R_{201}$, $R_{202}$ and $R_{203}$ may be bonded to each other to form a cyclic structure, and an oxygen atom, a sulfur atom, an ester bond, an amido bond or a carbonyl group may be contained in the ring. As the group formed by any two of $R_{201}$, $R_{202}$ and $R_{203}$ by bonding, an alkylene group (e.g., a butylene group and a pentylene group) can be exemplified.

As the specific examples of the organic groups represented by $R_{201}$, $R_{202}$ and $R_{203}$, the corresponding groups in compounds (ZI-1), (ZI-2) and (ZI-3) described later can be exemplified.

The compound represented by formula (ZI) may be a compound having a plurality of structures represented by formula (ZI). For instance, compound (ZI) may be a compound having a structure that at least one of $R_{201}$, $R_{202}$ and $R_{203}$ of the compound represented by formula (ZI) is bonded to at least one of $R_{201}$, $R_{202}$ and $R_{203}$ of another compound represented by formula (ZI).

As further preferred component (ZI), the following compounds (ZI-1), (ZI-2) and (ZI-3) can be exemplified.

Compound (ZI-1) is an arylsulfonium compound that at least one of $R_{201}$, $R_{202}$ and $R_{203}$ in formula (ZI) represents an aryl group, that is, a compound having arylsulfonium as a cation.

All of $R_{201}$, $R_{202}$ and $R_{203}$ of the arylsulfonium compound may be aryl groups, or a part of $R_{201}$, $R_{202}$ and $R_{203}$ may be an aryl group and the remainder may be an alkyl group or a cycloalkyl group.

As the arylsulfonium compound, e.g., a triarylsulfonium compound, a diarylalkylsulfonium compound, an aryldialkyl-sulfonium compound, a diarylcycloalkylsulfonium compound, and an aryldicycloalkylsulfonium compound can be exemplified.

As the aryl group of the arylsulfonium compound, an aryl group, e.g., a phenyl group and a naphthyl group, and an aryl group having a hetero atom, e.g., an indole residue and a pyrrole residue are preferred, and a phenyl group and an indole residue are more preferred. When the arylsulfonium compound has two or more aryl groups, these two or more aryl groups may be the same or different.

The alkyl group incorporated into the arylsulfonium compound according to necessity is preferably a straight chain or branched alkyl group having from 1 to 15 carbon atoms, e.g., a methyl group, an ethyl group, a propyl group, an n-butyl group, a sec-butyl group, a t-butyl group, etc., can be exemplified.

The cycloalkyl group incorporated into the arylsulfonium compound according to necessity is preferably a cycloalkyl group having from 3 to 15 carbon atoms, e.g., a cyclopropyl group, a cyclobutyl group, a cyclohexyl group, etc., can be exemplified.

The aryl group, alkyl group and cycloalkyl group represented by $R_{201}$, $R_{202}$ and $R_{203}$ may have a substituent, e.g., an alkyl group (e.g., having from 1 to 15 carbon atoms), a cycloalkyl group (e.g., having from 3 to 15 carbon atoms), an aryl group (e.g., having from 6 to 14 carbon atoms), an alkoxyl group (e.g., having from 1 to 15 carbon atoms), a halogen atom, a hydroxyl group, and a phenylthio group are exemplified as the substituents. The preferred substituents are a straight chain or branched alkyl group having from 1 to 12 carbon atoms, a cycloalkyl group having from 3 to 12 carbon atoms, and a straight chain, branched, or cyclic alkoxyl group having from 1 to 12 carbon atoms, and more preferred substituents are an alkyl group having from 1 to 4 carbon atoms, and an alkoxyl group having from 1 to 4 carbon atoms. The substituent may be substituted on any one of three of $R_{201}$, $R_{202}$ and $R_{203}$, or may be substituted on all of the three. When $R_{201}$, $R_{202}$ and $R_{203}$ each represents an aryl group, it is preferred that the substituent be substituted on the p-position of the aryl group.

Compound (ZI-2) is described below.

Compound (ZI-2) is a compound in the case where $R_{201}$, $R_{202}$ and $R_{203}$ in formula (ZI) each represents an organic group not having an aromatic ring. The aromatic ring here also includes an aromatic ring containing a hetero atom.

The organic group not having an aromatic ring represented by $R_{201}$, $R_{202}$ and $R_{203}$ generally has from 1 to 30 carbon atoms, and preferably from 1 to 20 carbon atoms.

The organic group not having an aromatic ring represented by $R_{201}$, $R_{202}$ and $R_{203}$ is preferably an alkyl group, a cycloalkyl group, an allyl group, or a vinyl group, more preferably a straight chain, branched or cyclic 2-oxoalkyl group, or an alkoxycarbonylmethyl group, and still more preferably a straight chain or branched 2-oxoalkyl group.

The alkyl group represented by $R_{201}$, $R_{202}$ and $R_{203}$ may be either straight chain or branched, and preferably a straight chain or branched alkyl group having from 1 to 10 carbon atoms, e.g., a methyl group, an ethyl group, a propyl group, a butyl group, and a pentyl group can be exemplified. The alkyl group represented by $R_{201}$, $R_{202}$ and $R_{203}$ is more preferably a straight chain or branched 2-oxoalkyl group, or an alkoxycarbonylmethyl group.

The cycloalkyl group represented by $R_{201}$, $R_{202}$ and $R_{203}$ is preferably a cycloalkyl group having from 3 to 10 carbon atoms, e.g., a cyclopentyl group, a cyclohexyl group, and a norbonyl group can be exemplified. The cycloalkyl group represented by $R_{201}$, $R_{202}$ and $R_{203}$ is more preferably a cyclic 2-oxoalkyl group.

The 2-oxoalkyl group represented by $R_{201}$, $R_{202}$ and $R_{203}$ may be any of straight chain, branched and cyclic, and preferably a group having >C=O on the 2-position of the above alkyl group or cycloalkyl group can be exemplified.

As the alkoxyl group in the alkoxycarbonylmethyl group represented by $R_{201}$, $R_{202}$ and $R_{203}$, preferably an alkoxyl group having from 1 to 5 carbon atoms, e.g., a methoxy group, an ethoxy group, a propoxy group, a butoxy group, and a pentoxy group can be exemplified.

$R_{201}$, $R_{202}$ and $R_{203}$ may further be substituted with a halogen atom, an alkoxyl group (e.g., having from 1 to 5 carbon atoms), a hydroxyl group, a cyano group, or a nitro group.

Compound (ZI-3) is a compound represented by the following formula (ZI-3) and has a phenacylsulfonium salt structure.

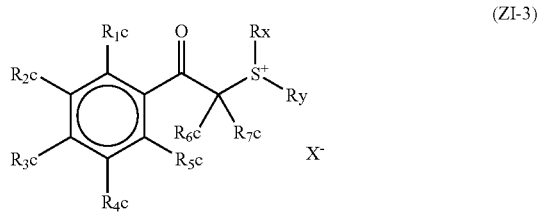

(ZI-3)

In formula (ZI-3), $R_{1c}$, $R_{2c}$, $R_{3c}$, $R_{4c}$ and $R_{5c}$ each represents a hydrogen atom, an alkyl group, a cycloalkyl group, an alkoxyl group, or a halogen atom.

$R_{6c}$ and $R_{7c}$ each represents a hydrogen atom, an alkyl group or a cycloalkyl group.

$R_x$ and $R_y$ each represents an alkyl group, a cycloalkyl group, an allyl group, or a vinyl group.

Any two or more of $R_{1c}$ to $R_{7c}$, and $R_x$ and $R_y$ may be bonded to each other to form cyclic structures, respectively, and the cyclic structures may contain an oxygen atom, a sulfur atom, an ester bond, or an amido bond. As the groups formed by any two or more of $R_{1c}$ to $R_{7c}$, and $R_x$ and $R_y$, by bonding, a butylene group, a pentylene group, etc., can be exemplified.

$X^-$ represents a non-nucleophilic anion, and the same anions as in the non-nucleophilic anion represented by $X^-$ in formula (ZI) can be exemplified.

The alkyl group represented by $R_{1c}$ to $R_{7c}$ may be either straight chain or branched, e.g., an alkyl group having from 1 to 20 carbon atoms, and preferably a straight chain or branched alkyl group having from 1 to 12 carbon atoms, e.g., a methyl group, an ethyl group, a straight chain or branched propyl group, a straight chain or branched butyl group, and a straight chain or branched pentyl group can be exemplified.

As the cycloalkyl group represented by $R_{1c}$ to $R_{7c}$, a cycloalkyl group having from 3 to 8 carbon atoms, e.g., a cyclopentyl group and a cyclohexyl group can be exemplified.

The alkoxyl group represented by $R_{1c}$ to $R_{5c}$ may be any of straight chain, branched, and cyclic, e.g., an alkoxyl group having from 1 to 10 carbon atoms, and preferably a straight chain or branched alkoxyl group having from 1 to 5 carbon atoms (e.g., a methoxy group, an ethoxy group, a straight chain or branched propoxy group, a straight chain or branched butoxy group, and a straight chain or branched pentoxy group), a cyclic alkoxyl group having from 3 to 8 carbon atoms (e.g., a cyclopentyloxy group, and a cyclohexyloxy group) can be exemplified.

It is preferred that any of $R_{1c}$ to $R_{5c}$ represents a straight chain or branched alkyl group, cycloalkyl group, or a straight chain, branched, or cyclic alkoxyl group, and more preferably the sum total of the carbon atoms of $R_{1c}$ to $R_{5c}$ is from 2 to 15, by which the solubility in a solvent is bettered and the generation of particles during preservation can be restrained.

As the alkyl group represented by $R_x$ and $R_y$, the same groups as the alkyl groups represented by $R_{1c}$ to $R_{7c}$ can be exemplified. The alkyl group represented by $R_x$ and $R_y$ is more preferably a straight chain or branched 2-oxoalkyl group or an alkoxycarbonylmethyl group.

As the cycloalkyl group represented by $R_x$ and $R_y$, the same groups as the cycloalkyl groups represented by $R_{1c}$ to $R_{7c}$ can be exemplified. The cycloalkyl group represented by $R_x$ and $R_y$ is more preferably a cyclic 2-oxoalkyl group.

As the straight chain, branched, or cyclic 2-oxoalkyl group, a group having >C=O on the 2-position of the alkyl group or the cycloalkyl group represented by $R_{1c}$ to $R_{7c}$ can be exemplified.

As the alkoxyl group in the alkoxycarbonylmethyl group, the same groups as the alkoxyl groups represented by $R_{1c}$ to $R_{5c}$ can be exemplified.

$R_x$ and $R_y$ each preferably represents an alkyl group having 4 or more carbon atoms, more preferably 6 or more carbon atoms, and still more preferably an alkyl group having 8 or more carbon atoms.

In formulae (ZII) and (ZIII), $R_{204}$, $R_{205}$, $R_{206}$ and $R_{207}$ each represents an aryl group, an alkyl group, or a cycloalkyl group.

$X^-$ represents a non-nucleophilic anion, and the same anion as in the non-nucleophilic anion represented by $X^-$ in formula (ZI) can be exemplified.

The aryl group represented by $R_{204}$ to $R_{207}$ is preferably a phenyl group or a naphthyl group, and more preferably a phenyl group.

The alkyl group represented by $R_{204}$ to $R_{207}$ may be either straight chain or branched, and preferably a straight chain or branched alkyl group having from 1 to 10 carbon atoms, e.g., a methyl group, an ethyl group, a propyl group, a butyl group, and a pentyl group can be exemplified.

The cycloalkyl group represented by $R_{204}$ to $R_{207}$ is preferably a cycloalkyl group having from 3 to 10 carbon atoms, e.g., a cyclopentyl group, a cyclohexyl group, and a norbonyl group can be exemplified.

As the examples of the substituents that $R_{204}$ to $R_{207}$ may have, e.g., an alkyl group (e.g., having from 1 to 15 carbon atoms), a cycloalkyl group (e.g., having from 3 to 15 carbon atoms), an aryl group (e.g., having from 6 to 15 carbon atoms), an alkoxyl group (e.g., having from 1 to 15 carbon atoms), a halogen atom, a hydroxyl group, a phenylthio group, etc., can be exemplified.

Of the compounds capable of generating an acid upon irradiation with actinic ray or radiation that can be used in combination, the compound represented by the following formula (ZIV), (ZV) or (ZVI) can further be exemplified as preferred compounds.

$$Ar_3\text{—}SO_2\text{—}SO_2\text{—}Ar_4 \quad \text{ZIV}$$

$$R_{208}\text{—}SO_2\text{—}O\text{—}N\underset{\substack{\| \\ O}}{\overset{\substack{O \\ \|}}{\diagup\diagdown}}A \quad \text{ZV}$$

$$\underset{R_{210}}{\overset{R_{209}}{\diagdown}}\!\!\!C\!\!=\!\!N\text{—}O\text{—}SO_2\text{—}R_{208} \quad \text{ZVI}$$

In formulae (ZIV) to (ZVI), $Ar_3$ and $Ar_4$ each represents an aryl group.

$R_{208}$ represents an alkyl group, a cycloalkyl group, or an aryl group.

$R_{209}$ and $R_{210}$ each represents an alkyl group, a cycloalkyl group, an aryl group, or an electron attracting group. $R_{209}$ preferably represents an aryl group. $R_{210}$ preferably represents an electron attracting group, and more preferably a cyano group or a fluoroalkyl group.

A represents an alkylene group, an alkenylene group, or an arylene group.

Of the compounds capable of generating an acid upon irradiation with actinic ray or radiation, a compound represented by any of formulae (ZI), (ZII) and (ZIII) is more preferred, a compound represented by formula (ZI) is still more preferred, and a compound represented by any of formulae (ZI-1) to (ZI-3) is still yet preferred.

Moreover, a compound capable of generating an acid upon irradiation with actinic ray or radiation represented by any of the following formulae (AC1) to (AC3) is preferred.

$$Rc_1\text{—}SO_3H \quad \text{AC1}$$

$$\underset{Rc_4SO_2}{\overset{Rc_3SO_2}{\diagdown}}\!\!\!NH \quad \text{AC2}$$

$$\underset{Rc_5SO_2}{\overset{Rc_3SO_2}{\diagdown}}\!\!\!CH\text{—}Rc_4SO_2 \quad \text{AC3}$$

In formulae (AC1) to (AC3), $Rc_1$ represents an organic group.

$Rc_3$, $Rc_4$ and $Rc_5$ each represents a perfluoroalkyl group.

$Rc_3$ and $Rc_4$ may be bonded to each other to form a ring.

That is, as an especially preferred acid generator for use in combination, a compound having a structure represented by formula (ZI) wherein $X^-$ represents an anion of an acid selected from formulae (AN1), (AN2) and (AN3) can be exemplified.

The examples of especially preferred acid generators for use in combination are shown below, however, the invention is not restricted thereto.

(z1) $(\text{Ph})_3\text{S}^+ \; CF_3SO_3^-$ (z2) $(\text{Ph})_3\text{S}^+ \; C_4F_9SO_3^-$ (z3) $(\text{Ph})_3\text{S}^+ \; C_8F_{17}SO_3^-$ (z4) $(\text{Ph})_3\text{S}^+ \; C_2F_5SO_3^-$ (z5) $(\text{Ph})_3\text{S}^+ \; C_3F_7SO_3^-$ (z6) $(\text{Ph})_3\text{S}^+ \; C_6F_{13}SO_3^-$ (z7) $(\text{Ph})_3\text{S}^+ \; {}^-O_3S\text{—}(2,4,6\text{-triisopropylphenyl})$ (z8) $(\text{Ph})_3\text{S}^+ \; {}^-O_3S\text{—}(3,5\text{-bis(trifluoromethyl)phenyl})$

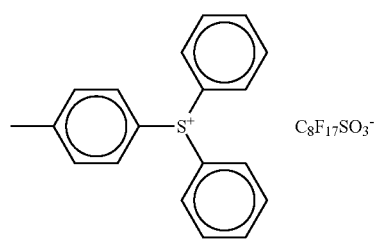 (z9)
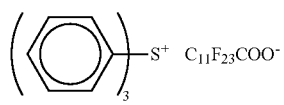 (z10)
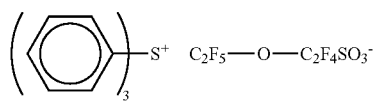 (z11)
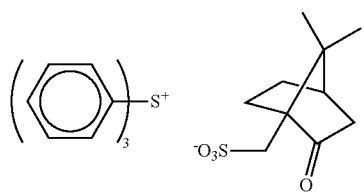 (z12)
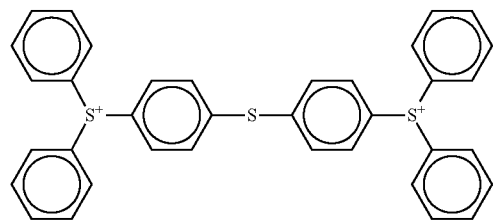 (z13)
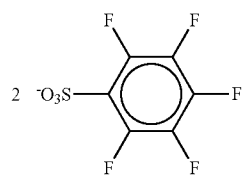 (z14)
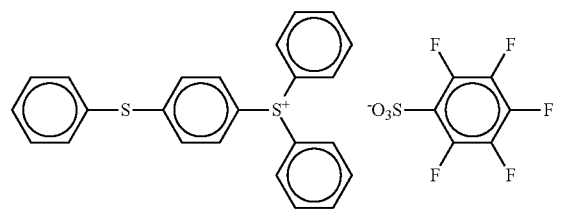 (z15)
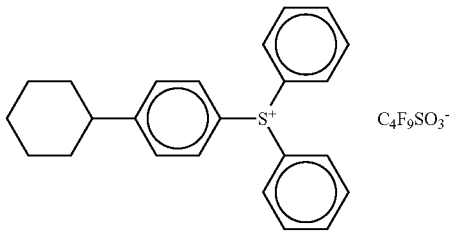 (z16)
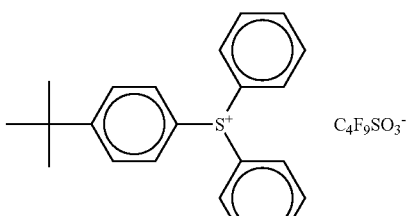 (z17)
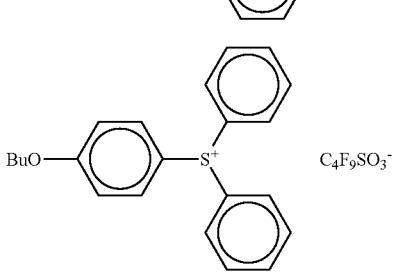 (z18)
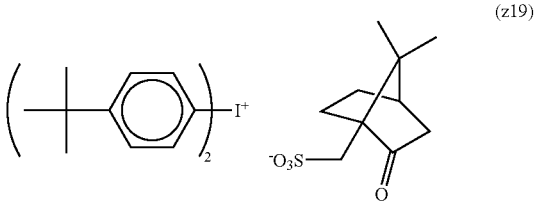 (z19)
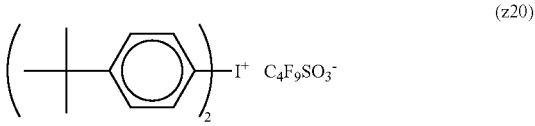 (z20)
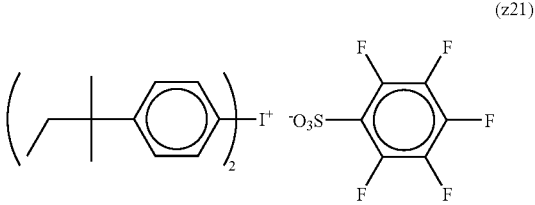 (z21)
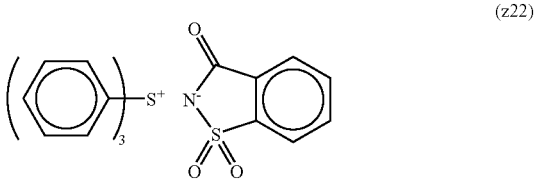 (z22)
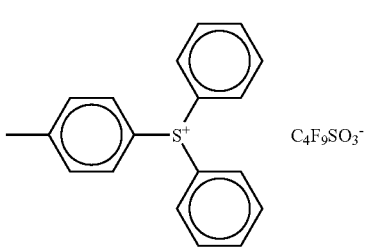 (z23)

(z24)
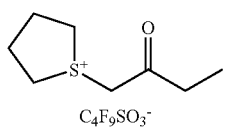
(z25)
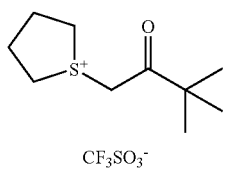
(z26)
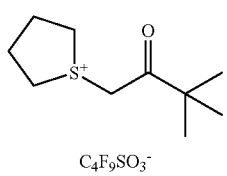
(z27)
(z28)
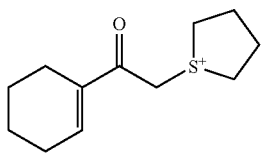
(z29)
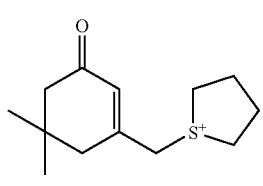
(z30)
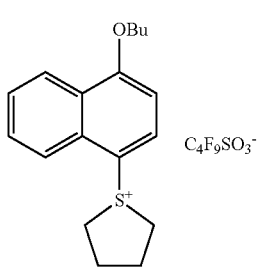
(z31)
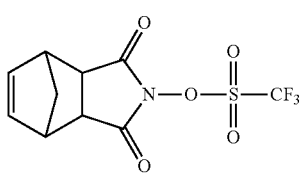
(z32)
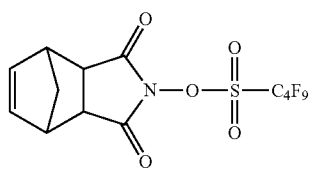
(z33)
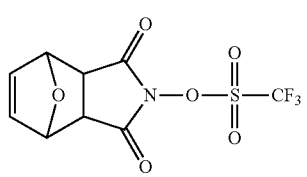
(z34)
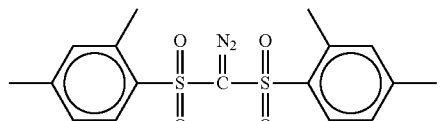
(z35)
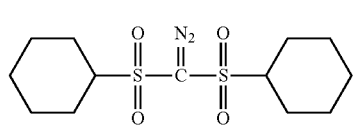
(z36)
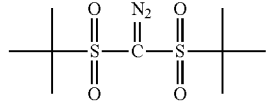
(z37)
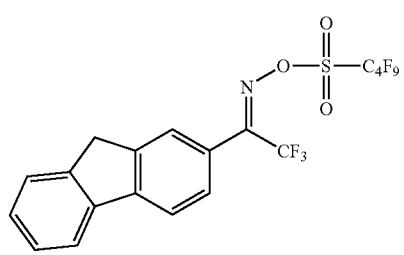
(z38)
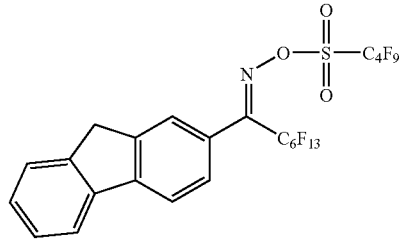
(z39)
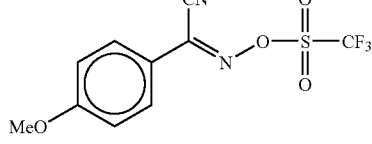
(z40)
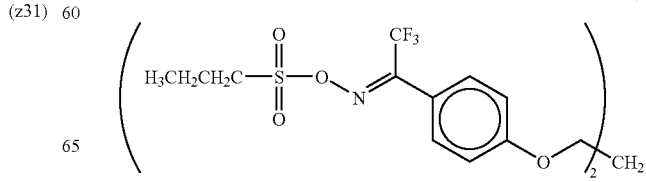

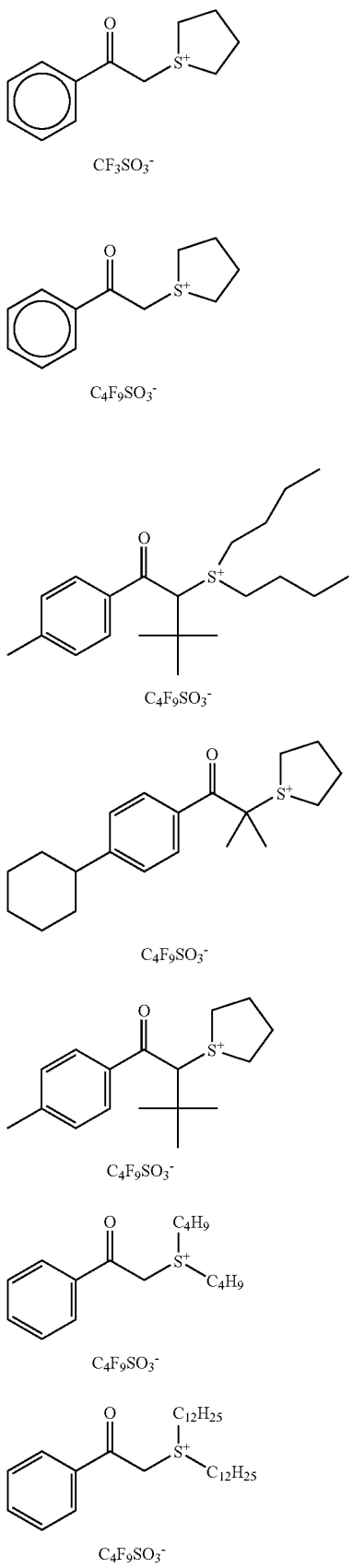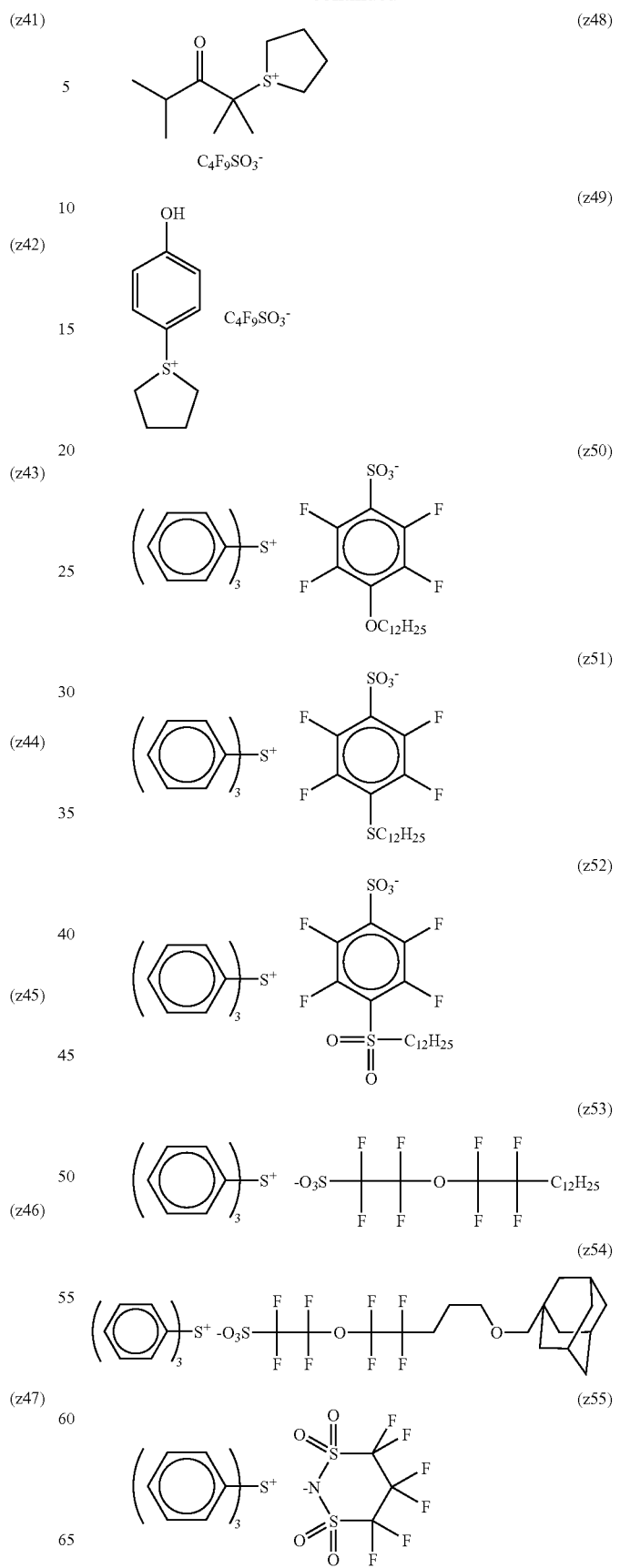

-continued (z56) 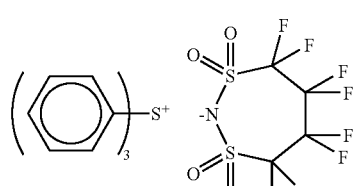

(z57) 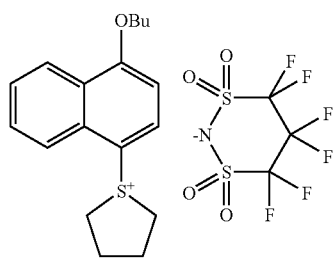

(z58) 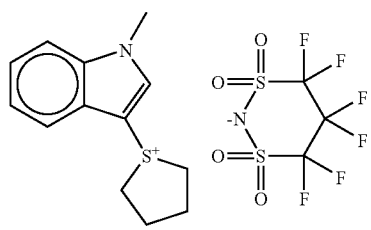

(z59) 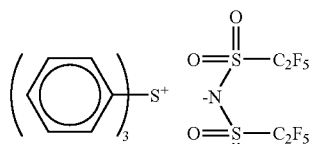

(z60) 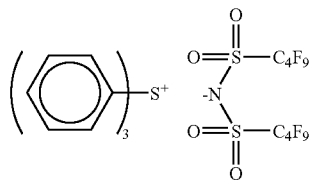

(z61) 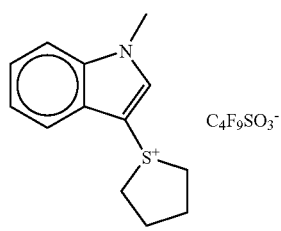

(z62) 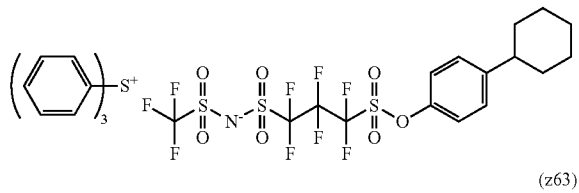

(z63) 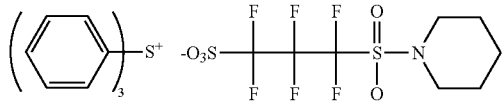

-continued (z64) 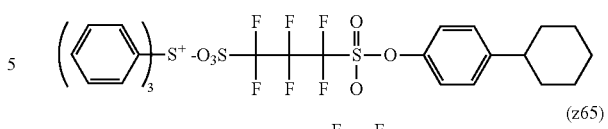

(z65) 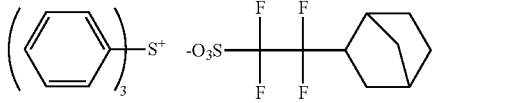

(z66) 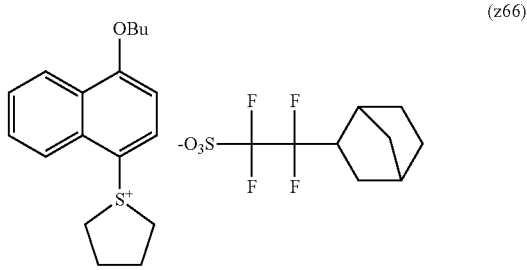

(z67) 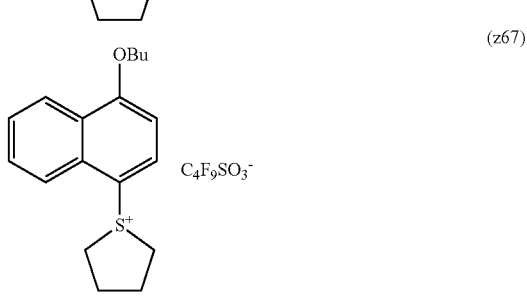

Acid generators for use in combination can be used by one kind alone, or two or more kinds can be used in combination. When two or more compounds are used in combination, it is preferred to combine compounds capable of generating two kinds of organic acids in which the total atom number exclusive of hydrogen atoms differs by 2 or more.

The content of the acid generator for use in combination in a composition is preferably from 0.1 to 20 mass % based on all the solids content of the photosensitive composition, more preferably from 0.5 to 10 mass %, still more preferably from 1 to 7 mass %, and especially preferably from 1 to 4 mass %.

The total content of component (A) and the acid generator for use in combination in a composition is preferably from 0.1 to 20 mass % based on all the solids content of the photosensitive composition, more preferably from 0.5 to 10 mass %, still more preferably from 1 to 7 mass %, and especially preferably from 3 to 7 mass %.

(B) A resin that decomposes by the action of an acid to increase solubility in an alkali developer:

A resin for use in the photosensitive composition in the invention that decomposes by the action of an acid to increase its solubility in an alkali developer (hereinafter also referred to as "a resin of component (B)") is a resin having a group capable of decomposing by the action of an acid (hereinafter also referred to as "an acid- decomposable group") on the main chain or side chain, or both main chain and side chain of the resin. Of these resins, a resin having a group capable of decomposing by the action of an acid on the side chain is more preferred.

The preferred groups decomposable by the action of an acid are groups obtained by substituting the hydrogen atoms of a —COOH group and an —OH group with a group capable of being eliminated by the action of an acid.

As the groups capable of being eliminated by the action of an acid, for example, —C($R_{36}$)($R_{37}$)($R_{38}$), —C($R_{36}$)($R_{37}$)(OR$_{39}$), —C($R_{01}$)($R_{02}$)(OR$_{39}$) and the like can be exemplified.

In the formulae, $R_{36}$ to $R_{39}$ each represents an alkyl group, a cycloalkyl group, an aryl group, an aralkyl group, or an alkenyl group. $R_{36}$ and $R_{37}$ may be bonded to each other to form a ring.

$R_{01}$ and $R_{02}$ each represents a hydrogen atom, an alkyl group, a cycloalkyl group, an aryl group, an aralkyl group, or an alkenyl group.

The preferred acid-decomposable groups in the invention are an acetal group and a tertiary ester group.

The matrix resins in the case where these groups capable of decomposing by the action of an acid are bonded as a side chain are alkali-soluble resins having an —OH or —COOH group on the side chain. For example, alkali-soluble resins described later can be exemplified.

The dissolving rate in alkali of these alkali-soluble resins is preferably 170 Å/sec or more measured in 0.261 N tetramethylammonium hydroxide (TMAH) at 23° C., and especially preferably 330 Å/sec or more.

From such a point of view, especially preferred alkali-soluble resins are alkali-soluble resins having a hydroxystyrene structure, e.g., o-, m-, p-poly(hydroxy-styrene) and copolymers thereof, hydrogenated poly(hydroxy-styrene), halogen- or alkyl-substituted poly(hydroxystyrene), partially O-alkylated or O-acylated products of poly(hydroxy-styrene), a styrene-hydroxystyrene copolymer, an α-methylstyrene-hydroxystyrene copolymer, and a hydrogenated novolak resin, and alkali-soluble resins having a repeating unit having a carboxyl group such as (meth)acrylic acid, and norbornenecarboxylic acid.

As preferred repeating units having an acid-decomposable group in the invention, e.g., t-butoxycarbonyloxystyrene, 1-alkoxyethoxystyrene, and (meth)acrylic acid tertiary alkyl ester can be exemplified, and 2-alkyl-2-adamantyl(meth)acrylate and dialkyl(1-adamantyl)methyl(meth)acrylate are more preferred.

The resin of component (B) for use in the invention can be obtained by reacting an alkali-soluble resin with a precursor of a group capable of decomposing by an acid, or by copolymerizing a monomer to which an acid-decomposable group is bonded with various monomers as disclosed in EP 254,853, JP-A-2-25850, JP-A-3-223860, and JP-A-4-251259.

When the photosensitive composition of the invention is irradiated with KrF excimer laser beams, electron beams, X-rays, or high energy rays having wavelength of 50 nm or less (preferably EUV and the like), it is preferred for the resin of component (B) to have a hydroxystyrene repeating unit. Copolymers having a hydroxystyrene repeating unit and a hydroxystyrene repeating unit protected with an acid-decomposable group, and copolymers having a hydroxystyrene repeating unit and a (meth)acrylate repeating unit protected with an acid-decomposable group are more preferred.

The specific examples of the resins of component (B) for use in the invention are shown below, but the invention is not restricted thereto.

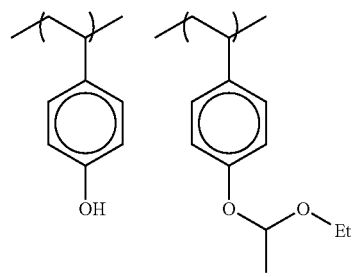

(R-1)

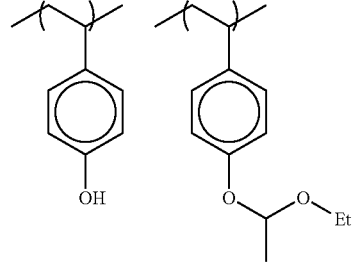

(R-2)

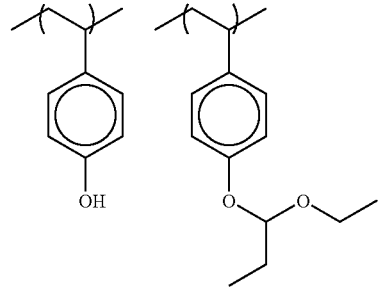

(R-3)

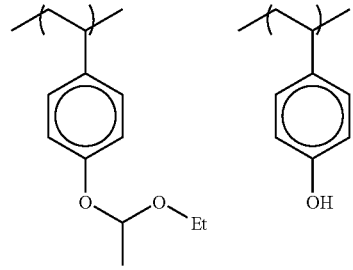

(R-4)

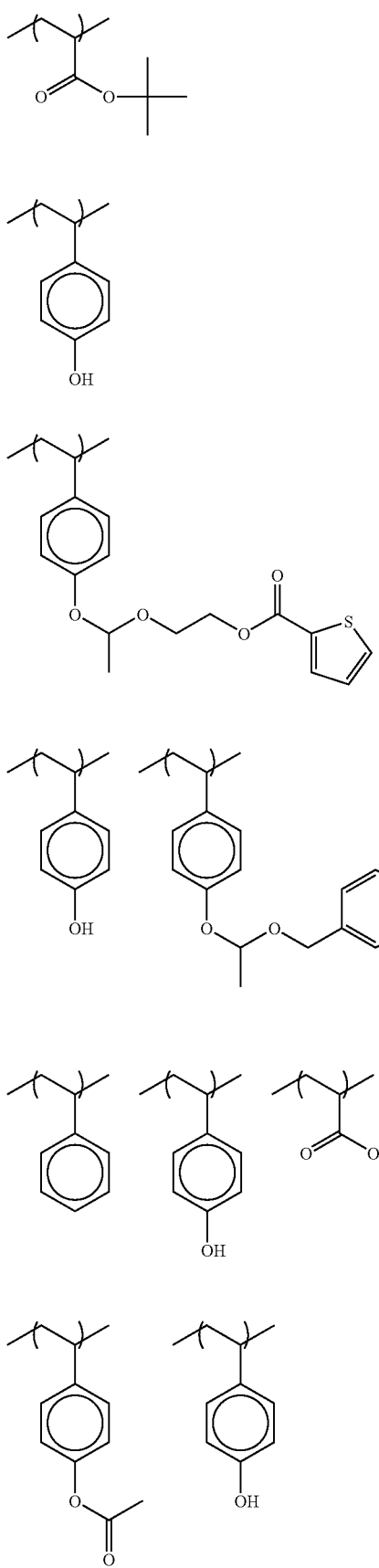
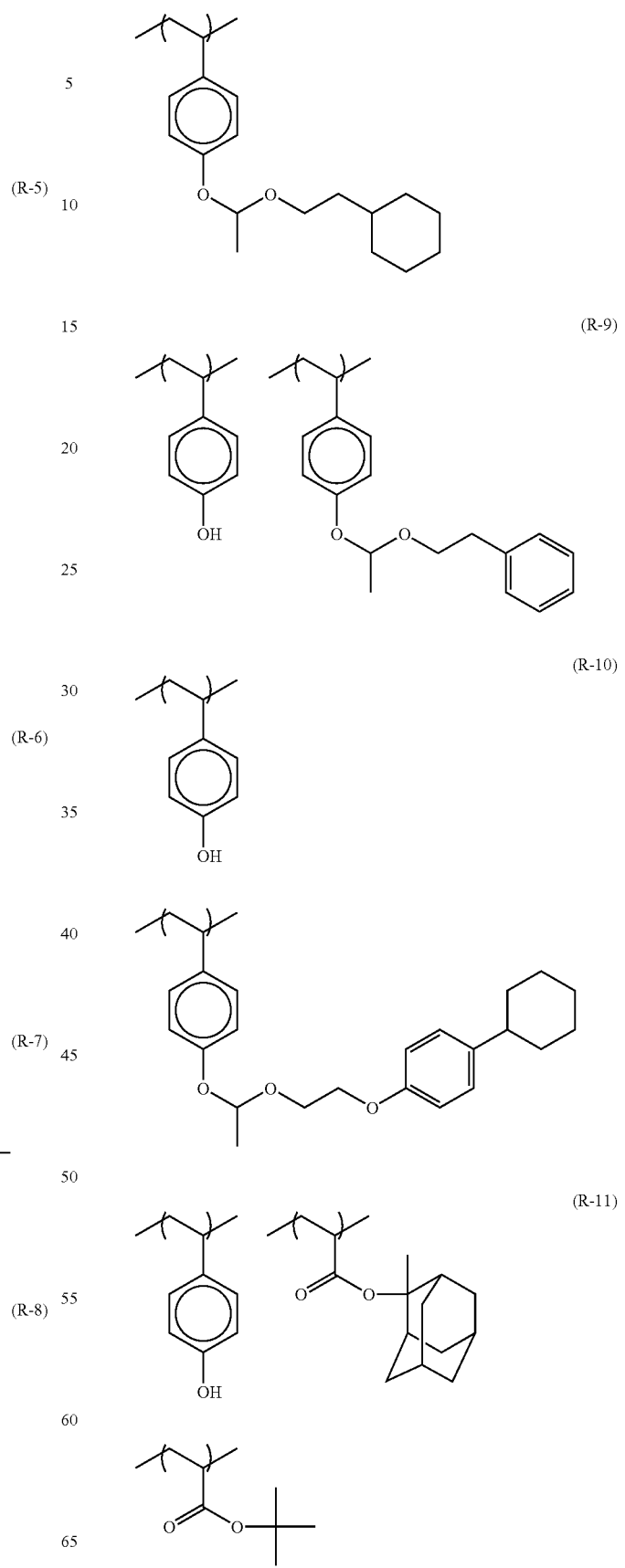

-continued (R-12)
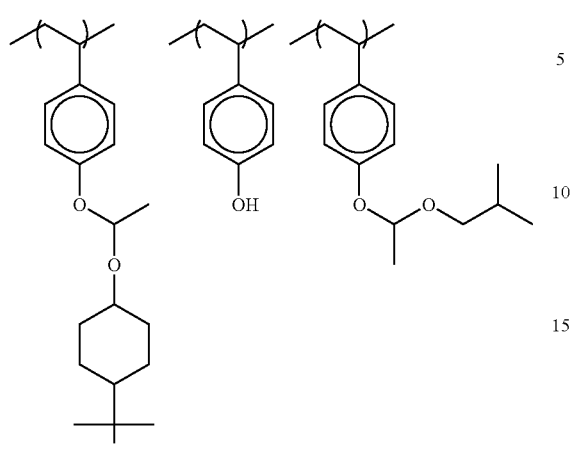

(R-13)
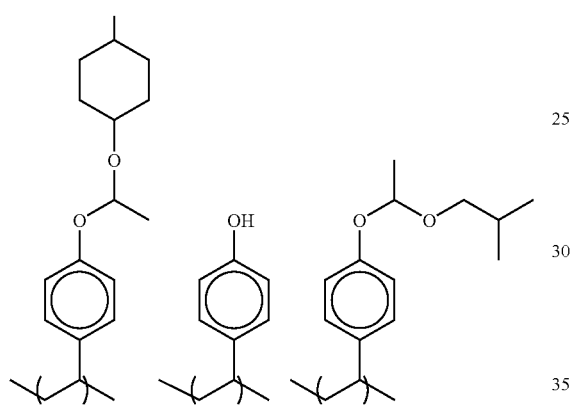

(R-14)
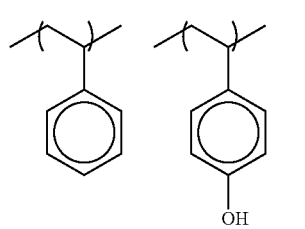

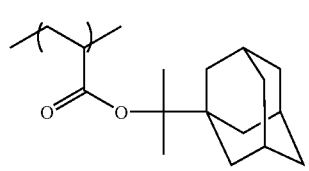

-continued (R-15)
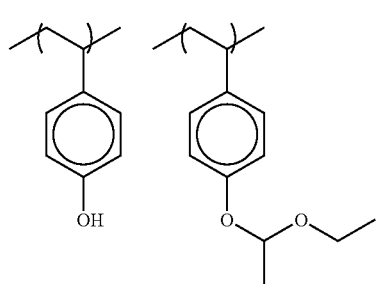

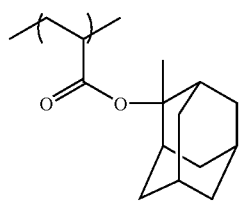

(R-16)
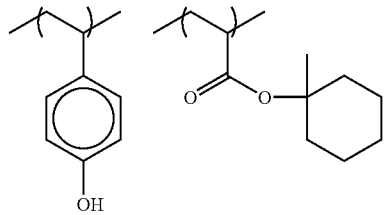

(R-17)

(R-18)
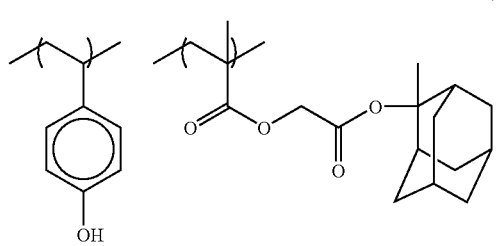

In the above specific examples, tBu represents a t-butyl group.

The content of the group decomposable by the action of an acid is expressed by B/(B+S), taking the number of the acid-decomposable groups in the resin as (B), and the number of alkali-soluble groups not protected with groups capable of elimination by the action of an acid as (S). The content of acid-decomposable group is preferably from 0.01 to 0.7, more preferably from 0.05 to 0.50, and still more preferably from 0.05 to 0.40.

When the photosensitive composition in the invention is irradiated with an ArF excimer laser beam, the resin of component (B) is preferably a resin having a monocyclic or polycyclic alicyclic hydrocarbon structure and decomposed by the action of an acid to increase solubility in an alkali developer.

The resin having a monocyclic or polycyclic alicyclic hydrocarbon structure and decomposed by the action of an acid to increase solubility in an alkali developer (hereinafter also referred to as "an alicyclic hydrocarbon series acid-decomposable resin") is preferably a resin containing at least one repeating unit selected from the group consisting of a repeating unit having a partial structure containing alicyclic hydrocarbon represented by any of the following formulae (pI) to (pV), and a repeating unit represented by the following formula (II-AB).

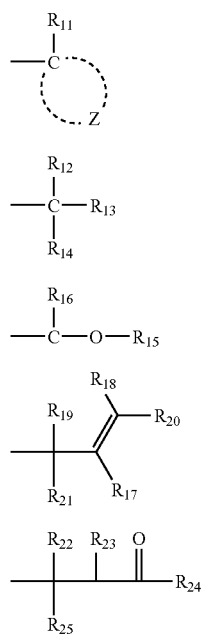

In formulae (pI) to (pV), $R_{11}$ represents a methyl group, an ethyl group, an n-propyl group, an isopropyl group, an n-butyl group, an isobutyl group, or a sec-butyl group.

Z represents an atomic group necessary to form a cycloalkyl group together with a carbon atom.

$R_{12}$, $R_{13}$, $R_{14}$, $R_{15}$ and $R_{16}$ each represents a straight chain or branched alkyl group or cycloalkyl group having from 1 to 4 carbon atoms, but it is preferred that at least one of $R_{12}$ to $R_{14}$, or either $R_{15}$ or $R_{16}$ represents a cycloalkyl group.

$R_{17}$, $R_{18}$, $R_{19}$, $R_{20}$ and $R_{21}$ each represents a hydrogen atom, a straight chain or branched alkyl group or cycloalkyl group having from 1 to 4 carbon atoms, but it is preferred that at least one of $R_{17}$ to $R_{21}$ represents a cycloalkyl group, and either $R_{19}$ or $R_{21}$ represents a straight chain or branched alkyl group or cycloalkyl group having from 1 to 4 carbon atoms.

$R_{22}$, $R_{23}$, $R_{24}$ and $R_{25}$ each represents a hydrogen atom, a straight chain or branched alkyl group or cycloalkyl group having from 1 to 4 carbon atoms, but it is preferred that at least one of $R_{22}$ to $R_{25}$ represents a cycloalkyl group, and $R_{23}$ and $R_{24}$ may be bonded to each other to form a ring.

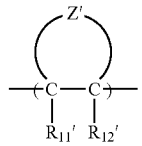

In formula (II-AB), $R_{11}'$ and $R_{12}'$ each represents a hydrogen atom, a cyano group, a halogen atom, or an alkyl group.

Z' contains bonded two carbon atoms (C—C) and represents an atomic group to form an alicyclic structure.

The repeating unit represented by formula (II-AB) is preferably represented by the following formula (II-AB1) or (II-AB2).

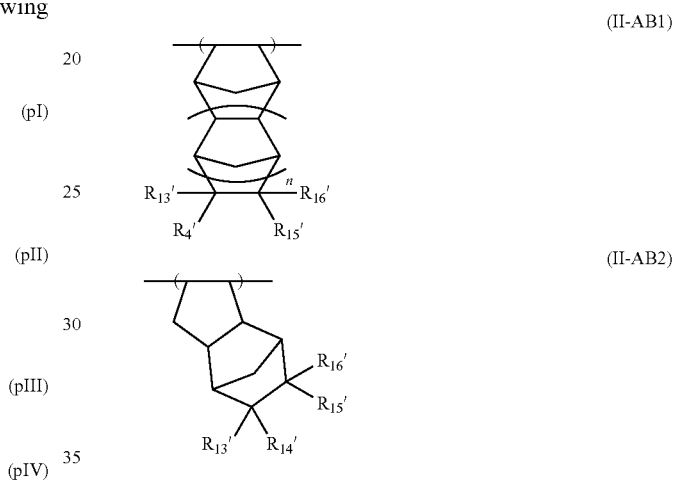

In formulae (II-AB1) and (II-AB2), $R_{13}'$, $R_{14}'$, $R_{15}'$ and $R_{16}'$ each represents a hydrogen atom, a halogen atom, a cyano group, —COOH, —COOR$_5$, a group that decomposes by the action of an acid, —C(=O)—X-A'-R$_{17}'$, an alkyl group, or a cycloalkyl group, and at least two of $R_{13}'$ to $R_{16}'$ may be bonded to form a ring.

$R_5$ represents an alkyl group, a cycloalkyl group, or a group having a lactone structure.

X represents an oxygen atom, a sulfur atom, —NH—, —NHSO$_2$—, or —NHSO$_2$NH—.

A' represents a single bond or a divalent linking group.

$R_{17}'$ represents —COOH, —COOR$_5$, —CN, a hydroxyl group, an alkoxyl group, —CO—NH—R$_6$, —CO—NH—SO$_2$—R$_6$, or a group having a lactone structure.

$R_6$ represents an alkyl group or a cycloalkyl group.

n represents 0 or 1.

In formulae (pI) to (pV), the alkyl group represented by $R_{12}$ to $R_{25}$ is a straight chain or branched alkyl group having from 1 to 4 carbon atoms, and, e.g., a methyl group, an ethyl group, etc., can be exemplified.

The cycloalkyl groups represented by $R_{11}$ to $R_{25}$ or the cycloalkyl groups formed by Z and carbon atoms may be monocyclic or polycyclic. Specifically, groups having a monocyclic, bicyclic, tricyclic or tetracyclic structure having 5 or more carbon atoms can be exemplified. The carbon atom number of these cycloalkyl groups is preferably from 6 to 30, and especially preferably from 7 to 25. These cycloalkyl groups may each have a substituent.

As preferred cycloalkyl groups, an adamantyl group, a noradamantyl group, a decalin residue, a tricyclodecanyl group, a tetracyclododecanyl group, a norbornyl group, a cedrol group, a cyclopentyl group, a cyclohexyl group, a cycloheptyl group, a cyclooctyl group, a cyclodecanyl group, and a cyclododecanyl group can be exemplified. More preferably, an adamantyl group, a norbornyl group, a cyclohexyl group, a cyclopentyl group, a tetracyclododecanyl group, and a tricyclodecanyl group can be exemplified.

As the further substituents of these alkyl groups and cycloalkyl groups, an alkyl group (having from 1 to 4 carbon atoms), a halogen atom, a hydroxyl group, an alkoxyl group (having from 1 to 4 carbon atoms), a carboxyl group, and an alkoxycarbonyl group (having from 2 to 6 carbon atoms) can be exemplified. As the substituents that these alkyl group, alkoxyl group and alkoxycarbonyl group may further have, a hydroxyl group, a halogen atom and an alkoxyl group are exemplified.

The structures represented by formulae (pI) to (pV) in the above resins can be used for the protection of the alkali-soluble groups. As the alkali-soluble groups, various groups known in this technical field can be exemplified.

Specifically, such structures that the hydrogen atoms of a carboxylic acid group, a sulfonic acid group, a phenol group and a thiol group are substituted with the structures represented by formulae (pI) to (pV) are exemplified, and preferably the structures that the hydrogen atoms of a carboxylic acid group and a sulfonic acid group are substituted with the structures represented by formulae (pI) to (pV) are exemplified.

As the repeating unit having the alkali-soluble group protected with the structure represented by any of formulae (pI) to (pV), a repeating unit represented by the following formula (PA) is preferred.

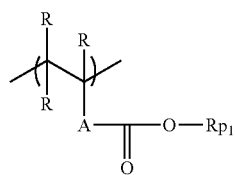

(PA)

In formula (PA), R represents a hydrogen atom, a halogen atom, or a straight chain or branched alkyl group having from 1 to 4 carbon atoms. A plurality of R's may be the same or different.

A represents a single group or a combination of two or more groups selected from the group consisting of a single bond, an alkylene group, an ether group, a thioether group, a carbonyl group, an ester group, an amido group, a sulfonamido group, a urethane group, and a urea group, and preferably a single bond or —COO—CH$_2$—.

Rp$_1$ represents a group represented by any of formulae (pI) to (pV).

The repeating unit represented by formula (PA) is most preferably a repeating unit by 2-alkyl-2-adamantyl(meth)acrylate, or dialkyl(1-adamantyl)methyl(meth)acrylate.

The specific examples of the repeating units represented by formula (PA) are shown below, but the invention is not restricted thereto.

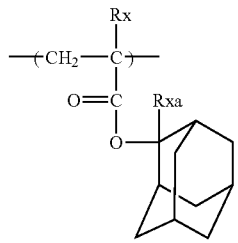

1

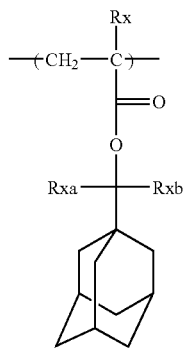

2

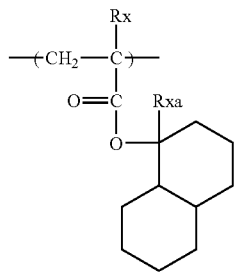

3

4

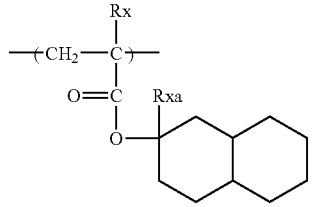

5

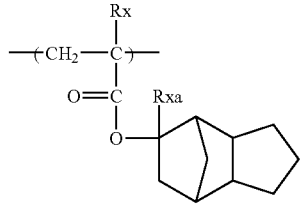

6

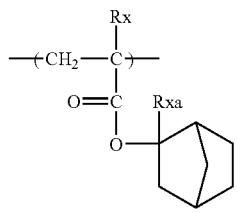

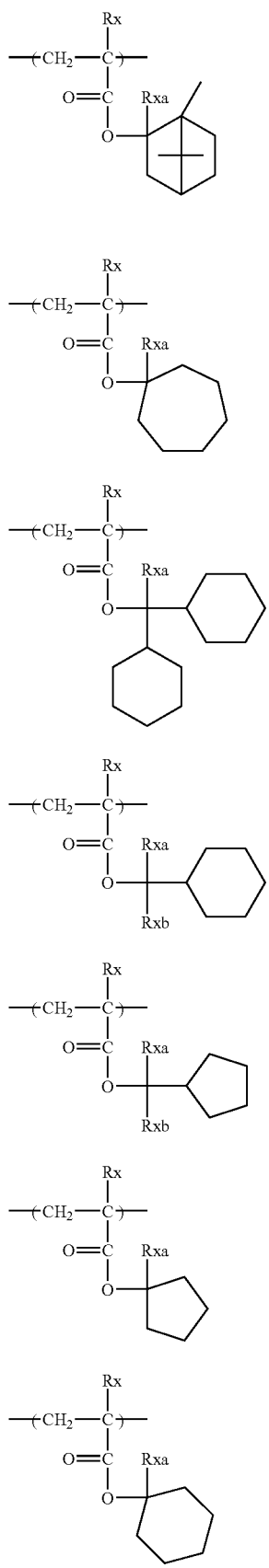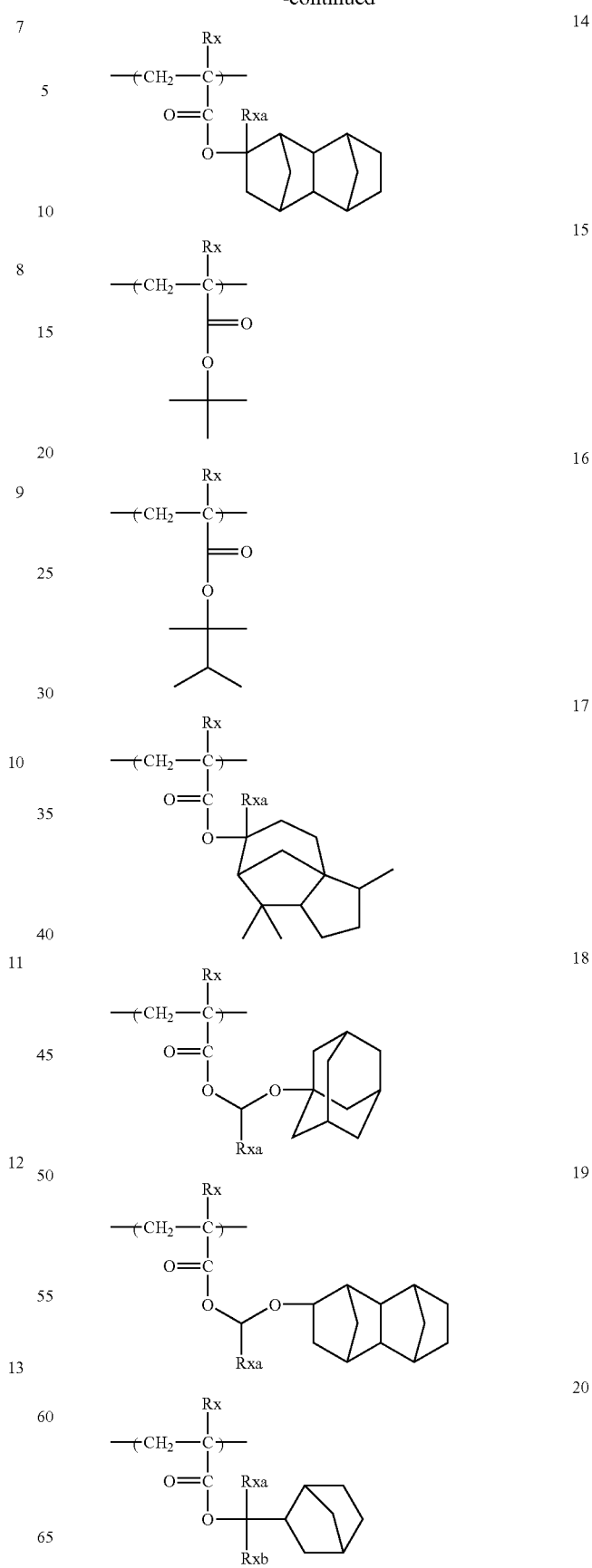

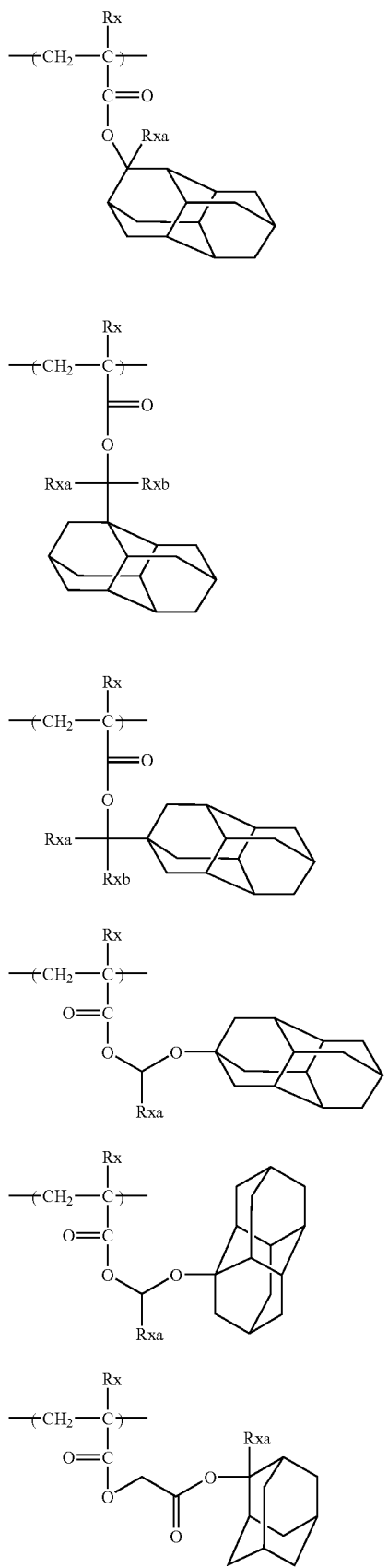

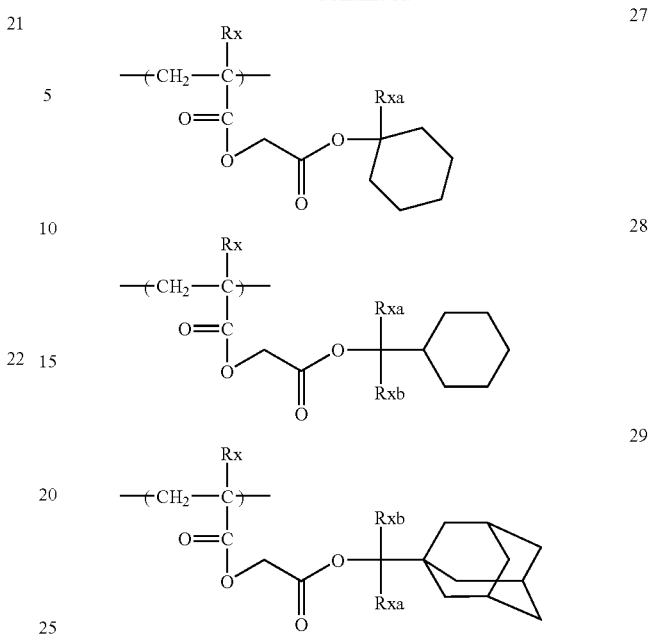

In the above specific examples, Rx represents H, CH₃, CF₃, or CH₂OH, and Rxa and Rxb each represents an alkyl group having from 1 to 4 carbon atoms.

As the halogen atoms represented by $R_{11}'$ and $R_{12}'$ in formula (II-AB), a chlorine atom, a bromine atom, a fluorine atom and an iodine atom are exemplified.

As the alkyl groups represented by $R_{11}'$ and $R_{12}'$, straight chain or branched alkyl groups having from 1 to 10 carbon atoms are exemplified.

The atomic group for forming an alicyclic structure represented by Z' is an atomic group to form a repeating unit of alicyclic hydrocarbon that may have a substituent in the resin, and an atomic group to form a bridged alicyclic structure for forming a bridged alicyclic hydrocarbon repeating unit is especially preferred.

As the skeleton of the alicyclic hydrocarbon formed, the same alicyclic hydrocarbon groups as represented by $R_{12}$ to $R_{25}$ in formulae (pI) to (pV) are exemplified.

The skeleton of the alicyclic hydrocarbon may have a substituent, and as the substituents, the groups represented by $R_{13}'$ to $R_{16}'$ in formula (II-AB1) or (II-AB2) can be exemplified.

In the alicyclic hydrocarbon series acid-decomposable resin in the invention, a group that decomposes by the action of an acid can be contained in at least one repeating unit of the repeating unit having a partial structure containing the alicyclic hydrocarbon represented by any of formulae (pI) to (pV), the repeating unit represented by formula (II-AB), and a repeating unit of the later-described copolymer component.

The acid-decomposable repeating unit may be used by one kind alone, but it is preferred to use two or more kinds of acid-decomposable repeating units different in the number of carbon atoms of acid-elimination groups in combination, by which the balance of resolution and exposure latitude is bettered.

Various substituents of $R_{13}'$ to $R_{16}'$ in formula (II-AB1) or (II-AB2) can also be the substituents of the atomic group to form an alicyclic structure, or atomic group Z' to form a bridged alicyclic structure in formula (II-AB).

The specific examples of the repeating units represented by formula (II-AB1) or (II-AB2) are shown below, but the invention is not restricted to these specific examples.
[II-1]
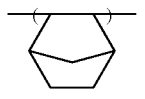
[II-2]
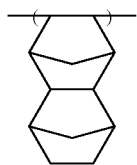
[II-3]
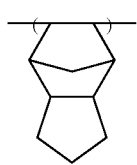
[II-4]
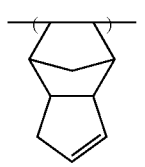
[II-5]
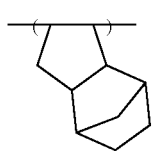
[II-6]
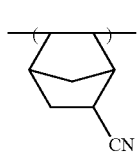
[II-7]
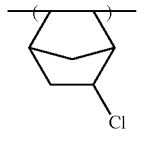
[II-8]
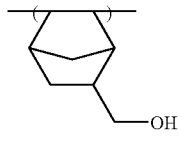
[II-9]
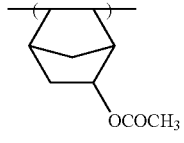
[II-10]
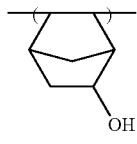
-continued
[II-11]
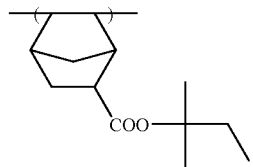
[II-12]
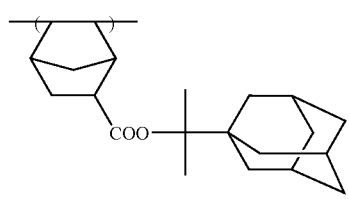
[II-13]
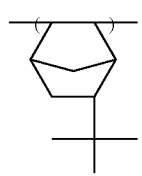
[II-14]
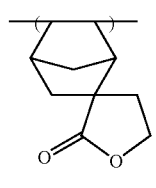
[II-15]
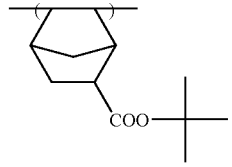
[II-16]
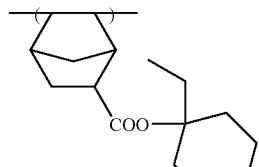
[II-17]
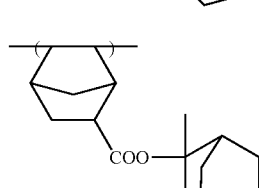
[II-18]
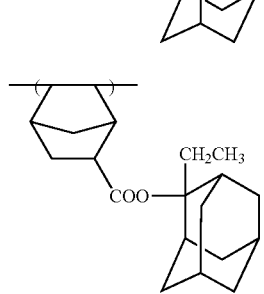

[II-19] 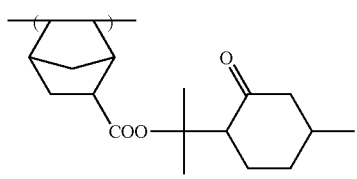
[II-20] 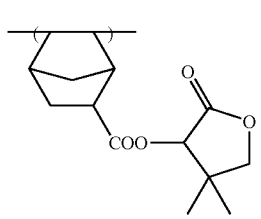
[II-21] 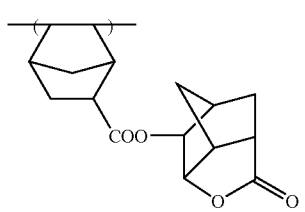
[II-22] 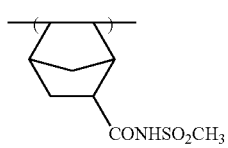
[II-23] 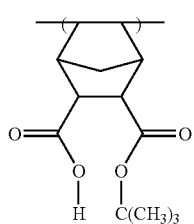
[II-24] 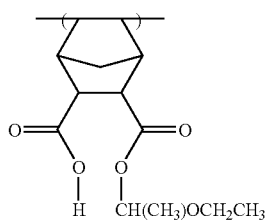
[II-25] 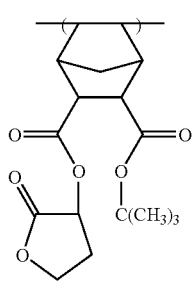
[II-26] 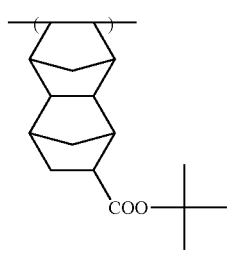
[II-27] 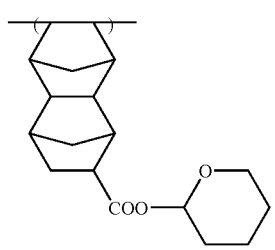
[II-28] 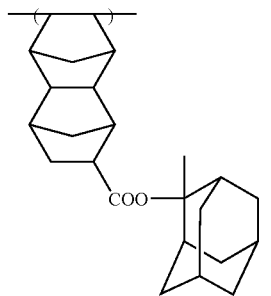
[II-29] 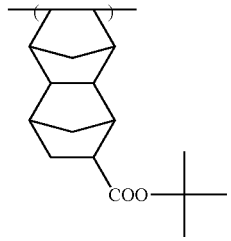
[II-30] 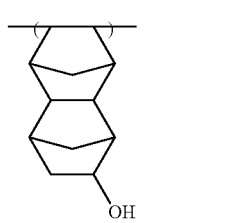
[II-31] 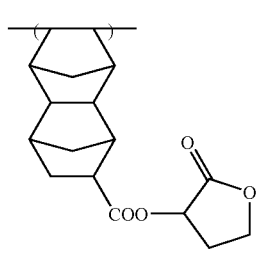

[II-32]

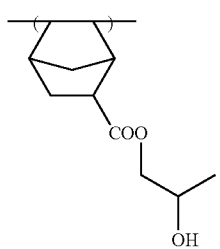

It is preferred for alicyclic hydrocarbon series acid-decomposable resin in the invention to have a lactone group. As the lactone group, any group can be used so long as the group has a lactone structure, but groups having a 5- to 7-membered ring lactone structure are preferably used, and groups having a 5- to 7-membered ring lactone structure condensed with other ring structures in the form of forming a bicyclo structure or a spiro structure are preferred. It is more preferred to contain a repeating unit having a group having a lactone structure represented by any of the following formulae (LC1-1) to (LC1-16). A group having a lactone structure may be directly bonded to the main chain of a repeating unit. Preferred lactone structures are (LC1-1), (LC1-4), (LC1-5), (LC1-6), (LC1-13) and (LC1-14). By the use of a specific lactone structure, line edge roughness and development defect are bettered.

LC1-1

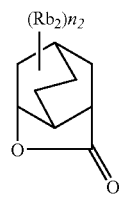

LC1-2

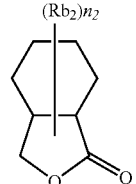

LC1-3

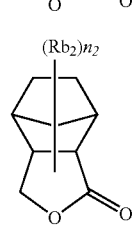

LC1-4

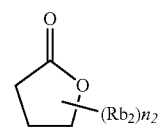

LC1-5

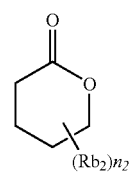

LC1-6

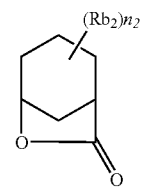

LC1-7

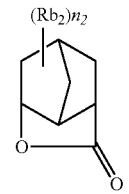

LC1-8

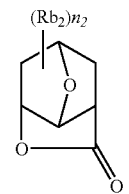

LC1-9

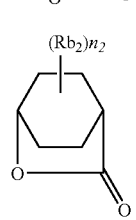

LC1-10

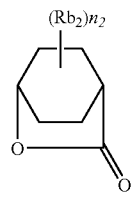

LC1-11

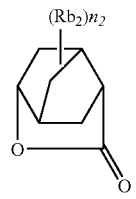

LC1-12

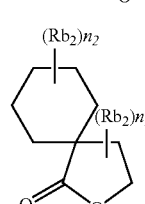

LC1-13

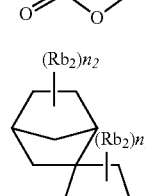

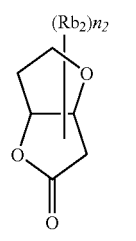

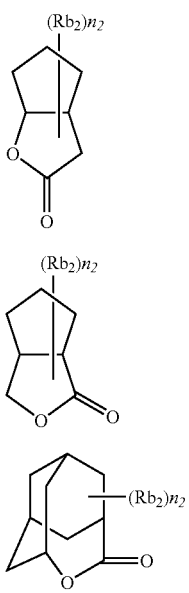

LC1-14

LC1-15

LC1-16

A lactone structure moiety may have or may not have a substituent ($Rb_2$). As preferred substituents ($Rb_2$), an alkyl group having from 1 to 8 carbon atoms, a cycloalkyl group having from 4 to 7 carbon atoms, an alkoxyl group having from 1 to 8 carbon atoms, an alkoxycarbonyl group having from 1 to 8 carbon atoms, a carboxyl group, a halogen atom, a hydroxyl group, a cyano group, and an acid-decomposable group are exemplified. When $n_2$ is 2 or more, a plurality of $Rb_2$'s may be the same or different, and a plurality of substituents ($Rb_2$'s) may be bonded to each other to form a ring.

As the repeating units having a group having a lactone structure represented by any of formulae (LC1-1) to (LC1-16), the repeating unit represented by formula (II-AB1) or (II-AB2) in which at least one of $R_{13}'$ to $R_{16}'$ has a group represented by any of formulae (LC1-1) to (LC1-16) (for example, $R_5$ of —$COOR_5$ represents a group represented by any of formulae (LC1-1) to (LC1-16)), or a repeating unit represented by the following formula (AI) can be exemplified.

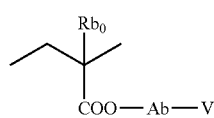

(AI)

In formula (AI), $Rb_0$ represents a hydrogen atom, a halogen atom, or an alkyl group having from 1 to 4 carbon atoms. As the preferred substituents that the alkyl group represented by $Rb_0$ may have, a hydroxyl group and a halogen atom are exemplified.

As the halogen atom represented by $Rb_0$, a fluorine atom, a chlorine atom, a bromine atom and an iodine atom can be exemplified.

$Rb_0$ preferably represents a hydrogen atom or a methyl group.

Ab represents a single bond, an alkylene group, a divalent linking group having a monocyclic or polycyclic alicyclic hydrocarbon structure, an ether group, an ester group, a carbonyl group, or a divalent linking group combining these groups. Ab preferably represents a single bond or a linking group represented by -$Ab_1$—$CO_2$—. $Ab_1$ represents a straight chain or branched alkylene group, or a monocyclic or polycyclic cycloalkylene group, and preferably a methylene group, an ethylene group, a cyclohexylene group, an adamantylene group, or a norbornylene group.

V represents a group represented by any of formulae (LC1-1) to (LC1-16).

Repeating units having a lactone structure generally have optical isomers, and any optical isomer may be used. One kind of optical isomer may be used alone, or a plurality of optical isomers may be used as mixture. When one kind of optical isomer is mainly used, the optical purity (ee) of the optical isomer is preferably 90 or more, and more preferably 95 or more.

The content of the repeating unit having a lactone structure is preferably from 15 to 60 mol % based on all the repeating units in the polymer, more preferably from 20 to 50 mol %, and still more preferably from 30 to 50 mol %.

As repeating units having an especially preferred lactone group, the following repeating units are exemplified. By the selection of an optimal lactone structure, pattern profile and pitch dependency are bettered.

(In the formulae, Rx represents H, $CH_3$, $CH_2OH$ or $CF_3$.

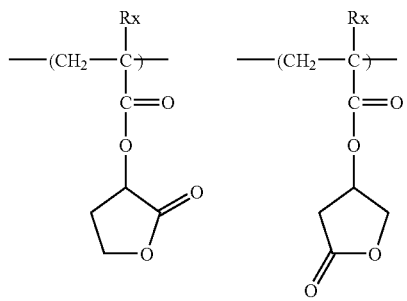

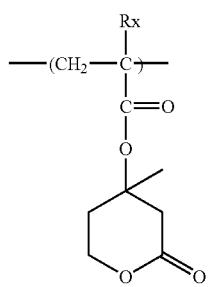

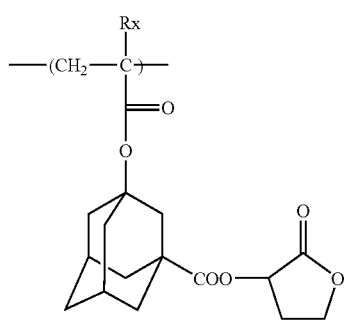

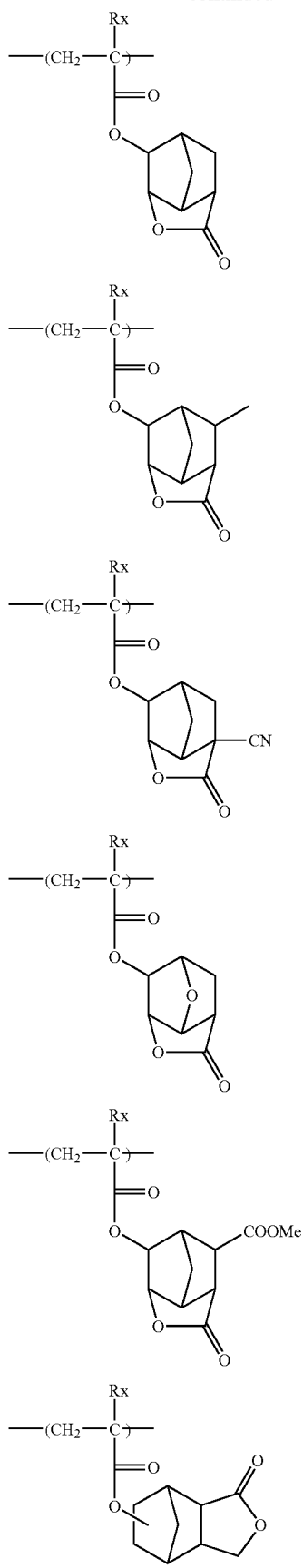

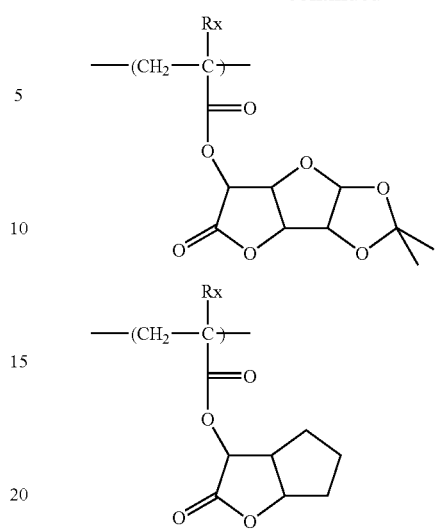

It is preferred for the alicyclic hydrocarbon series acid-decomposable resin in the invention to have a repeating unit having an alicyclic hydrocarbon structure substituted with a polar group, by which adhesion with a substrate and affinity with a developing solution are improved. As the alicyclic hydrocarbon structure of the alicyclic hydrocarbon structure substituted with a polar group, an adamantyl group, a diamantyl group, and a norbornane group are preferred. As the polar groups, a hydroxyl group and a cyano group are preferred. As the alicyclic hydrocarbon structure substituted with a preferred polar group, a partial structure represented by any of the following formulae (VIIa) to (VIId) is preferred.

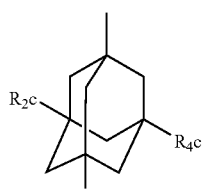

(VIIa)

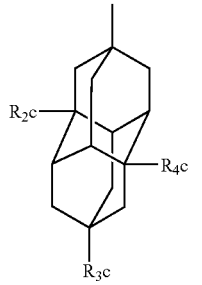

(VIIb)

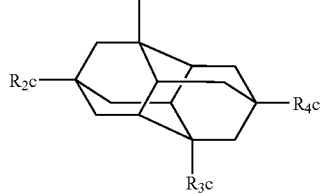

(VIIc)

-continued

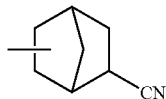
(VIId)

In formula (VIIa) to (VIIc), $R_{2c}$, $R_{3c}$ and $R_{4c}$ each represents a hydrogen atom, a hydroxyl group, or a cyano group, provided that at least one of $R_{2c}$, $R_{3c}$ and $R_{4c}$ represents a hydroxyl group or a cyano group. Preferably one or two of $R_{2c}$, $R_{3c}$ and $R_{4c}$ represent a hydroxyl group and the remainder represents a hydrogen atom. In formula (VIIa), more preferably two of $R_{2c}$, $R_{3c}$ and $R_{4c}$ represent a hydroxyl group and the remainder represents a hydrogen atom.

As the repeating unit having a group represented by any of formulae (VIIa) to (VIId), a repeating unit represented by formula (II-AB1) or (II-AB2) in which at least one of $R_{13}'$ to $R_{16}'$ has a group represented by any of formulae (VIIa) to (VIId) (for example, $R_5$ of —COOR$_5$ represents a group represented by any of formulae (VIIa) to (VIId)), or a repeating unit represented by any of the following formulae (AIIa) to (AIId) can be exemplified.

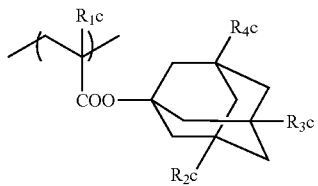
(AIIa)

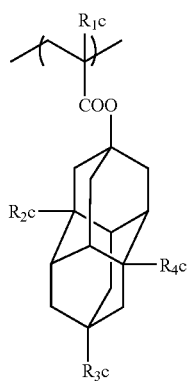
(AIIb)

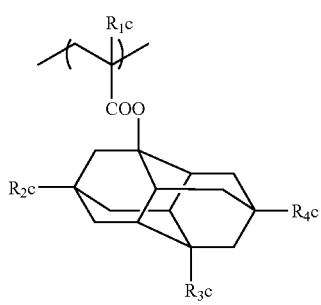
(AIIc)

-continued

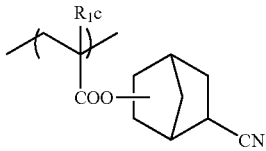
(AIId)

In formulae (AIIa) to (AIId), $R_{1c}$ represents a hydrogen atom, a methyl group, a trifluoromethyl group, or a hydroxymethyl group.

$R_{2c}$, $R_{3c}$ and $R_{4c}$ have the same meaning as $R_{2c}$ to $R_{4c}$ in formulae (VIIa) to (VIIc).

The content of the repeating unit having an alicyclic hydrocarbon structure substituted with a polar group is preferably from 5 to 40 mol % based on all the repeating units in the polymer, more preferably from 5 to 30 mol %, and still more preferably from 10 to 25 mol %.

The specific examples of the repeating units represented by any of formulae (AIIa) to (AIId) are shown below, but the invention is not restricted thereto.

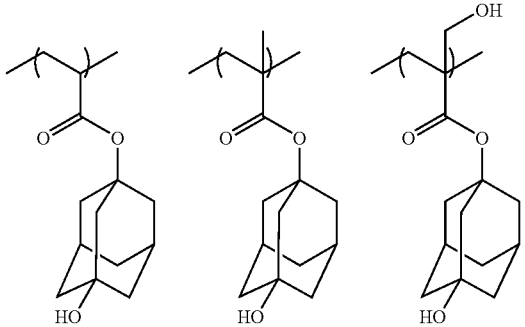

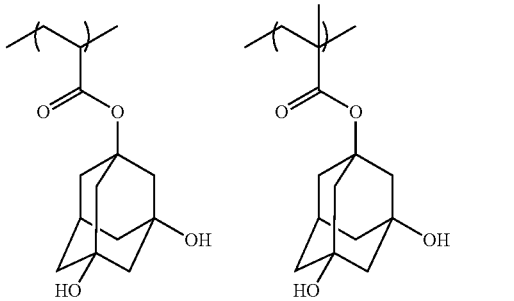

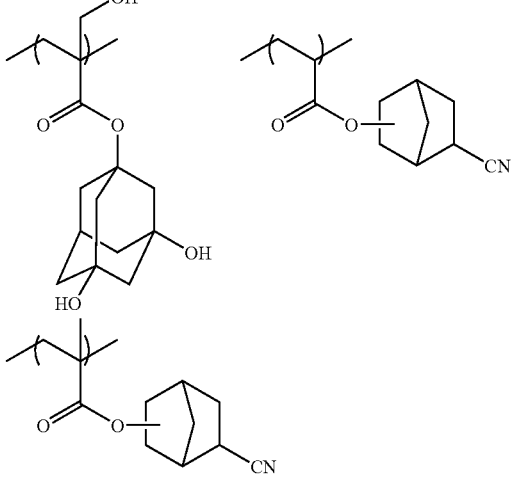

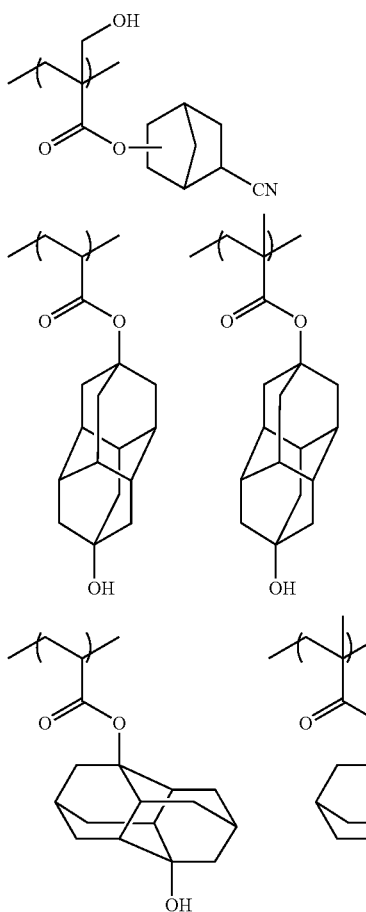

The alicyclic hydrocarbon series acid-decomposable resin in the invention may have a repeating unit represented by the following formula (VIII).

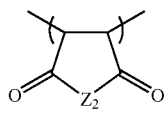

(VIII)

In formula (VIII), $Z_2$ represents —O— or —N($R_{41}$)—. $R_{41}$ represents a hydrogen atom, a hydroxyl group, an alkyl group, or —OSO$_2$—$R_{42}$. $R_{42}$ represents an alkyl group, a cycloalkyl group, or a camphor residue. The alkyl group represented by $R_{41}$, and $R_{42}$ may be substituted with a halogen atom (preferably a fluorine atom) and the like.

As the specific examples of the repeating units represented by formula (VIII), the following compounds are exemplified, but the invention is not restricted thereto.

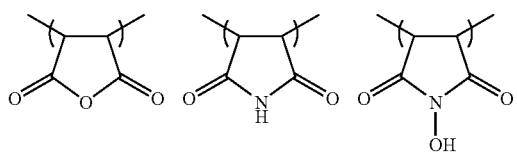

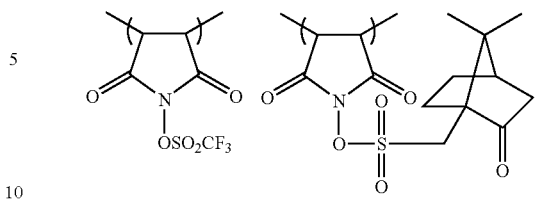

It is preferred for the alicyclic hydrocarbon series acid-decomposable resin in the invention to have a repeating unit having an alkali-soluble group. As the alkali-soluble groups, a carboxyl group, a sulfonamido group, a sulfonylimido group, a bisulfonylimido group, and an aliphatic alcohol substituted with an electron attractive group on the α-position (preferably a structure represented by the following formula (F1)) are exemplified, and it is more preferred to have a repeating unit having a carboxyl group.

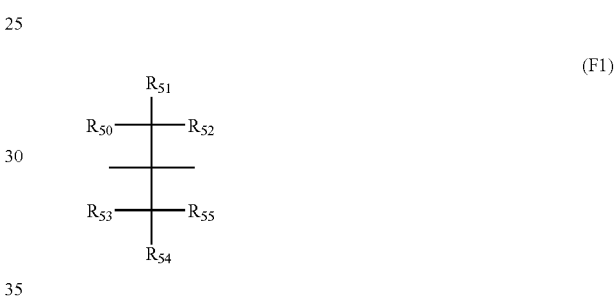

(F1)

In formula (F1), $R_{50}$, $R_{51}$, $R_{52}$, $R_{53}$, $R_{54}$ and $R_{55}$ each represents a hydrogen atom, a fluorine atom, or an alkyl group, provided that at least one of $R_{50}$ to $R_{55}$ represents a fluorine atom, or an alkyl group in which at least one hydrogen atom is substituted with a fluorine atom. It is preferred that all of $R_{50}$ to $R_{55}$ represent a fluorine atom.

By having a repeating unit having an alkali-soluble group, the resolution in the use for contact hole is enhanced. As the repeating units having an alkali-soluble group, a repeating unit having an alkali-soluble group directly bonded to the main chain of a resin such as a repeating unit by acrylic acid or methacrylic acid, a repeating unit having an alkali-soluble group bonded to the main chain of a resin via a linking group, and a repeating unit having an alkali-soluble group introduced to the terminals of a polymer chain by polymerization with a polymerization initiator having an alkali-soluble group and a chain transfer agent are exemplified, and any of these repeating units is preferably used. The linking group may have a monocyclic or polycyclic hydrocarbon structure. A repeating unit by acrylic acid or methacrylic acid is especially preferred.

The content of the repeating unit having an alkali-soluble group is preferably from 1 to 20 mol % based on all the repeating units in the polymer, more preferably from 3 to 15 mol %, and still more preferably from 5 to 10 mol %.

The specific examples of the repeating units having an alkali-soluble group are shown below, but the invention is not restricted thereto.

(In the formulae, Rx represents H, CH₃, CF₃ or CH₂OH.)

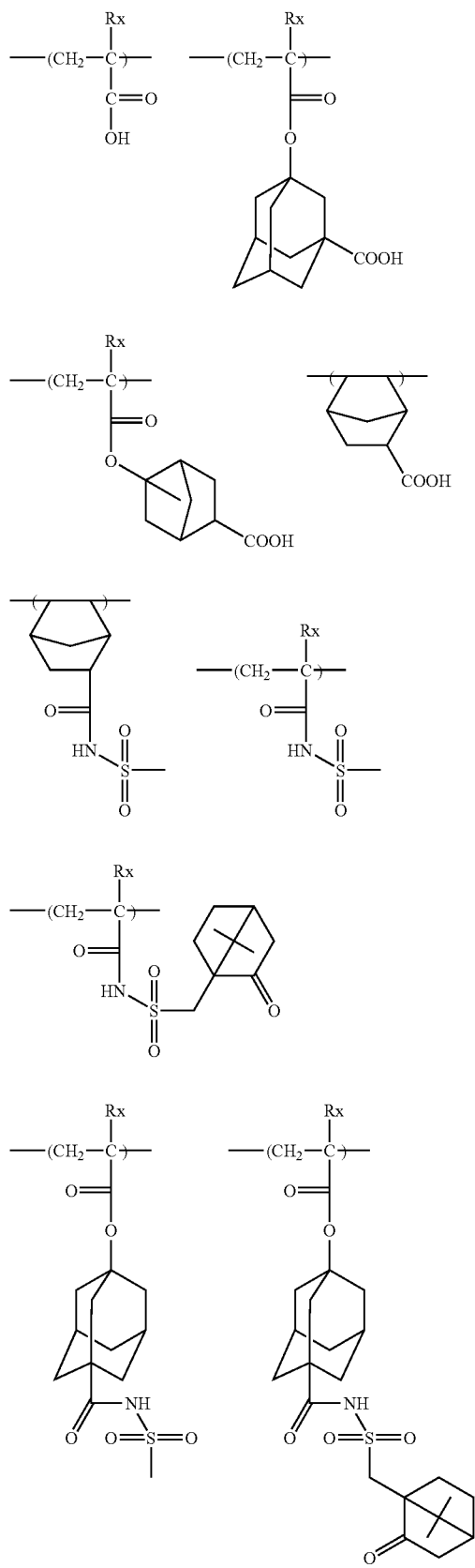

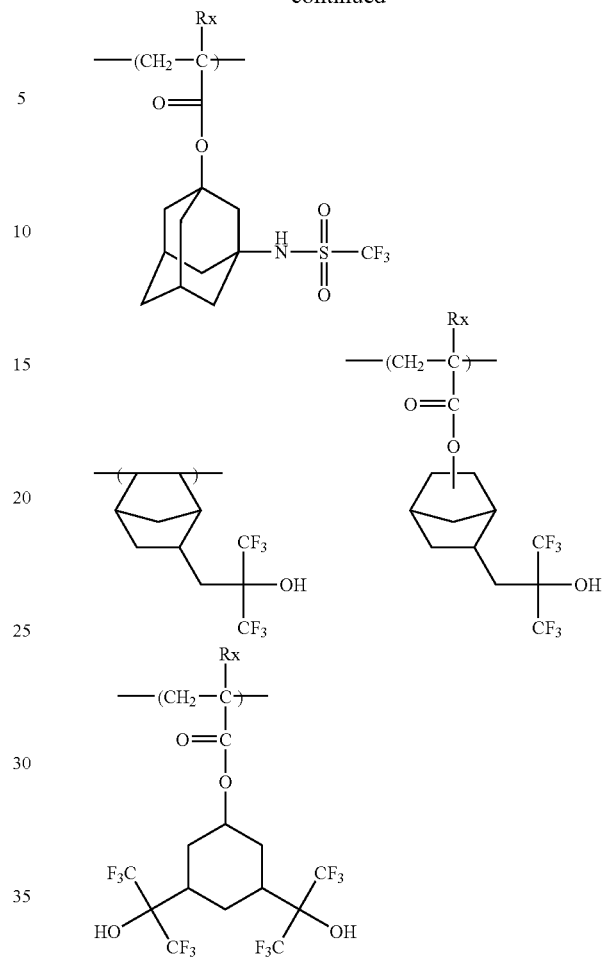

-continued

The alicyclic hydrocarbon series acid-decomposable resin in the invention may further have a repeating unit having an alicyclic hydrocarbon structure and not showing acid decomposability, by containing such a repeating unit, the elution of low molecular weight components from a resist film into an immersion liquid can be reduced at the time of immersion exposure. As such repeating units, e.g., 1-adamantyl(meth)acrylate, tricyclodecanyl(meth)acrylate, and cyclohexyl (meth)acrylate are exemplified.

The alicyclic hydrocarbon series acid-decomposable resin in the invention can contain various kinds of repeating structural units besides the above repeating structural units for the purpose of the adjustments of dry etching resistance, aptitude for standard developing solutions, adhesion to a substrate, resist profile, and general requisite characteristics of resists, e.g., resolution, heat resistance and sensitivity.

In addition to the aforementioned compounds, addition polymerizable unsaturated compounds copolymerizable with the monomers corresponding to the above various repeating structural units may be used for copolymerization.

In the alicyclic hydrocarbon series acid-decomposable resin, the molar ratio of the content of each repeating structural unit is arbitrarily set to adjust dry etching resistance, aptitude for standard developing solutions, adhesion to a substrate, and resist profile of a resist, and in addition to these characteristics, general requisite characteristics of a resist, e.g., resolution, heat resistance and sensitivity.

The content of the repeating unit having an acid decomposable group in the alicyclic hydrocarbon series acid-decomposable resin is preferably from 10 to 60 mol % in all the repeating structural units, more preferably from 20 to 50 mol %, and still more preferably from 25 to 40 mol %.

The content of the repeating unit having a partial structure containing the alicyclic hydrocarbon represented by any of formulae (pI) to (pV) in the alicyclic hydrocarbon series acid-decomposable resin is preferably from 20 to 70 mol % in all the repeating structural units, more preferably from 20 to 50 mol %, and still more preferably from 25 to 40 mol %.

The content of the repeating unit represented by formula (II-AB) in the alicyclic hydrocarbon series acid-decomposable resin is preferably from 10 to 60 mol % in all the repeating structural units, more preferably from 15 to 55 mol %, and still more preferably from 20 to 50 mol %.

When the composition of the invention is for ArF exposure, it is preferred that the resin does not have an aromatic group from the aspect of transparency to ArF rays.

The alicyclic hydrocarbon series acid-decomposable resin for use in the invention is preferably such that all the repeating units consist of (meth)acrylate repeating units. In this case, any of the following cases can be used, that is, a case where all the repeating units consist of methacrylate repeating units, a case where all the repeating units consist of acrylate repeating units, and a case where all the repeating units consist of mixture of methacrylate repeating units and acrylate repeating units, but it is preferred that acrylate repeating units account for 50 mol % or less of all the repeating units. The alicyclic hydrocarbon series acid-decomposable resin is preferably a copolymer containing from 20 to 50 mol % of a repeating unit having a partial structure containing the alicyclic hydrocarbon represented by any of formulae (pI) to (pV), from 20 to 50 mol % of a repeating unit having a lactone structure, and from 5 to 30 mol % of a repeating unit having an alicyclic hydrocarbon structure substituted with a polar group, or a copolymer further containing from 0 to 20 mol % of other repeating units.

An especially preferred resin is a resin having from 20 to 50 mol % of a repeating unit having an acid-decomposable group represented by any of the following formulae (ARA-1) to (ARA-5), from 20 to 50 mol % of a repeating unit having a lactone group represented by any of the following formulae (ARL-1) to (ARL-6), and from 5 to 30 mol % of a repeating unit having an alicyclic hydrocarbon structure substituted with a polar group represented by any of the following formulae (ARH-1) to (ARH-3), or a resin further containing from 5 to 20 mol % of a repeating unit having a carboxyl group or a structure represented by formula (F1), and a repeating unit having an alicyclic hydrocarbon structure and not showing acid decomposability.

In the following formulae, $Rxy_1$ represents a hydrogen atom or a methyl group, and $Rxa_1$ and $Rxb_1$ each represents a methyl group or an ethyl group.

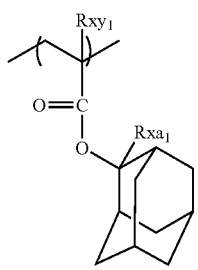

ARA-1

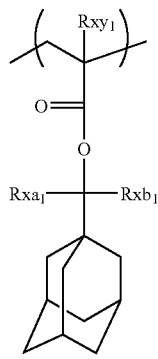

ARA-2

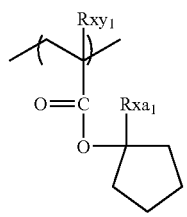

ARA-3

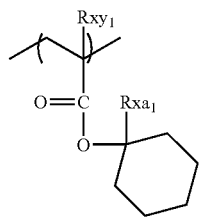

ARA-4

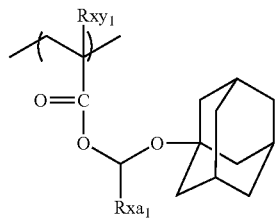

ARA-5

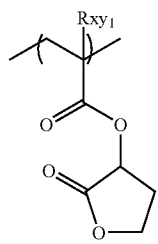

ARL-1

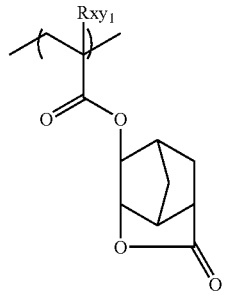

ARL-2

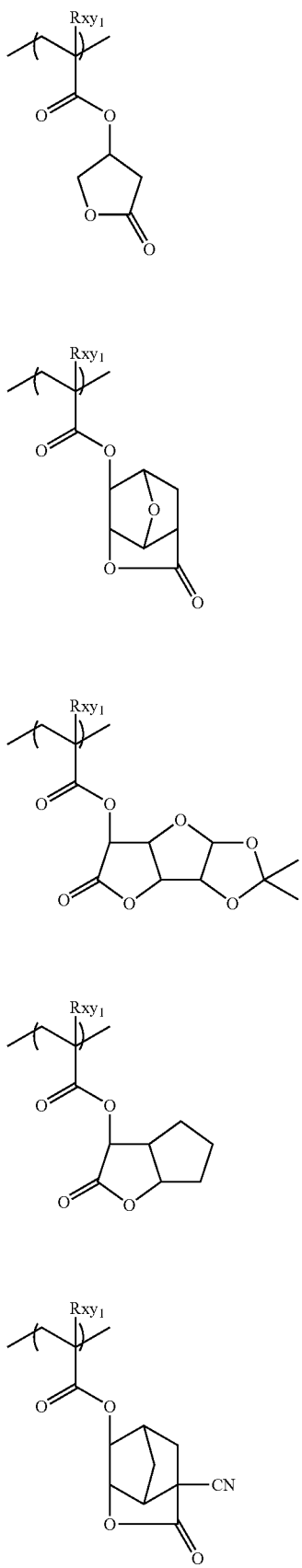

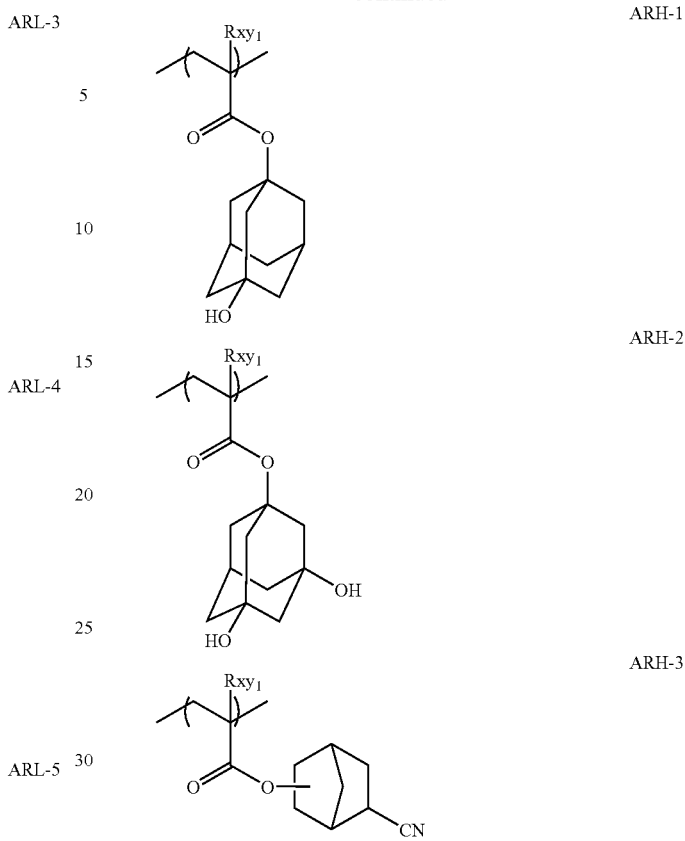

The alicyclic hydrocarbon series acid-decomposable resin for use in the invention can be synthesized according to ordinary methods (e.g., radical polymerization). For instance, as ordinary methods, a batch polymerization method of dissolving a monomer and an initiator in a solvent and heating the solution to perform polymerization, and a dropping polymerization method of adding a solution of a monomer and an initiator to a heated solvent over 1 to 10 hours by dropping are exemplified, and dropping polymerization is preferred. As reaction solvents, ethers, e.g., tetrahydrofuran, 1,4-dioxane, and diisopropyl ether, ketones, e.g., methyl ethyl ketone and methyl isobutyl ketone, an ester solvent, e.g., ethyl acetate, amide solvents, e.g., dimethylformamide and dimethyacetamide, and the later-described solvents capable of dissolving the composition of the invention, e.g., propyelne glycol monomethyl ether acetate, propylene glycol monomethyl ether, and cyclohexanone are exemplified. It is more preferred to use the same solvent in polymerization as the solvent used in the resist composition in the invention, by which generation of particles during preservation can be restrained.

It is preferred to perform polymerization reaction in the atmosphere of inert gas such as nitrogen or argon. Polymerization is initiated with commercially available radical initiators (e.g., azo initiators, peroxide and the like). As the radical initiators, azo initiators are preferred, and azo initiators having an ester group, a cyano group, or a carboxyl group are preferred. As preferred initiators, azobisisobutyronitrile, azobisdimethylvalero-nitrile, dimethyl-2,2'-azibis(2-methylpropionate) and the like are exemplified. A chain transfer agent such as a thiol compound may be used in combination with a polymerization initiator. Initiators are added additionally or dividedly, if desired, and after termination of the reaction, the reaction product is put into a solvent and an objective polymer is recovered as powder or a solid state. The reaction concentration is from 5 to 50 mass %, and preferably from 10 to 30 mass %. The reaction temperature is generally from 10 to 150° C., preferably from 30 to 120° C., and more preferably from 60 to 100° C.

When the composition according to the invention is used in the upper layer resist of a multilayer resist, it is preferred that the resin of component (B) should have a silicon atom.

As resins having a silicon atom and that decomposes by the action of an acid to increase the solubility in an alkali developer, resins having a silicon atom at least on one side of the main chain and the side chain can be used. As resins having a siloxane structure on the side chain of resins, copolymers of, e.g., an olefin monomer having a silicon atom on the side chain and a (meth)acrylic acid monomer having maleic acid anhydride and an acid-decomposable group on the side chain can be exemplified.

As resins having a silicon atom, resins having a trialkylsilyl structure, and a monocyclic or polycyclic siloxane structure are preferred, resins having a repeating unit having the structure represented by any of the following formulae (SS-1) to (SS-4) are more preferred, and resins having a (meth)acrylic acid ester repeating unit having a structure represented by any of formulae (SS-1) to (SS-4), a vinyl repeating unit, and an allyl repeating unit are still more preferred.

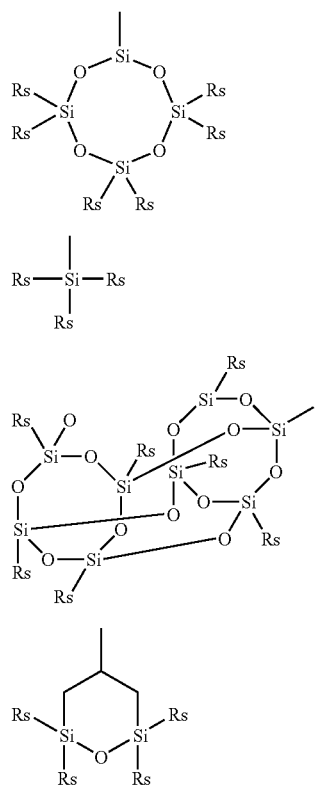

In formulae (SS-1) to (SS-4), Rs represents an alkyl group having from 1 to 5 carbon atoms, preferably a methyl group or an ethyl group.

It is preferred that resins having silicon atoms have two or more kinds of different repeating units having silicon atoms, resins having both (Sa) a repeating unit having from 1 to 4 silicon atoms, and (Sb) a repeating unit having from 5 to 10 silicon atoms are more preferred, and resins having at least one repeating unit having a structure represented by any of formulae (SS-1) to (SS-3) and a repeating unit having a structure represented by formula (SS-4) are still more preferred.

As the preferred specific examples of resins having a silicon atom, the following (SI-1) to (SI-5) are exemplified.

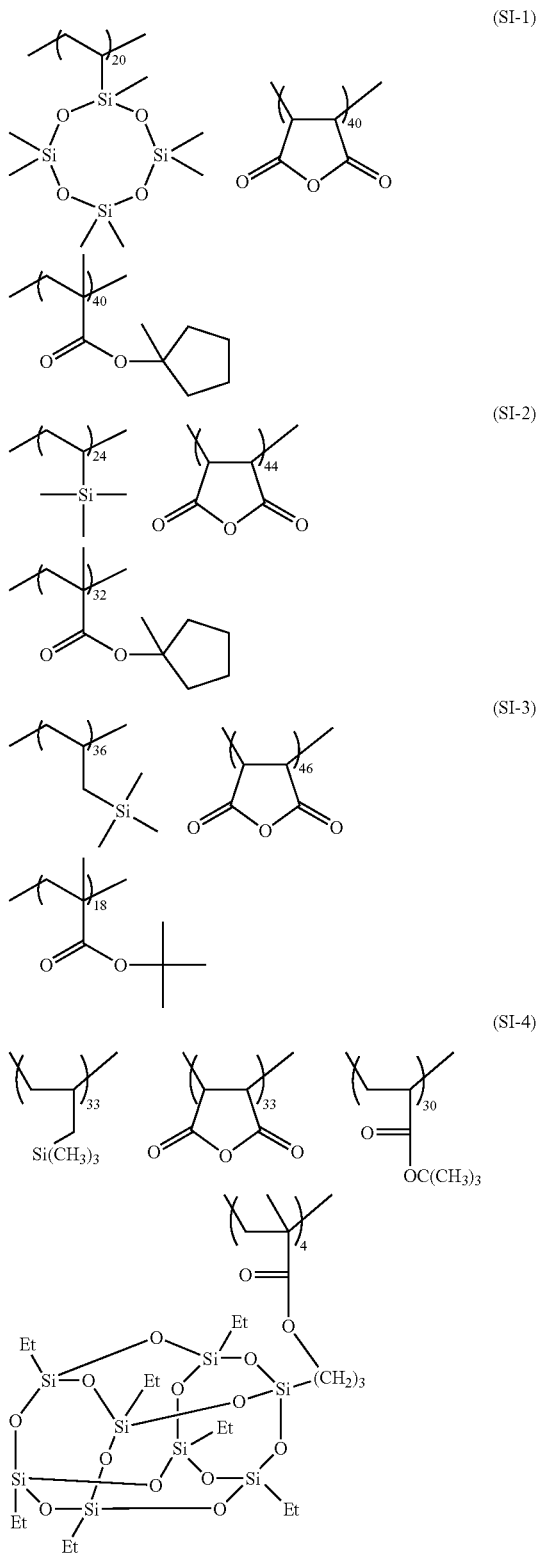

-continued

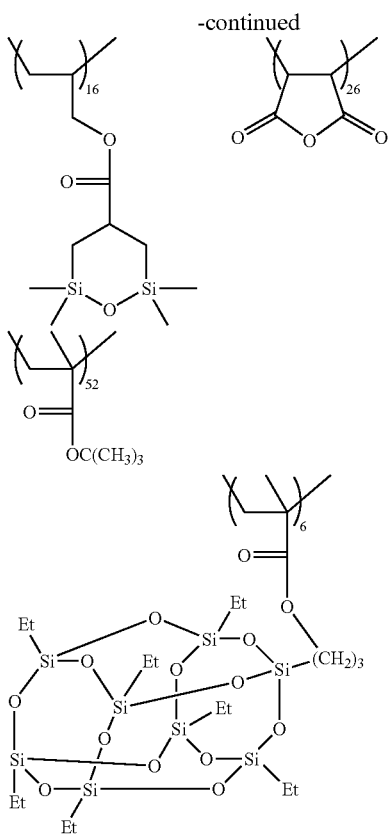

The weight average molecular weight of the resin of component (B) is preferably from 1,000 to 200,000 as the polystyrene equivalent value by the GPC method, more preferably from 3,000 to 20,000, and especially preferably from 5,000 to 15,000. By making the weight average molecular weight from 1,000 to 200,000, the deterioration of heat resistance and dry etching resistance can be prevented, and can also restrain deterioration of a developing property and prevent a film forming property from deteriorating due to the increase in viscosity.

Molecular weight distribution is generally from 1 to 5, preferably from 1 to 2, and more preferably from 1.3 to 2. The smaller the molecular weight distribution, the more excellent are the resolution and resist form, the smoother is the side wall of the resist pattern, and the more excellent is the roughness property.

In the photosensitive composition of the invention, the blending amount of the resin of component (B) in the composition as a whole is preferably from 60 to 99 mass % in all the solids content, and more preferably from 80 to 98 mass %.

Further, in the invention, the resin may be used by one kind alone, or a plurality of resins may be used in combination. A dissolution-controlling compound having at least one group selected from an alkali-soluble group, a hydrophilic group and an acid- decomposable group, and having a molecular weight of 3,000 or less:

The photosensitive composition of the invention can contain a dissolution-controlling compound having at least one group selected from an alkali-soluble group, a hydrophilic group and an acid-decomposable group, and having a molecular weight of 3,000 or less (hereinafter also referred to as "a dissolution-inhibiting compound").

As the dissolution-controlling compound, a compound having an alkali-soluble group such as a carboxyl group, a sulfonylimido group, or a hydroxyl group substituted with a fluoroalkyl group on the α-position, a compound having a hydrophilic group such as a hydroxyl group, a lactone group, a cyano group, an amido group, a pyrrolidone group, or a sulfonamido group, and a compound containing a group that decomposes by the action of an acid to release an alkali-soluble group or a hydrophilic group are preferably used. As the group that decomposes by the action of an acid to release an alkali-soluble group or a hydrophilic group, a group protecting a carboxyl group or a hydroxyl group with an acid-elimination group is preferred. Not to lower penetration of wavelengths of 220 nm or less, it is preferred to use a compound not containing an aromatic ring as the dissolution-controlling compound, or use a compound containing an aromatic ring in the addition amount of 20 wt % or less based on the solid content of the composition.

As the preferred dissolution-controlling compounds, carboxylic acid compounds having an alicyclic hydrocarbon structure such as adamantane (di)carboxylic acid, norbornane carboxylic acid, or cholic acid, or compounds protecting these carboxylic acids with an acid-elimination group, and compounds protecting polyol such as saccharides or the hydroxyl group thereof with an acid-decomposable group are exemplified.

The molecular weight of the dissolution-controlling compound in the invention is 3,000 or less, preferably from 300 to 3,000, and more preferably from 500 to 2,500.

The addition amount of the dissolution-controlling compound is preferably from 3 to 40 mass % based on the solids content of the photosensitive composition, and more preferably from 5 to 20 mass %.

The specific examples of the dissolution-controlling compounds are shown below, but the invention is not limited thereto.

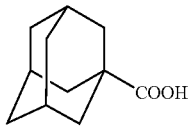

TE-1

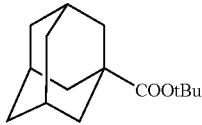

TE-2

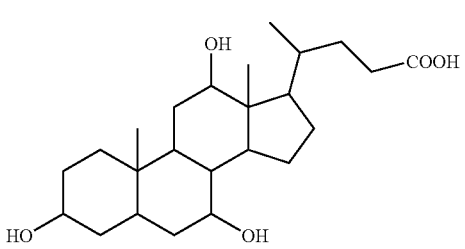

TE-3

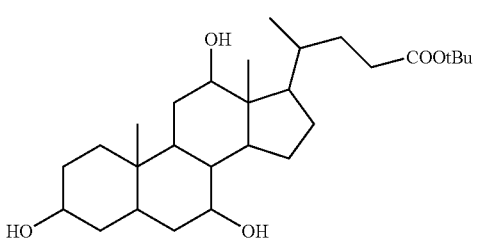

TE-4

-continued

TE-5
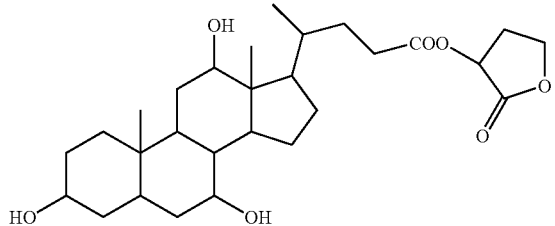

TE-6
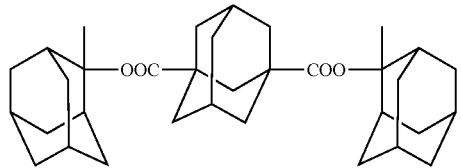

TE-7
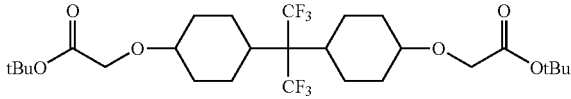

TE-8
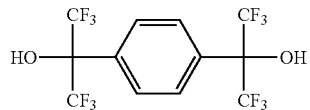

TE-9
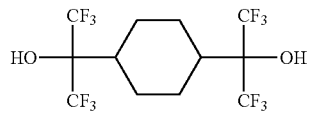

TE-10
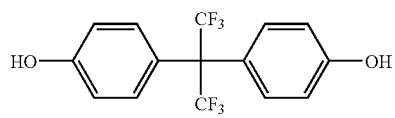

TE-11
HO—(CH$_2$)$_{12}$—OH

TE-12
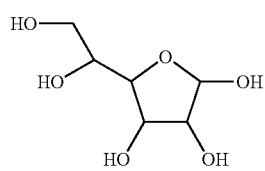

TE-13
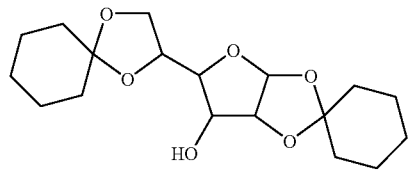

TE-14
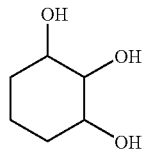

TE-15
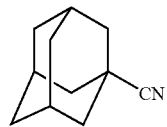

TE-16
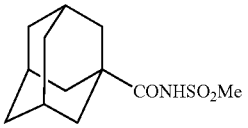

Basic Compound:

For reducing the fluctuation of performances due to aging from exposure to heating, or for controlling the diffusion of an acid generated by exposure in a film, it is preferred for the photosensitive composition of the invention to contain a basic compound.

As basic compounds, nitrogen-containing basic compounds and onium salt compounds can be exemplified. As preferred structure of nitrogen-containing basic compounds, compounds having a partial structure represented be any of the following formulae (A) to (E) can be exemplified.

(A)
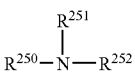

(B)
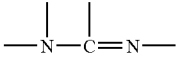

(C)
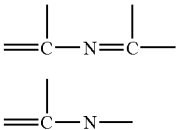

(D)
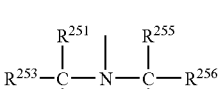

(E)
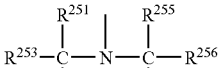

In formula (A), $R^{250}$, $R^{251}$ and $R^{252}$ each represents a hydrogen atom, an alkyl group having from 1 to 20 carbon atoms, a cycloalkyl group having from 3 to 20 carbon atoms, or an aryl group having from 6 to 20 carbon atoms, and $R^{250}$ and $R^{251}$ may be bonded to each other to form a ring. These groups may have a substituent, and as the alkyl group and the cycloalkyl group having a substituent, an aminoalkyl group having from 1 to 20 carbon atoms, an aminocycloalkyl group having from 3 to 20 carbon atoms, a hydroxyalkyl group having from 1 to 20 carbon atoms, and a hydroxycycloalkyl group having from 3 to 20 carbon atoms are preferred.

These groups may contain an oxygen atom, a sulfur atom or a nitrogen atom in the alkyl chain.

In formula (E), $R^{253}$, $R^{254}$, $R^{255}$ and $R^{256}$ each represents an alkyl group having from 1 to 6 carbon atoms, or a cycloalkyl group having from 3 to 6 carbon atoms.

As preferred examples of basic compounds, guanidine, aminopyrrolidine, pyrazole, pyrazoline, piperazine, aminomorpholine, aminoalkylmorpholine, and piperidine can be exemplified, and these compounds may have a substituent. As further preferred compounds, a compound having an imidazole structure, a diazabicyclo structure, an onium hydroxide structure, an onium carboxylate structure, a trialkylamine structure, an aniline structure, or a pyridine structure, an alkylamine derivative having at least one of a hydroxyl group and an ether bond, an aniline derivative having at least one of a hydroxyl group and an ether bond, etc., can be exemplified.

As the compound having an imidazole structure, 2,4,5-triphenylimidazole, benzimidazole and 2-phenyl benzimidazole can be exemplified. As the compounds having a diazabicyclo structure, 1,4-diaza-bicyclo[2,2,2]octane, 1,5-diazabicyclo[4,3,0]nona-5-ene, and 1,8-diazabicyclo[5,4,0]undeca-7-ene can be exemplified. As the compounds having an onium hydroxide structure, triaryl-sulfonium hydroxide, phenacylsulfonium hydroxide, sulfonium hydroxide having a 2-oxoalkyl group, specifically triphenyl-sulfonium hydroxide, tris(t-butylphenyl)sulfonium hydroxide, bis(t-butylphenyl)iodonium hydroxide, phenacylthiophenium hydroxide, and 2-oxopropylthiophenium hydroxide can be exemplified. The compounds having an onium carboxylate structure are compounds having an onium hydroxide structure in which the anionic part is carboxylated, e.g., acetate, adamantane-1-carboxylate and perfluoroalkyl carboxylate are exemplified. As the compounds having a trialkylamine structure, tri(n-butyl)amine and tri(n-octyl)amine are exemplified. As the aniline compounds, 2,6-diisopropyl-aniline and N,N-dimethylaniline are exemplified. As the alkylamine derivatives having at least one of a hydroxyl group and an ether bond, ethanolamine, diethanolamine, triethanol-amine, tris(methoxyethoxyethyl)amine, N-phenyldiethanolamine are exemplified. As the aniline derivatives having at least one of a hydroxyl group and an ether bond, N,N-bis(hydroxyethyl)aniline is exemplified.

As preferred basic compounds, amine compounds having a phenoxy group and ammonium salt compounds having a phenoxy group can further be exemplified.

As the amine compounds, primary, secondary and tertiary amine compounds can be used, and amine compounds in which at least one alkyl group is bonded to the nitrogen atom are preferred. The amine compounds are more preferably tertiary amine compounds. So long as at least one alkyl group (preferably having from 1 to 20 carbon atoms) is bonded to the nitrogen atom, the amine compounds may be such that a cycloalkyl group (preferably having from 3 to 20 carbon atoms) or an aryl group (preferably having from 6 to 12 carbon atoms) is bonded to the nitrogen atom besides the alkyl group.

Further, it is preferred that the amine compounds have an oxygen atom in the alkyl chain to form an oxyalkylene group. The number of the oxyalkylene group is one or more in the molecule, preferably from 3 to 9, and more preferably from 4 to 6. Of the oxyalkylene groups, an oxyethylene group (—$CH_2CH_2O$—) or an oxypropylene group (—$CH(CH_3)CH_2O$— or —$CH_2CH_2CH_2O$—) is preferred, and an oxyethylene group is more preferred.

As the ammonium salt compounds, primary, secondary, tertiary and quaternary ammonium salt compounds can be used, and ammonium salt compounds in which at least one alkyl group is bonded to the nitrogen atom are preferred. So long as at least one alkyl group (preferably having from 1 to 20 carbon atoms) is bonded to the nitrogen atom, the ammonium salt compounds may be such that a cycloalkyl group (preferably having from 3 to 20 carbon atoms) or an aryl group (preferably having from 6 to 12 carbon atoms) is bonded to the nitrogen atom besides the alkyl group.

It is preferred that the ammonium salt compounds have an oxygen atom in the alkyl chain to form an oxyalkylene group. The number of the oxyalkylene group is one or more in the molecule, preferably from 3 to 9, and more preferably from 4 to 6. Of the oxyalkylene groups, an oxyethylene group (—$CH_2CH_2O$—) or an oxypropylene group (—$CH(CH_3)CH_2O$— or —$CH_2CH_2CH_2O$—) is preferred, and an oxyethylene group is more preferred.

As the anions of the ammonium salt compounds, a halogen atom, sulfonate, borate, phosphate, etc., are exemplified, and a halogen atom and sulfonate are preferred of these. As the halogen atom, chloride, bromide and iodide are especially preferred, and as the sulfonate, organic sulfonates having from 1 to 20 carbon atoms are especially preferred. As the organic sulfonates, alkylsulfonate having from 1 to 20 carbon atoms and arylsulfonate are exemplified. The alkyl group of the alkylsulfonate may have a substituent and, e.g., fluorine, chlorine, bromine, an alkoxyl group, an acyl group, an aryl group, etc., are exemplified as the substituents. The specific examples of the alkylsulfonates include methane-sulfonate, ethanesulfonate, butanesulfonate, hexanesulfonate, octanesulfonate, benzylsulfonate, trifluoromethanesulfonate, pentafluoroethanesulfonate, nonafluorobutanesulfonate, etc., are exemplified. As the aryl groups of the arylsulfonate, a benzene ring, a naphthalene ring, and an anthracene ring are exemplified. The benzene ring, naphthalene ring and anthracene ring may have a substituent and, e.g., a straight chain or branched alkyl group having from 1 to 6 carbon atoms, and a cycloalkyl group having from 3 to 6 carbon atoms are preferred as the substituents. As the straight chain or branched alkyl group and cycloalkyl group, methyl, ethyl, n-propyl, isopropyl, n-butyl, i-butyl, t-butyl, n-hexyl, cyclohexyl, etc., are specifically exemplified. The examples of other substituents include an alkoxyl group having from 1 to 6 carbon atoms, a halogen atom, a cyano group, a nitro group, an acyl group, an acyloxy group, etc., are exemplified.

The amine compounds having a phenoxy group and the ammonium salt compounds having a phenoxy group are amine compounds and ammonium salt compounds having a phenoxy group at terminals on the side opposite to the nitrogen atom of the alkyl group of the amine compounds and the ammonium salt compounds. The phenoxy group may have a substituent and, e.g., an alkyl group, an alkoxyl group, a halogen atom, a cyano group, a nitro group, a carboxyl group, a carboxylate group, a sulfonate group, an aryl group, an aralkyl group, an acyloxy group, an aryloxy group, etc., can be exemplified as the substituents of the phenoxy group. The position of substitution of the substituents may be any of the 2- to 6-positions. The number of the substituents may be any in the range of from 1 to 5.

It is preferred to have at least one oxyalkylene group between the phenoxy group and the nitrogen atom. The number of the oxyalkylene group is one or more in the molecule, preferably from 3 to 9, and more preferably from 4 to 6. Of the oxyalkylene groups, an oxyethylene group (—$CH_2CH_2O$—) or an oxypropylene group (—$CH(CH_3)CH_2O$— or —$CH_2CH_2CH_2O$—) is preferred, and an oxyethylene group is more preferred.

The amine compound having a phenoxy group can be obtained by reacting primary or secondary amine having a phenoxy group with haloalkyl ether by heating, adding thereto an aqueous solution of a strong base, e.g., sodium hydroxide, potassium hydroxide or tetraalkylammonium, and extracting with an organic solvent, e.g., ethyl acetate, chloroform, etc. Alternatively, the compound can be obtained by reacting primary or secondary amine with haloalkyl ether having a phenoxy group at the terminal by heating, adding thereto an aqueous solution of a strong base, e.g., sodium hydroxide, potassium hydroxide or tetraalkylammonium, and extracting with an organic solvent, e.g., ethyl acetate, chloroform, etc.

These basic compounds are used alone or in combination of two or more.

The use amount of these basic compounds is generally from 0.001 to 10 mass % based on the solids content of the photosensitive composition, and preferably from 0.01 to 5 mass %. For obtaining a sufficient addition effect, the addition amount is preferably 0.001 mass % or more, and in view of sensitivity and the developing property of a non-exposed part, the amount is preferably 10 mass % or less.

Fluorine and/or Silicon Surfactant:

It is preferred for the photosensitive composition in the invention to further contain either one, or two or more, of fluorine and/or silicon surfactants (a fluorine surfactant, a silicon surfactant, a surfactant containing both a fluorine atom and a silicon atom).

By containing fluorine and/or silicon surfactants, it becomes possible for the photosensitive composition in the invention to provide a resist pattern excellent in sensitivity and resolution, and low in defects in adhesion and development at the time of using an exposure light source of 250 nm or lower, in particular, 220 nm or lower.

These fluorine and/or silicon surfactants are disclosed, e.g., in JP-A-62-36663, JP-A-61-226746, JP-A-61-226745, JP-A-62-170950, JP-A-63-34540, JP-A-7-230165, JP-A-8-62834, JP-A-9-54432, JP-A-9-5988, JP-A-2002-277862, U.S. Pat. Nos. 5,405,720, 5,360,692, 5,529,881, 5,296,330, 5,436,098, 5,576,143, 5,294,511 and 5,824,451. The commercially available surfactants shown below can also be used as they are.

As commercially available fluorine or silicon surfactants usable in the invention, Eftop EF301 and EF303 (manufactured by Shin-Akita Kasei Co., Ltd.), Fluorad FC 430 and 431 (manufactured by Sumitomo 3M Limited), Megafac F171, F173, F176, F189 and R08 (manufactured by Dainippon Ink and Chemicals Inc.), Sarfron S-382, SC 101, 102, 103, 104, 105 and 106 (manufactured by ASAHI GLASS CO., LTD.), and Troy Sol S-366 (manufactured by Troy Chemical Co., Ltd.) are exemplified. In addition, polysiloxane polymer KP-341 (manufactured by Shin-Etsu Chemical Co., Ltd.) can also be used as silicon surfactant.

In addition to these known surfactants as exemplified above, surfactants using polymers having fluoro-aliphatic groups derived from fluoro-aliphatic compounds manufactured by a telomerization method (also called a telomer method) or an oligomerization method (also called an oligomer method) can be used. Fluoro-aliphatic compounds can be synthesized according to the method disclosed in JP-A-2002-90991.

As the polymers having fluoro-aliphatic groups, copolymers of monomers having fluoro-aliphatic groups and (poly (oxyalkylene))acrylate and/or (poly(oxyalkylene))methacrylate are preferred, and the monomers may be distributed at random or block copolymerized. As the poly(oxyalkylene) groups, a poly(oxyethylene) group, a poly(oxypropylene) group, and a poly(oxybutylene) group are exemplified. Further, the polymers may be units having alkylenes different in the chain length in the same chain length, such as a block combination of poly(oxyethylene and oxypropylene and oxyethylene), and a block combination of poly(oxyethylene and oxypropylene). In addition, copolymers of monomers having fluoro-aliphatic groups and poly(oxyalkylene)acrylate (or methacrylate) may be not only bipolymers but also terpolymers or higher polymers obtained by copolymerization of monomers having different two or more kinds of fluoro-aliphatic groups and different two or more kinds of poly (oxyalkylene)acrylates (or methacrylates) at the same time.

For example, as commercially available surfactants, Megafac F178, F470, F473, F475, F476 and F472 (manufactured by Dainippon Ink and Chemicals Inc.) can be exemplified. Further, copolymers of acrylate (or methacrylate) having a $C_6F_{13}$ group and (poly(oxyalkylene))acrylate (or methacrylate), copolymers of acrylate (or methacrylate) having a $C_6F_{13}$ group, (poly(oxyethylene))acrylate (or methacrylate), and (poly-(oxypropylene))acrylate (or methacrylate), copolymers of acrylate (or methacrylate) having a $C_8F_{17}$ group and (poly-(oxyalkylene))acrylate (or methacrylate), copolymers of acrylate (or methacrylate) having a $C_8F_{17}$ group, (poly(oxy-ethylene))acrylate (or methacrylate), and (poly(oxy-propylene))acrylate (or methacrylate), etc., can be exemplified.

The use amount of fluorine and/or silicon surfactants is preferably from 0.0001 to 2 mass % based on all the amount of the photosensitive composition (exclusive of a solvent), and more preferably from 0.001 to 1 mass %.

Surface Hydrophobitizing Resin:

When a photosensitive film made of the photosensitive composition of the invention is subjected to exposure via an immersion liquid, a surface hydrophobitizing resin can further be added to the photosensitive composition, if necessary. By the addition of the surface hydrophobitizing resin, the sweepback contact angle of the photosensitive film surface can be improved and the following ability of the immersion liquid can be bettered. Any resins can be used as the surface hydrophobitizing resin so long as they can improve the sweepback contact angle of the film surface by the addition, but resins having at least either a fluorine atom or a silicon atom are preferably used. The addition amount can be arbitrarily adjusted so as to reach the sweepback contact angle of the photosensitive film of from 60° to 80°, and is preferably from 0.1 to 5 mass %.

The sweepback contact angle is a contact angle that is measured when a contact line at the interface of a droplet and a substrate makes a backward movement, and it is generally known to be useful in simulating the easiness of movement of a droplet in a dynamic state. When a droplet ejected from the tip of a needle is landed on a substrate and the droplet is again sucked into the needle, the sweepback contact angle can be simply defined as a contact angle at the time the interface of the droplet recedes. The contact angle can be measured with a measuring method generally called an expansion contraction method.

In an immersion exposure process, it is necessary for an immersion liquid to be capable of moving on a wafer following up the movement of an exposure head scanning on the wafer at a high speed and forming an exposure pattern, so that the contact angle of the immersion liquid to the resist film in a dynamic state is important, and the performance capable of following up the high speed scanning of the exposure head without leaving the droplet is required of the resist film.

Organic Solvent:

The above components of the photosensitive composition of the invention are dissolved in a prescribed organic solvent and used.

As the organic solvents usable in the invention, ethylene dichloride, cyclohexanone, cyclopentanone, 2-heptanone, γ-butyrolactone, methyl ethyl ketone, ethylene glycol monomethyl ether, ethylene glycol monoethyl ether, 2-methoxyethyl acetate, ethylene glycol monoethyl ether acetate, propylene glycol monomethyl ether, propylene glycol monomethyl ether acetate, toluene, ethyl acetate, methyl lactate, ethyl lactate, methyl methoxypropionate, ethyl ethoxypropionate, methyl pyruvate, ethyl pyruvate, propyl pyruvate, N,N-dimethylformamide, dimethyl sulfoxide, N-methylpyrrolidone, and tetrahydrofuran can be exemplified.

In the invention, organic solvents may be used alone or as mixture, but it is preferred to use a mixed solvent containing two or more kinds of solvents having different functional groups. By the use of such a mixed solvent, not only the solubility of materials is heightened and the generation of particles by aging can be restrained, but also a good pattern profile can be obtained. As the mixed solvents containing two or more kinds of solvents having different functional groups, mixed solvents containing at least two kinds of solvents selected from a solvent having a hydroxyl group, a solvent having an ester structure, a solvent having a ketone structure, a solvent having a lactone structure, and a solvent having a carbonate structure are preferred.

As the mixed solvents having different functional groups, the following mixed solvents (S1) to (S6) are preferred.

(S1): A mixed solvent at least containing a solvent having a hydroxyl group and a solvent not having a hydroxyl group;

(S2): A mixed solvent at least containing a solvent having an ester structure and a solvent having a ketone structure;

(S3): A mixed solvent at least containing a solvent having an ester structure and a solvent having a lactone structure;

(S4): A mixed solvent at least containing a solvent having an ester structure, a solvent having a lactone structure, and a solvent having a hydroxyl group;

(S5): A mixed solvent at least containing a solvent having an ester structure, a solvent having a carbonate structure, and a solvent having a hydroxyl group; and (S6): A mixed solvent at least containing a solvent having an ester structure, a solvent having a ketone structure, and a solvent having a lactone structure.

By the use of these mixed solvents, the generation of particles during preservation of a resist solution can be reduced and the occurrence of coating defects at the time of coating can be restrained.

As the solvents having a hydroxyl group, e.g., ethylene glycol, ethylene glycol monomethyl ether, ethylene glycol monoethyl ether, propylene glycol, propylene glycol monomethyl ether, propylene glycol monoethyl ether, ethyl lactate, etc., can be exemplified, and of these solvents, propylene glycol monomethyl ether and ethyl lactate are especially preferred.

As the solvents not having a hydroxyl group, e.g., propylene glycol monomethyl ether acetate, ethylethoxy-propionate, 2-heptanone, γ-butyrolactone, cyclohexanone, butyl acetate, N-methylpyrrolidone, N,N-dimethylacetamide, dimethyl sulfoxide, etc., can be exemplified, and of these solvents, propylene glycol monomethyl ether acetate, ethylethoxypropionate, 2-heptanone, γ-butyrolactone, cyclohexanone, and butyl acetate are preferred, and propylene glycol monomethyl ether acetate, ethylethoxypropionate, 2-heptanone, and cyclohexanone are especially preferred.

As the solvents having a ketone structure, cyclohexanone, 2-heptanone, etc., are exemplified, and 2-heptanone is preferred.

As the solvents having an ester structure, propylene glycol monomethyl ether acetate, ethylethoxypropionate, butyl acetate, etc., are exemplified, and propylene glycol monomethyl ether acetate is preferred.

As the solvent having a lactone structure, γ-butyrolactone is exemplified.

As the solvents having a carbonate structure, propylene carbonate and ethylene carbonate are exemplified, and propylene carbonate is preferred.

The mixing ratio (by mass) of the solvent having a hydroxyl group and the solvent not having a hydroxyl group in (S1) is from 1/99 to 99/1, preferably from 10/90 to 90/10, and more preferably from 20/80 to 60/40. Mixed solvents containing in the proportion of 50 mass % or more of the solvents not having a hydroxyl group are especially preferred in the point of capable of obtaining coating uniformity.

The mixing ratio (by mass) of the solvent having an ester structure and the solvent having a ketone structure in (S2) is from 1/99 to 99/1, preferably from 10/90 to 90/10, and more preferably from 40/60 to 80/20. Mixed solvents containing in the proportion of 50 mass % or more of the solvents having an ester structure are especially preferred in the point of capable of obtaining coating uniformity.

The mixing ratio (by mass) of the solvent having an ester structure and the solvent having a lactone structure in (S3) is from 70/30 to 99/1, preferably from 80/20 to 99/1, and more preferably from 90/10 to 99/1. Mixed solvents containing in the proportion of 70 mass % or more of the solvents having an ester structure are especially preferred in the light of aging stability.

When the solvent having an ester structure, the solvent having a lactone structure and the solvent having a hydroxyl group in (S4) are mixed, it is preferred to contain the solvent having an ester structure in the proportion of from 30 to 80 mass %, the solvent having a lactone structure in the proportion of from 1 to 20 mass %, and the solvent having a hydroxyl group in the proportion of from 10 to 60 mass %.

When the solvent having an ester structure, the solvent having a carbonate structure and the solvent having a hydroxyl group in (S5) are mixed, it is preferred to contain the solvent having an ester structure in the proportion of from 30 to 80 mass %, the solvent having a carbonate structure in the proportion of from 1 to 20 mass %, and the solvent having a hydroxyl group in the proportion of from 10 to 60 mass %.

When the solvent having an ester structure, the solvent having a ketone structure and the solvent having a lactone structure in (S6) are mixed, it is preferred to contain the solvent having an ester structure in the proportion of from 30 to 80 mass %, the solvent having a ketone structure in the proportion of from 10 to 60 mass %, and the solvent having a lactone structure in the proportion of from 1 to 20 mass %.

Other Additives:

If necessary, the photosensitive composition of the invention can further contain dyes, plasticizers, surfactants other than the above fluorine and/or silicon surfactants, and photosensitizers.

Solvents other than the above fluorine and/or silicon surfactants can be used in the invention. As specific examples of other solvents, nonionic surfactants, such as polyoxyethylene alkyl ethers, polyoxyethylene alkylallyl ethers, polyoxyethylene/polyoxypropylene block copolymers, sorbitan aliphatic esters, polyoxyethylene sorbitan aliphatic esters, etc., can be exemplified.

These surfactants can be used alone, or a couple of surfactants can be used in combination.

Pattern Forming Method:

The photosensitive composition in the invention is used by dissolving the above components in a prescribed organic solvent, preferably in the mixed solvent as described above, filtering through a filter, and coating the solution on a prescribed support as follows. The filter for use in filtration is preferably made of polytetrafluoroethylene, polyethylene or nylon having a pore diameter of 0.1 μm or less, more preferably 0.05 μm or less, and still more preferably 0.03 μm or less.

For example, the photosensitive composition is coated on a substrate such as the one used in the manufacture of fine integrated circuit elements (e.g., silicon/silicon dioxide coating) according to an appropriate coating method with a spinner or a coater in an optional thickness (generally from 50 to 500 nm). After coating, the coated film is dried by spinning or baking to form a resist film. The temperature of baking can be arbitrarily set, generally from 60 to 150° C., and preferably from 90 to 130° C.

The resist film is then subjected to exposure through a mask for forming a pattern.

The quantity of exposure can be optionally set, but is generally from 1 to 100 mJ/cm$^2$. After exposure, it is preferred to perform spinning or/and baking, and then development and rinsing to thereby obtain a pattern.

At the time of irradiation with actinic ray or radiation, exposure (immersion exposure) may be performed by filling a liquid (an immersion medium) having a higher refractive index than that of air between a photosensitive film and a lens, by which resolution can be raised. As the immersion medium to be used, any liquids can be used so long as they are liquids higher in refractive index than air, but pure water is preferred.

An overcoat layer may further be provided on a photosensitive film so that an immersion medium and the photosensitive film are not directly touched in performing immersion exposure, by which the elution of the photosensitive composition from the photosensitive film to the immersion medium is restrained and development defect is reduced.

As actinic rays or radiations, infrared rays, visible rays, ultraviolet rays, far ultraviolet rays, X-rays and electron beams can be exemplified, and preferably far ultraviolet rays of wavelengths of 250 nm or less, and more preferably 220 nm or less are used. Specifically, a KrF excimer laser (248 nm), an ArF excimer laser (193 nm), an F$_2$ excimer laser (157 nm), EUV (13 nm), X-rays and electron beams are exemplified, and an ArF excimer laser, an F$_2$ excimer laser, EUV (13 nm), and electron beams are preferred.

Before forming a photosensitive film, an antireflection film may be coated previously on a substrate.

As the antireflection film, any of inorganic film types, e.g., titanium, titanium dioxide, titanium nitride, chromium oxide, carbon, amorphous silicon, etc., and an organic film type comprising a light absorber and a polymer material can be used. Further, commercially available organic antireflection films such as DUV-30 series and DUV-40 series (manufactured by Brewer Science), and AR-2, AR-3 and AR-5 (manufactured by Shipley Company LLC) can also be used.

In a development process, an alkali developer is used as follows. As alkali developers for resist compositions, alkaline aqueous solutions of inorganic alkalis, e.g., sodium hydroxide, potassium hydroxide, sodium carbonate, sodium silicate, sodium metasilicate, aqueous ammonia, etc., primary amines, e.g., ethylamine, n-propylamine, etc., secondary amines, e.g., diethylamine, di-n-butylamine, etc., tertiary amines, e.g., triethylamine, methyldiethylamine, etc., alcohol amines, e.g., dimethylethanolamine, triethanolamine, etc., quaternary ammonium salts, e.g., tetramethylammonium hydroxide, tetraethylammonium hydroxide, etc., and cyclic amines, e.g., pyrrole, piperidine, etc., can be used.

An appropriate amount of alcohols and surfactants may be added to these alkali developers.

The alkali concentration of the alkali developers is generally from 0.1 to 20 mass %.

The pH of the alkali developers is generally from 10.0 to 14.0.

The positive resist composition in the invention may be applied to a multilayer resist process (in particular, three-layered resist process). A multilayer resist method includes the following processes.

(a) A lower resist layer comprising organic materials is formed on a substrate to be processed.

(b) An intermediate layer and an upper resist layer comprising organic materials capable of crosslinking or decomposing upon irradiation with radiation are laminated on the lower resist layer in order.

(c) After a prescribed pattern is formed on the upper resist layer, the intermediate layer, the lower layer and the substrate are subjected to etching in order.

As the intermediate layer, organopolysiloxane (a silicone resin) or an SiO$_2$ coating solution (SOG) is generally used. As the lower layer resist, a proper organic polymer film is used, but various well-known photoresists may be used. For example, each series such as FH series and FHi series (manufactured by Fuji Film Arch Chemicals, Inc.), and PFI series (manufactured by Sumitomo Chemical Co., Ltd.) can be exemplified.

The thickness of the lower resist layer is preferably from 0.1 to 4.0 μm, more preferably from 0.2 to 2.0 μm, and especially preferably from 0.25 to 1.5 μm. The thickness of 0.1 μm or more is preferred in the point of an antireflection property and dry etching resistance, and 4.0 μm or less is preferred from the viewpoint of aspect ratio, and prevention of falling down of the pattern of a formed micro pattern.

EXAMPLE

The invention will be described with reference to examples, but the invention should not be construed as being restricted thereto.

Synthesis Example 1

Synthesis of Compound (I-1)

Trifluoromethanesulfonamide (5 g) is dissolved in 50 ml of water, and 2.7 g of sodium hydroxide is added to the above solution. While cooling with ice, 3.8 g of methanesulfonyl chloride is dropped to the solution. The above reaction mixture is subjected to reaction at room temperature for 5 hours, and to the reaction solution is added a solution obtained by dissolving 4.6 g of triphenylsulfonium bromide in a mixed solvent comprising 10 ml of methanol and 50ml of water. The supernatant is removed, and an oily substance is dissolved in chloroform. The resulting reaction product is washed with water, concentrated, and washed with diisopropyl ether to obtain 2 g of Compound (I-1).

$^1$H—NMR (CDCl$_3$)

δ 3.1 (s, 3), δ 7.6-7.8 (m, 15 H)

Other components (A) are also synthesized according to the same method.

The structures of Compounds (I-1) to (I-9) of components (A) are shown below.

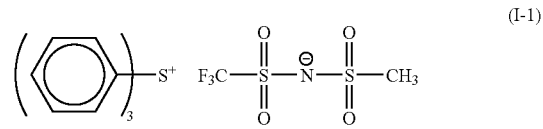

(I-1)

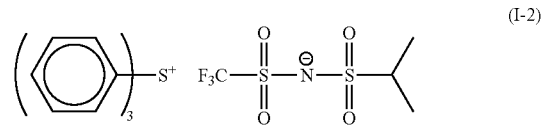

(I-2)

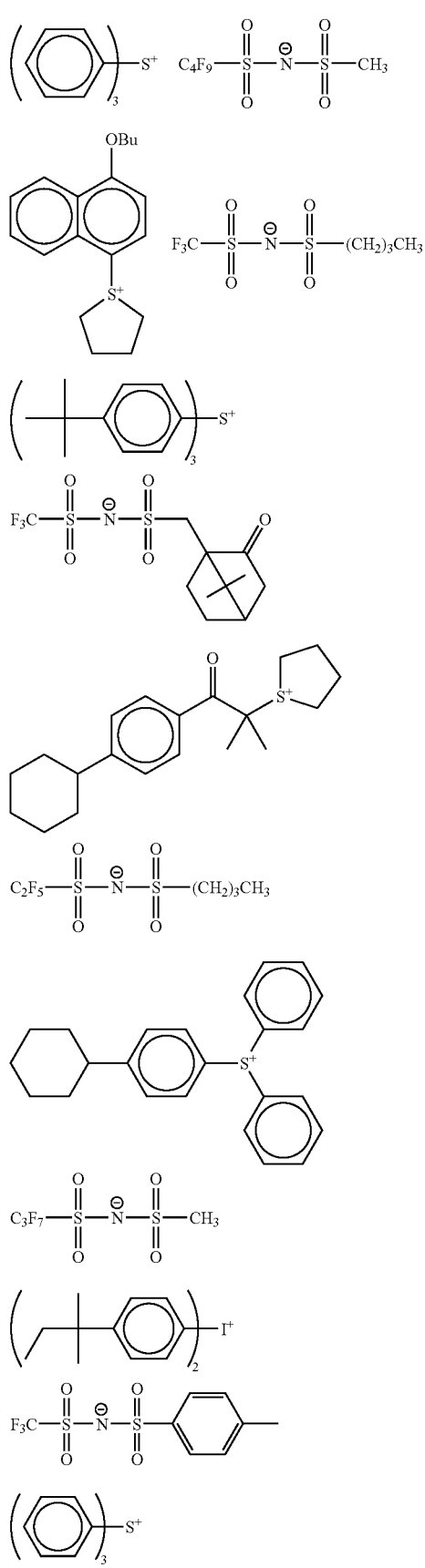

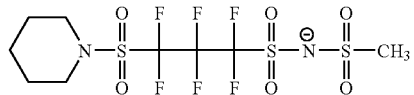

Synthesis Example 2

Synthesis of Compound (RA-1)

Under nitrogen current, 8.4 g of cyclohexanone is put into a three-neck flask and heated at 80° C. A solution obtained by dissolving 6.8 g of γ-butyrolactone methacrylate, 4.7 g of 3-hydroxyadamantyl-1-methacrylate, 9.4 g of 2-methyl-2-adamantyl methacrylate, and 13 mol % based on the monomer of a polymerization initiator V-60 (manufactured by Wako Pure Chemical Industries) in 75 g of cyclohexanone is dropped into the above flask over 6 hours. After termination of dropping, the solution is further reacted at 80° C. for 2 hours. After being left to cool down, the reaction solution is dropped to a mixed solution comprising 900 ml of methanol and 100 ml of water over 20 minutes, and precipitated powder is filtered out and dried to obtain 178 g of resin (RA-1). The weight average molecular weight of the resin obtained is 6,300 as standard polystyrene equivalent, and the degree of dispersion (Mw/Mn) is 1.60.

Resins (RA-2) to (RA-12) are also synthesized according to the same manner. The weight average molecular weight of each resin is adjusted by modifying the amount of the polymerization initiator.

The structures, molar ratios of repeating units, weight average molecular weights, and degrees of dispersion of Resins (RA-1) to (RA-12) are shown below.

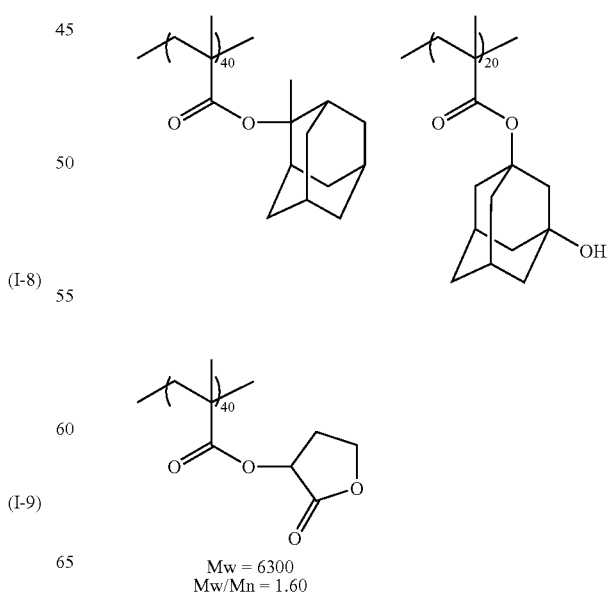

RA-1

Mw = 6300
Mw/Mn = 1.60

-continued
RA-2
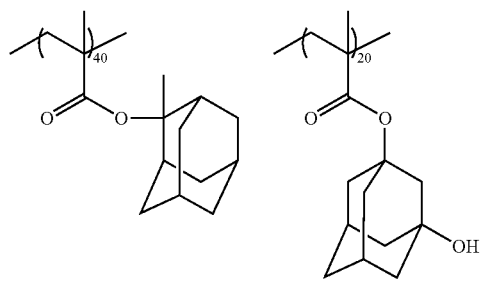
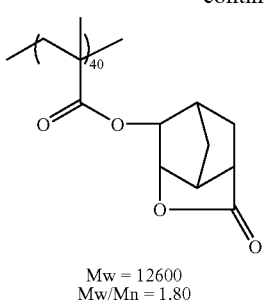
Mw = 12600
Mw/Mn = 1.80
RA-5
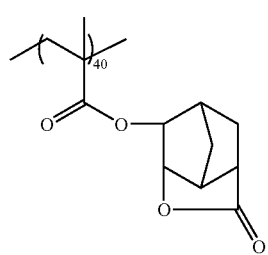
Mw = 11200
Mw/Mn = 1.65
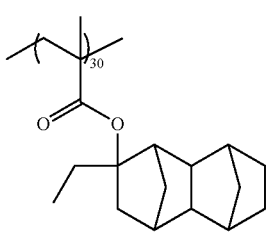
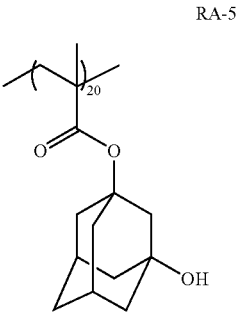
RA-3
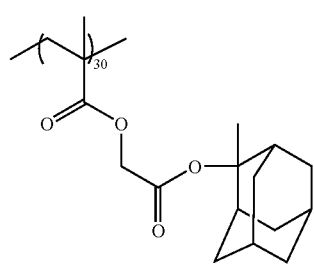
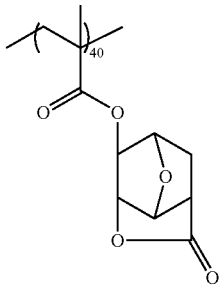
Mw = 8400
Mw/Mn = 1.74
RA-6
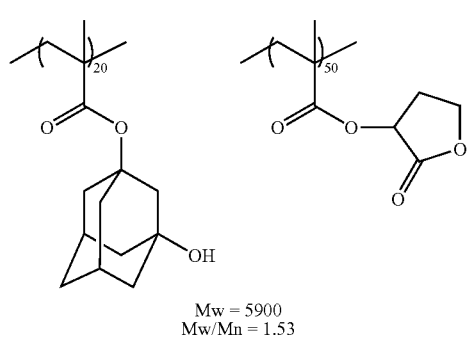
Mw = 5900
Mw/Mn = 1.53
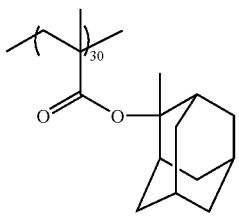
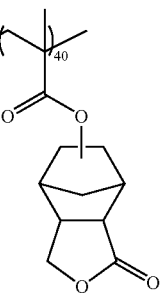
RA-4
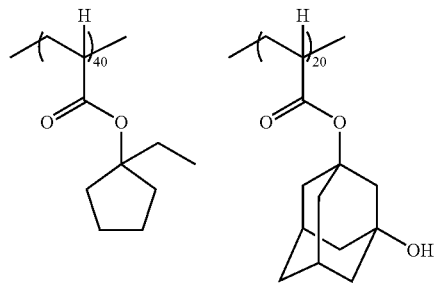
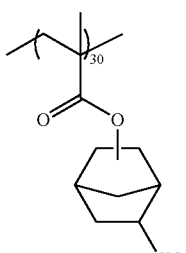
Mw = 19600
Mw/Mn = 1.90

RA-7
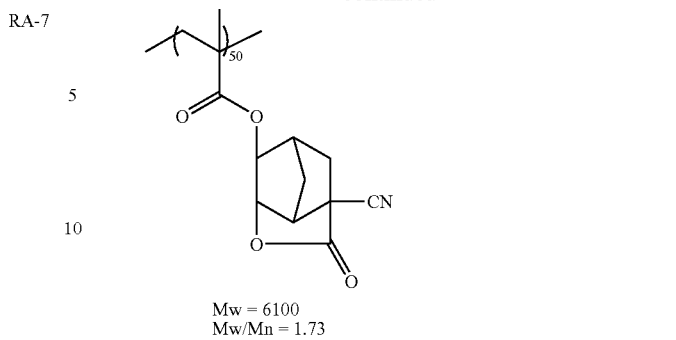
Mw = 6100
Mw/Mn = 1.73
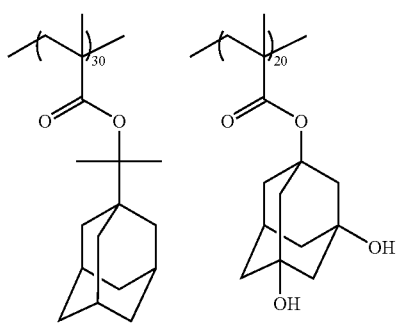
Mw = 8900
Mw/Mn = 1.80
RA-8
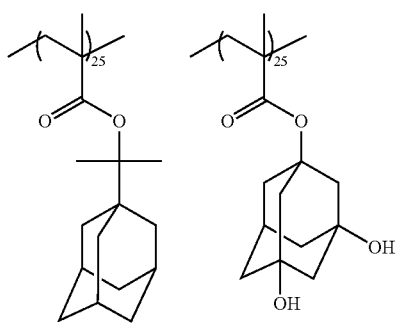
Mw = 9300
Mw/Mn = 1.79
RA-9
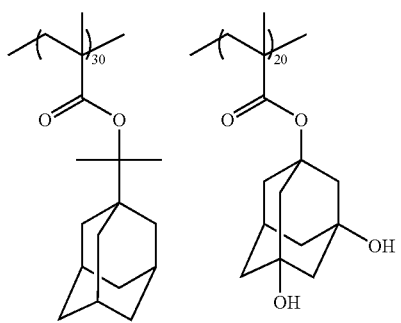
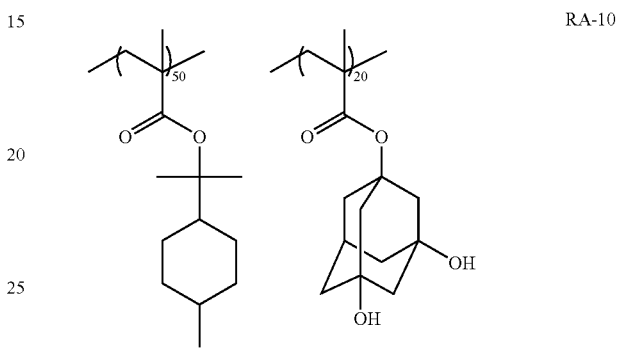
RA-10
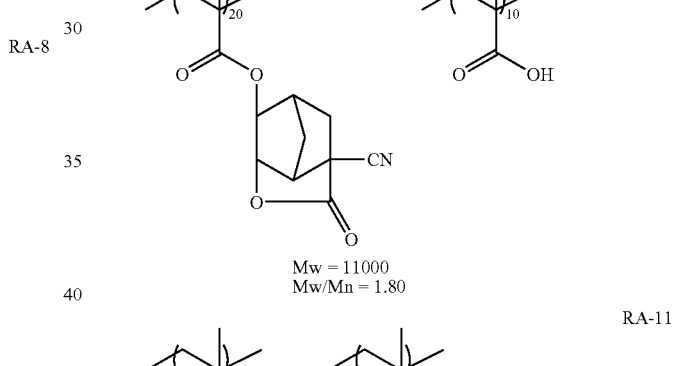
Mw = 11000
Mw/Mn = 1.80
RA-11
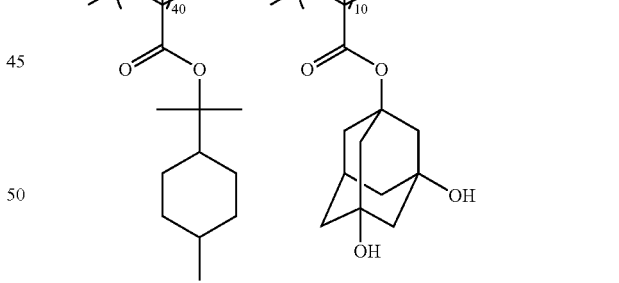
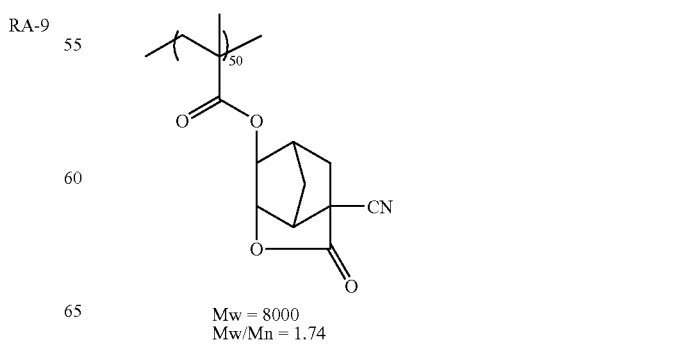
Mw = 8000
Mw/Mn = 1.74

-continued

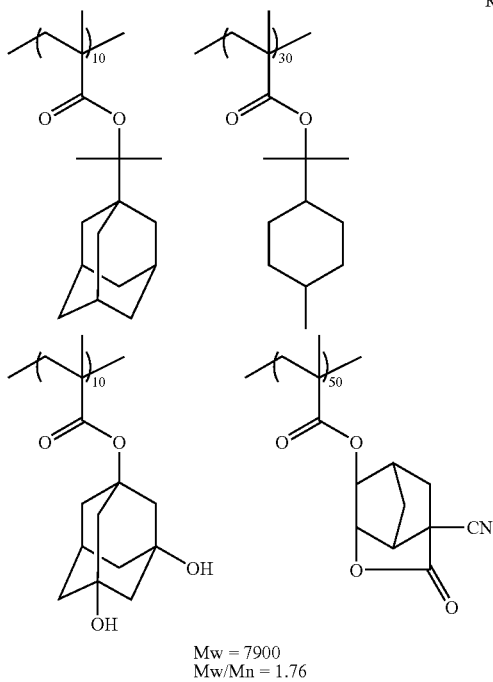

RA-12

Mw = 7900
Mw/Mn = 1.76

Examples 1 to 13 and Comparative Examples 1 and 2

Preparation of Resist:

A solution having the concentration of solids content of 6 mass % is prepared by dissolving the components in the solvent shown in Table 1 below, and a positive resist solution is prepared by filtrating the above-prepared solution through a polyethylene filter having a pore size of 0.03 μm. The thus prepared positive resist solution is evaluated according to the following methods. The results of evaluations are shown in Table 1.

Evaluation of Resist:

An antireflection film DUV-42 (manufactured by Brewer Science) is uniformly coated on a silicon substrate having been subjected to hexamethyldisilazane treatment in a thickness of 600 Å by a spin coater, the film is dried on a hot plate at 100° C. for 90 seconds, and then heated at 190° C. for 240 seconds. After that, each positive resist solution is coated thereon by a spin coater and dried at 120° C. for 90 seconds to form a resist film having a thickness of 160 nm.

The resist film is subjected to exposure through a mask with an ArF excimer laser stepper (NA: 0.6, dipole, manufactured by ASML), and heated on a hot plate at 120° C. for 60 seconds just after exposure. Further, the resist film is developed with a 2.38 mass % tetramethylammonium hydroxide aqueous solution at 23° C. for 60 seconds, rinsed with pure water for 30 seconds, and then dried to form a line pattern.

Exposure Latitude:

Taking the exposure amount required to reproduce the mask pattern of line and space of line width 80 nm as the optimal exposure amount, the breadth of exposure amount of a pattern size tolerating 80 nm±10% when exposure amount is varied is found. The obtained value is divided by the optimal exposure amount and the exposure latitude is shown in percentage. The greater the value, the smaller is the fluctuation of performance due to the variation of exposure amount, and exposure latitude is good.

PEB Temperature Dependency:

When post baking is performed at 120° C. for 90 seconds, the exposure amount required to reproduce line and space 1/1 of mask size 80 nm is taken as the optimal exposure amount. After exposure by the optimal exposure amount, post baking at two temperatures of post baking temperature +2° C. and −2° C. (122° C. and 118° C.) is performed, and each line and space obtained is measured and line widths $L_1$ and $L_2$ are found. PEB temperature dependency is defined as fluctuation of line width per 1° C. of PEB temperature change, and computed from the following expression.

$$PEB \text{ Temperature dependency } (nm/° C.) = |L_1 - L_2|/4$$

The smaller the value, the smaller is the fluctuation of performance to the variation of temperature, i.e., good.

TABLE 1

| Example No. | Acid Generator (g) | Resin (10 g) | Basic Compound (g) | Surfactant (g) | Solvent (mass ratio) | Exposure Latitude (%) | PEB Temperature Dependency (nm/° C.) |
|---|---|---|---|---|---|---|---|
| Example 1 | I-1 (0.5) | RA-1 | DIA (0.05) | W-4 (0.01) | S1/S5 (60/40) | 13.3 | 2.5 |
| Example 2 | I-2 (0.2) PAG-1 (0.2) | RA-2 | PEA (0.05) | W-2 (0.02) | S1/S4/S2 (80/5/15) | 13.6 | 2.7 |
| Example 3 | I-3 (0.3) PAG-4 (0.2) | RA-3 | TEA (0.03) | W-1 (0.01) | S1/S6 (95/5) | 13.4 | 2.5 |
| Example 4 | I-4 (0.6) | RA-4 | DIA (0.03) | W-4 (0.01) | S1/S5/S7 (60/38/2) | 13.5 | 2.8 |
| Example 5 | I-5 (0.3) PAG-5 (0.2) | RA-5 | PEA (0.02) | W-4 (0.01) | S1/S5 (80/20) | 13.4 | 2.6 |
| Example 6 | I-6 (0.4) PAG-2 (0.3) | RA-6 | DIA (0.02) PEA (0.02) | W-4 (0.01) | S1/S4/S6 (80/5/15) | 13.3 | 2.5 |
| Example 7 | I-7 (0.3) PAG-6 (0.3) | RA-7 | TMEA (0.03) | W-3 (0.03) | S1/S3 (60/40) | 14.5 | 2.2 |
| Example 8 | I-8 (0.5) | RA-8 | PBI (0.04) | W-1 (0.005) | S1/S6 (80/20) | 14.2 | 2.4 |
| Example 9 | I-9 (0.6) | RA-9 | DIA (0.03) | W-3 (0.02) | S1/S5 (60/40) | 15.3 | 1.9 |
| Example 10 | I-1 (0.5) | RA-10 | TPSA (0.05) | W-3 (0.01) | S1/S5 (60/40) | 15.3 | 1.8 |
| Example 11 | I-9 (0.5) | RA-11 | DIA (0.05) | W-4 (0.01) | S1/S5 (60/40) | 15.7 | 1.9 |
| Example 12 | I-1 (0.5) | RA-12 | PEA (0.05) | W-4 (0.01) | S1/S5 (60/40) | 15.3 | 1.9 |
| Example 13 | I-1 (0.4) PAG-3 (0.1) | RA-9 (5 g) RA-11 (5 g) | DIA (0.02) PEA (0.02) | W-4 (0.01) | S1/S4/S6 (80/5/15) | 15.3 | 1.8 |
| Comparative Example 1 | PAG-A (0.5) | RA-1 | DIA (0.05) | W-4 (0.01) | S1/S5 (60/40) | Impossible of image formation | Impossible of image formation |
| Comparative Example 2 | PAG-B (0.5) | RA-1 | DIA (0.05) | W-4 (0.01) | S1/S5 (60/40) | 13.1 | 6.3 |

The abbreviations in Table 1 are shown below.

Acid Generators:

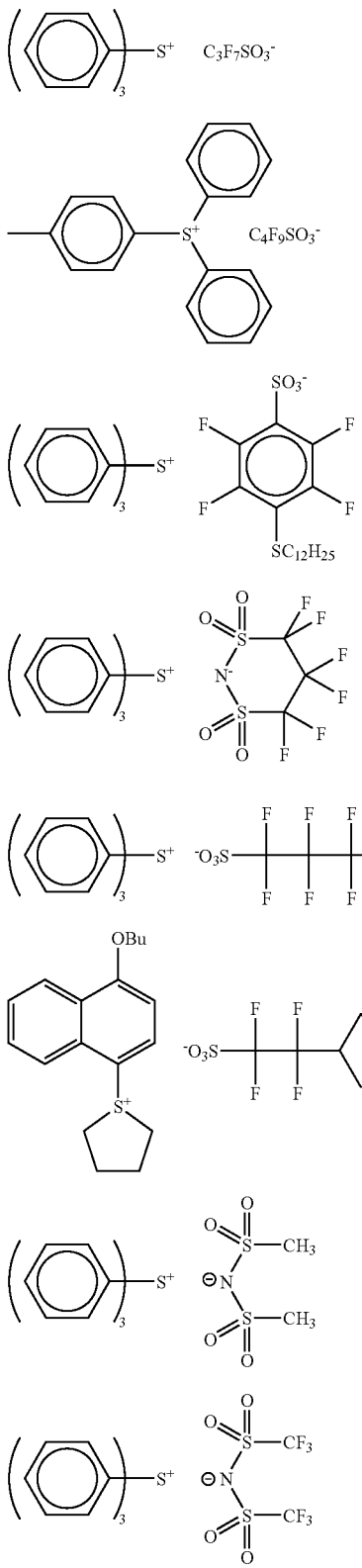

(PAG-1)
(PAG-2)
(PAG-3)
(PAG-4)
(PAG-5)
(PAG-6)
(PAG-A)
(PAG-B)

Basic Compounds:
TPSA: Triphenylsulfonium acetate
DIA: 2,6-Diisopropylaniline
TEA: Triethanolamine
PBI: 2-Phenylbenzimidazole
TMEA: Tris(methoxyethoxyethyl)amine
PEA: N-Phenyldiethanolamine Surfactants:
W-1: Megafac F176 (fluorine surfactant, manufactured by Dainippon Ink and Chemicals Inc.)
W-2: Megafac R08 (fluorine/silicon surfactant, manufactured by Dainippon Ink and Chemicals Inc.)
W-3: Polysiloxane polymer KP-341 (silicon surfactant, manufactured by Shin-Etsu Chemical Co., Ltd.)
W-4: Troy Sol S-366 (silicon surfactant, manufactured by Troy Chemical Co., Ltd.)

Solvents:
S1: Propylene glycol methyl ether acetate
S2: 2-Heptanone
S3: Cyclohexanone
S4: γ-Butyrolactone
S5: Propylene glycol methyl ether
S6: Ethyl lactate
S7: Propylene carbonate It can be seen from the results shown in Table 1 that the photosensitive compositions in the invention are excellent in exposure latitude and PEB temperature dependency.

Examples 14 to 26 and Comparative Example 3

Preparation of Resist:

A solution having the concentration of solids content of 5 mass % is prepared by adding 0.2 g of the surface hydrophobitizing resin shown below (Polymer A) to each of the components in Examples 1 to 13 and Comparative Example 2 shown in Table 1 and dissolving the mixture in the solvent. A positive resist solution is prepared by filtrating the above-prepared solution through a polyethylene filter having a pore size of 0.03 μm. Each positive resist solution prepared is evaluated by the following method. The composition is coated by a spin coater and dried at 120° C. for 60 seconds to prepare a resist film having a thickness of 160 nm, and the sweepback contact angle of pure water of the resist film at this time is from 65 to 75°.

Evaluation of Resolution:

Exposure latitude and PEB temperature dependency are evaluated in the same manner as in Examples 1 to 13 except for performing immersion exposure with ArF excimer laser immersion scanner (NA: 0.85) and extra pure water as the immersion liquid. The results obtained are shown in Table 2 below.

(Polymer-A)

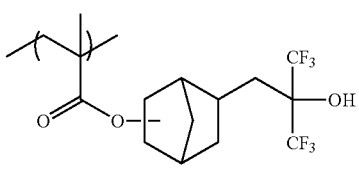

Mw: 6700
Mw/Mn:1.57

TABLE 2

| Example No. | Exposure Latitude (%) | PEB Temperature Dependency (nm/° C.) |
|---|---|---|
| Example 14 | 14.7 | 2.1 |
| Example 15 | 14.6 | 2.4 |
| Example 16 | 14.5 | 2.2 |
| Example 17 | 14.5 | 2.4 |
| Example 18 | 14.6 | 2.2 |
| Example 19 | 14.2 | 2.3 |
| Example 20 | 15.5 | 2.0 |
| Example 21 | 15.4 | 2.0 |
| Example 22 | 16.3 | 1.6 |
| Example 23 | 16.6 | 1.7 |
| Example 24 | 16.3 | 1.7 |
| Example 25 | 16.5 | 1.6 |
| Example 26 | 17.1 | 1.7 |
| Comparative Example 3 | 13.8 | 5.1 |

It can be seen from the results shown in Table 2 that the photosensitive compositions in the invention are excellent in exposure latitude and PEB temperature dependency in immersion exposure.

Examples 27 to 32 and Comparative Examples 4 and 5

The components shown in Tables 3 and 4 below are dissolved in the solvent and filtered through a polyethylene filter having a pore diameter of 0.03 μm to prepare a positive resist solution having the concentration of solids content of 14 mass %. The prepared positive resist solution is evaluated according to the methods shown below, and the results obtained are shown in Tables 3 and 4.

Evaluation of Resist:

The prepared positive resist solution is uniformly coated on a silicon substrate having been subjected to hexamethyldisilazane treatment by a spin coater, and the coated solution is dried by heating on a hot plate at 120° C. for 90 seconds to form a resist film having a thickness of 0.4 μm.

The resist film is subjected to pattern exposure through a mask for line and space with a KrF excimer laser stepper (NA: 0.63), and heated on a hot plate at 110° C. for 90 seconds just after exposure. Further, the resist film is developed with a 2.38 mass % tetramethylammonium hydroxide aqueous solution at 23° C. for 60 seconds, rinsed with pure water for 30 seconds, and then dried to form a line pattern.

Exposure Latitude:

Taking the exposure amount required to reproduce the mask pattern of line and space of line width 130 nm as the optimal exposure amount, the breadth of exposure amount of a pattern size tolerating 130 nm±10% when exposure amount is varied is found. The obtained value is divided by the optimal exposure amount and the exposure latitude is shown in percentage. The greater the value, the smaller is the fluctuation of performance due to the variation of exposure amount, and exposure latitude is good.

PEB Temperature Dependency:

When post baking is performed at 110° C. for 90 seconds, the exposure amount required to reproduce line and space 1/1 of mask size 130 nm is taken as the optimal exposure amount. After exposure by the optimal exposure amount, post baking at two temperatures of post baking temperature +2° C. and −2° C. (112° C. and 108° C.) is performed, and each line and space obtained is measured and line widths $L_1$ and $L_2$ are found. PEB temperature dependency is defined as fluctuation of line width per 1° C. of PEB temperature change, and computed from the following expression.

PEB Temperature dependency $(nm/° C.) = |L_1 - L_2|/4$

The smaller the value, the smaller is the fluctuation of performance to the variation of temperature, i.e., good.

TABLE 3

| Example No. | Acid Generator (g) | Resin (10 g) | Basic Compound (g) | Surfactant (g) | Solvent (mass ratio) | Exposure Latitude (%) | PEB Temperature Dependency (nm/° C.) |
|---|---|---|---|---|---|---|---|
| Example 27 | I-1 (0.5) | RA-4 | DIA (0.05) | W-4 (0.01) | S1/S5 (60/40) | 12.3 | 1.1 |
| Example 28 | I-2 (0.4) PAG-7 (0.2) | RA-7 | PEA (0.06) | W-2 (0.02) | S1/S4/S2 (80/5/15) | 11.6 | 2.0 |
| Example 29 | I-5 (0.3) PAG-8 (0.3) | RA-8 | TEA (0.06) | W-1 (0.01) | S1/S6 (95/5) | 12.4 | 0.6 |
| Example 30 | I-8 (0.3) PAG-8 (0.3) | RA-16 | DIA (0.05) | W-4 (0.01) | S1/S5/S7 (60/38/2) | 12.5 | 1.6 |
| Comparative Example 4 | PAG-A (0.5) | RA-4 | DIA (0.05) | W-4 (0.01) | S1/S5 (60/40) | 11.1 | 4.3 |
| Comparative Example 5 | PAG-B (0.5) | RA-4 | DIA (0.05) | W-4 (0.01) | S1/S5 (60/40) | 10.1 | 3.2 |

TABLE 4

| Example No. | Acid Generator (g) | Resin (10 g) | Basic Compound (g) | Surfactant (g) | Solvent (mass ratio) | Exposure Latitude (%) | PEB Temperature Dependency (nm/° C.) |
|---|---|---|---|---|---|---|---|
| Example 31 | I-1 (0.5) | R-4 | N-1 (0.06) | W-4 (0.01) | S1/S5 (60/40) | 12.1 | 1.4 |
| Example 32 | I-3 (0.6) | R-7 | N-2 (0.05) | W-4 (0.01) | S1/S5 (60/40) | 12.4 | 1.5 |

The abbreviations in Tables are shown below.
Acid Generators:
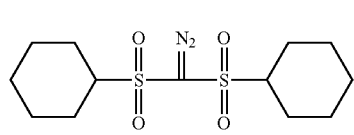
(PAG-7)
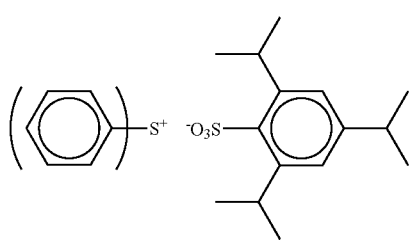
(PAG-8)
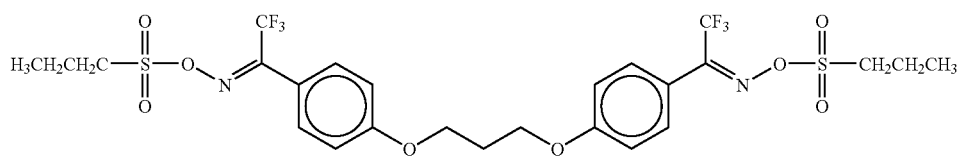
(PAG-9)
Resins:
The structures, molar ratios of repeating units, weight average molecular weights, and degrees of dispersion of Resins (R-4), (R-7), (R-8) and (R-16) are shown below.
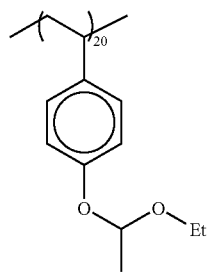
(R-4)
Mw: 8000
Mw/Mn: 1.78
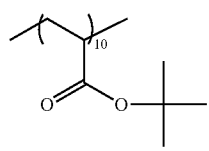
(R-7)
Mw: 11000
Mw/Mn: 1.69
-continued
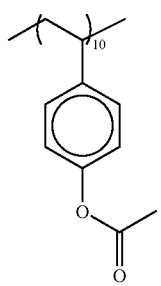
(R-8)
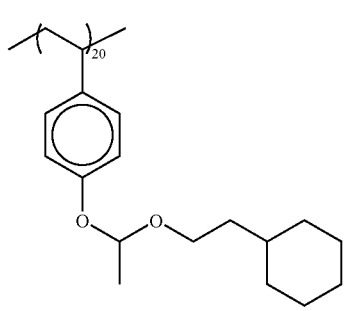
Mw: 12000
Mw/Mn: 1.15
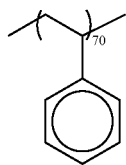
(R-16)

-continued

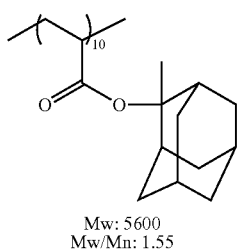

Mw: 5600
Mw/Mn: 1.55

Basic Compounds:

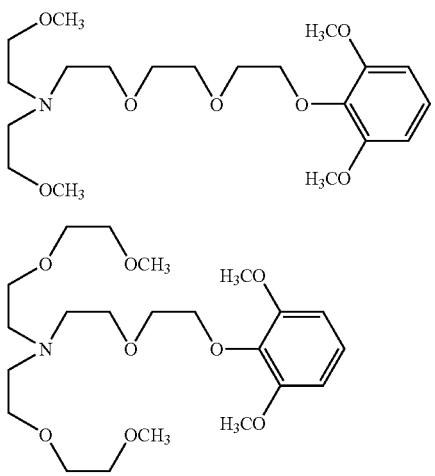

N-1

N-2

Sensitivity:

The resist film is irradiated with an electron beam projection lithography apparatus (accelerating voltage: 100 keV, manufactured by Nikon Corporation) for areal exposure by changing the exposure amount by 1 µC/cm² at a time in the range of from 0 to 30 µC/cm², and then baked at 110° C. for 90 seconds. After that, the resist film is developed with a 2.38 mass % tetramethylammonium hydroxide (TMAH) aqueous solution, and the exposure amount required for the film thickness to reach 0 is found by fitting.

Exposure Latitude (%) (EL):

In exposure of line and space of 1/1, a line width of 150 nm is taken as standard, and the exposure latitude is expressed by the rate of change of exposure amount required for the line width to change by 10%.

PEB Temperature Dependency:

When post baking is performed at 110° C. for 90 seconds, in the exposure of line and space of 1/1, a line width of 150 nm is taken as standard. After exposure by the same exposure amount as above, post baking at two temperatures of post baking temperature +2° C. and −2° C. (112° C. and 108° C.) is performed, and each line and space obtained is measured and their line widths $L_1$ and $L_2$ are found. PEB temperature dependency is defined as fluctuation of line width per 1° C. of PEB temperature change, and computed from the following expression.

$$PEB \text{ Temperature dependency } (nm/°C.)=|L_1-L_2|/4$$

The smaller the value, the smaller is the fluctuation of performance to the variation of temperature, i.e., good.

TABLE 5

| Example No. | Acid Generator (g) | Resin (10 g) | Basic Compound (g) | Surfactant (g) | Solvent (mass ratio) | Sensitivity (µC/cm²) | Exposure Latitude (%) | PEB Temperature Dependency (nm/° C.) |
|---|---|---|---|---|---|---|---|---|
| Example 33 | I-5 (0.06) | R-8 | DIA (0.03) | W-1 (0.02) | S1/S5 (60/40) | 14.2 | 17.3 | 0.8 |
| Example 34 | I-5 (0.03) PAG-8 (0.03) | R-8 | DIA (0.03) | W-1 (0.02) | S1/S5 (60/40) | 13.6 | 17.3 | 1.1 |
| Comparative Example 6 | PAG-A (0.06) | R-8 | DIA (0.03) | W-1 (0.02) | S1/S5 (60/40) | 14.1 | 16.3 | 2.0 |

It can be seen from the results shown in Tables 3 and 4 that the photosensitive compositions in the invention are excellent in exposure latitude and PEB temperature dependency.

Examples 33 and 34, and Comparative Example 6

<Preparation of Resist>

A solution having the concentration of solids content of 6 mass % is prepared by dissolving the components in the solvent respectively shown in Table 5 below, and a positive resist solution is prepared by filtrating the above-prepared solution through a polytetrafluoroethylene filter having a pore size of 0.1 µm.

<Evaluation of Resist>

The prepared positive resist solution is uniformly coated with a spin coater on a silicon substrate having been subjected to hexamethyldisilazane treatment, and dried at 120° C. for 60 seconds on a hot plate to form a resist film having a thickness of 150 nm.

From the results shown in Table 5, it can be seen that a photosensitive composition that is well balanced between sensitivity and EL, and excellent in PEB temperature dependency can be obtained according to the invention.

The similar effects can also be obtained in EUV and X-ray lithography.

A photosensitive composition improved in PEB temperature dependency and exposure latitude and a pattern-forming method using the same can be provided according to the invention.

The entire disclosure of each and every foreign patent application from which the benefit of foreign priority has been claimed in the present application is incorporated herein by reference, as if fully set forth.

What is claimed is:

1. A photosensitive composition comprising:
   (A) a compound capable of generating an acid represented by formula (I) upon irradiation with actinic ray or radiation; and (B) a resin that decomposes by the action of an acid to increase its solubility in an alkali developer

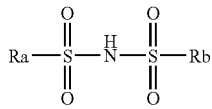
(I)

wherein Ra represents an alkyl group substituted with a fluorine atom, or an aryl group substituted with a fluorine atom or a group having a fluorine atom;

Rb represents an alkyl group not substituted with a fluorine atom on an α-position of the alkyl group, or a phenyl group not substituted with a fluorine atom or a group having a fluorine atom, provided that the alkyl group represented by Rb is selected from the group consisting of an alkyl group not having a substituent and an alkyl group having any of an alkoxyl group, an alkoxycarbonyl group, a cyano group and an oxo group as a substituent, and further provided that the phenyl group represented by Rb is selected from the group consisting of a phenyl group not having a substituent and a phenyl group having any of an alkyl group, an alkoxyl group, an alkoxycarbonyl group and a cyano group as a substituent; and all the repeating units of resin (B) consist of (meth)acrylate repeating units.

2. The photosensitive composition as claimed in claim 1, wherein the compound (A) is a sulfonium salt compound or an iodonium salt compound having an anion of an acid represented by formula (I).

3. A pattern-forming method comprising:
forming a photosensitive film with the photosensitive composition as claimed in claim 1; and
exposing and developing the photosensitive film.

4. The pattern-forming method according to claim 3, wherein the step of exposing the photosensitive film is an immersion exposure step.

5. The pattern-forming method according to claim 3, wherein the step of exposing the photosensitive film is performed using an ArF excimer laser.

6. The photosensitive composition according to claim 1, wherein resin (B) contains a repeating unit having a structure represented by any of the following formulae (VIIa) to (VIId):

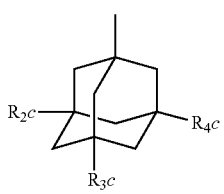
(VIIa)

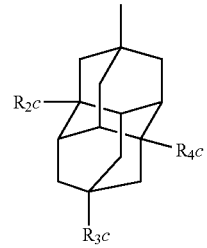
(VIIb)

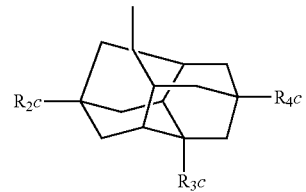
(VIIc)

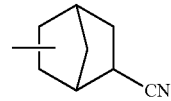
(VIId)

wherein in formula (VIIa) to (VIIc), $R_{2c}$, $R_{3c}$ and $R_{4c}$ each represents a hydrogen atom, a hydroxyl group, or a cyano group, provided that at least one of $R_{2c}$, $R_{3c}$ and $R_{4c}$ represents a hydroxyl group or a cyano group.

7. The photosensitive composition according to claim 1, further comprising a surface hydrophobitizing resin.

8. The photosensitive composition according to claim 1, wherein compound (A) is a compound represented by the following formula (ZIa):

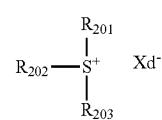
ZIa wherein in formula (ZIa), $R_{201}$, $R_{202}$ and $R_{203}$ each represents an organic group, provided that at least one of $R_{201}$, $R_{202}$ and $R_{203}$ in formula (ZIa) represents an aryl group; and Xd⁻ represents an anion of the acid represented by formula (I).

* * * * *